(12) United States Patent
Shiga et al.

(10) Patent No.: US 7,425,563 B2
(45) Date of Patent: Sep. 16, 2008

(54) 4-(SUBSTITUTED ARYL)-5-HYDROXYISOQUINOLINONE DERIVATIVE

(75) Inventors: Futoshi Shiga, Shimotsuga-gun (JP); Takahiro Kanda, Oyama (JP); Tetsuya Kimura, Koga (JP); Yasuo Takano, Kazo (JP); Jyunichi Ishiyama, Saitama (JP); Tomoyuki Kawai, Shimotsuga-gun (JP); Tsuyoshi Anraku, Shimotsuga-gun (JP); Kumi Ishikawa, Utsunomiya (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 177 days.

(21) Appl. No.: 10/521,565

(22) PCT Filed: Jul. 23, 2003

(86) PCT No.: PCT/JP03/09332

§ 371 (c)(1),
(2), (4) Date: Jan. 18, 2006

(87) PCT Pub. No.: WO2004/009556

PCT Pub. Date: Jan. 29, 2004

(65) Prior Publication Data

US 2006/0173039 A1      Aug. 3, 2006

(30) Foreign Application Priority Data

Jul. 24, 2002    (JP) ............................... 2002-214673

(51) Int. Cl.
*C07D 217/24* (2006.01)
*C07D 401/12* (2006.01)
*A61K 31/47* (2006.01)

(52) U.S. Cl. ...................................... 514/310; 546/141

(58) Field of Classification Search ............... 546/141; 514/310

See application file for complete search history.

(56) References Cited

U.S. PATENT DOCUMENTS 4,897,391 A     1/1990   Friary

FOREIGN PATENT DOCUMENTS

| EP | 355750 | 2/1990 |
| WO | 99/11628 | 3/1999 |
| WO | 02/094790 | 11/2002 |

*Primary Examiner*—Zinna N Davis
(74) *Attorney, Agent, or Firm*—Oblon, Spivak, McClelland, Maier & Neustadt, P.C.

(57) ABSTRACT

The invention provides 4-substituted aryl-5-hydroxyisoquinolinone derivatives and their pharmacologically acceptable addition salts with excellent inhibitory effect on poly (ADP-ribose) synthetase.

4-Substituted aryl-5-hydroxyisoquinolinone derivatives, represented by a general formula (1)

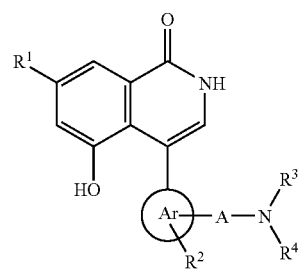

(1)

and their pharmacologically acceptable addition salts.

12 Claims, No Drawings

4-(SUBSTITUTED ARYL)-5-HYDROXYISOQUINOLINONE DERIVATIVE

TECHNICAL FIELD

The present invention relates to 4-substituted aryl-5-hydroxyisoquinolinone derivatives, their pharmacologically acceptable addition salts, and an inhibitor of poly (ADP-ribose) polymerase containing these as effective ingredients.

BACKGROUND TECHNOLOGIES

Poly (ADP-ribose) polymerase (hereinafter, abbreviated as "PARP", another name: poly (ADP-ribose) synthetase) is a protein that regulates the function of nuclear DNA, and an enzyme that is activated by recognizing the damage of DNA to successively transfer poly (ADP-ribose) to acceptor proteins such as DNA-polymerase, utilizing NAD (nicotinamide adenine dinucleotide) being an essential constitutive element in cell as an enzyme substrate. It is considered therefore that the excessive activation of PARP may cause decreased capacity of energy production in cell based on the depletion of NAD essential for the electron transport system and result in cell death (C. Szabo, Free Radic. Biol. Med., 21, 855(1996)). Moreover, PARP has also been attracting attention as an apoptosis-relevant enzyme from the fact that caspase-3, one of the interleukin-1b conversion enzyme-like protease family, cleaves PARP as substrate.

Furthermore, it is reported from an experiment using PARP-knockout mice that the cultured nerve cells obtained from the brain of the knockout mice exhibit resistance to the injury due to nitric oxide and excitatory amino acids such as NMDA (N-methyl-D-aspartate) and that in this knockout mouse, the infarction volume due to cerebral ischemia is reduced by about 80% or more (M. J. L. Eliassonetal., Nature Med., 3, 1089(1997)). From these facts, it is considered that the PARP inhibitor would be effective for cerebral infarction and neurodegenerative diseases (Alzheimer's disease, Huntington's chorea, Parkinson disease, etc.). Besides, there is a report that describes that it would be effective for diabetes, diseases due to ischemia or ischemia-reperfusion such as cardiac infarction and acute renal failure, circulatory diseases such as septic shock, and inflammatory diseases such as chronic rheumatism and multiple sclerosis (C. Szabo et al., Trend pharmacol. Sci., 19, 287(1998)). It is also reported that the PARP inhibitor would be effective as an antiretrovirus agent including HIV (G. A. Cole et al., Biochem. Biophys. Res. Commun., 180, 504(1991)) and a sensitizer for anticancer therapeutics (C. Arundel-Suto, et al., Radiat. Res., 126, 367 (1991); S. Boulton et al., Br. J. Cancer, 72, 849(1995)).

Based on the facts as above, it is expected that a compound with the PARP inhibitory activity is effective as a preventive and/or therapeutic drug for the diseases originating from excessive activation of PARP, for example, various ischemic diseases (cerebral infarction, cardiac infarction, acute renal failure, etc.), inflammatory diseases (inflammatory enteric disease, multiple cerebrosclerosis, arthritis, chronic rheumatism, etc.), nerve-degenerative diseases (Alzheimer's disease, Huntington's chorea, Parkinson disease, etc.), diabetes, septic shock, cephalic injury and the like.

There, as compounds with the PARP inhibitory activity known currently, formulae (A) to (P) listed in Table 1

TABLE 1

| Relevant Patent application | Formula |
|---|---|
|  US5756510 | 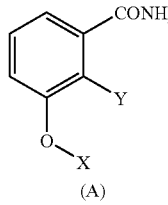<br>(A) |
|  | 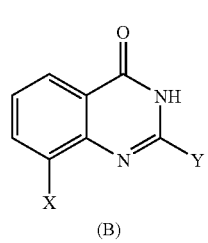<br>(B) |
|  | 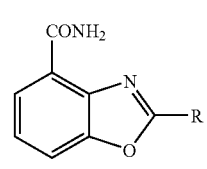<br>(C) |
| WO9704771 | 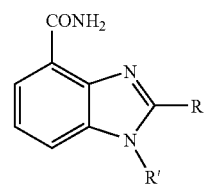<br>(D) |
| WO0121615 | 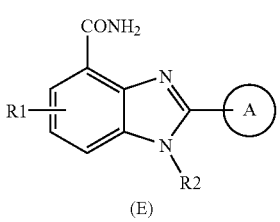<br>(E) |
|  | 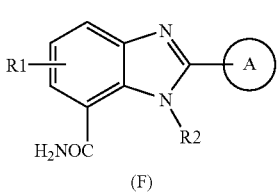<br>(F) |
| WO0029384 | 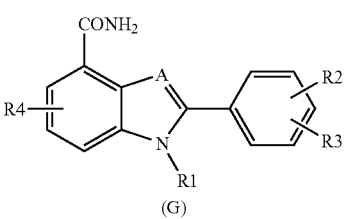<br>(G) |

TABLE 1-continued

| Relevant Patent application | Formula |
|---|---|
| WO0185687 | (H) |
| WO9959973 | (I) |
| WO0042025 | (J) |
| JP2001302669 | (K) |
| WO0179206 | (L) |
| WO0014054 | (M) |
| WO0170674 | (N) |
| | (O) |
| | (P) | are known, but all of them are not isoquinolinone derivatives and have different structure from that of the inventive compounds. Moreover, the PARP inhibitory activities disclosed cannot also be said to be sufficient.

Moreover, as compounds having the isoquinolinone structure with the PARP inhibitory activity, in Jpn. Kokai Tokkyo Koho JP 002,124,874, compounds represented by a formula (Q)

(Q)

(wherein R denotes $OR^1$, lower alkyl group, $NR^1R^2$, halogen atom, trifluoromethyl group, $COOX^2$, CN or $COX^2$ (wherein $R^1$ denotes a hydrogen atom, lower alkyl group, benzyl group, lower alkanoyl group or $(CH_2)_n(CHOH)_y(CH_2)_mA$ (wherein n denotes an integer of 1 to 4, y denotes an integer of 0 or 1, m denotes an integer of 0 to 5, A denotes $OR^2$, $N(CH_3)_2$,

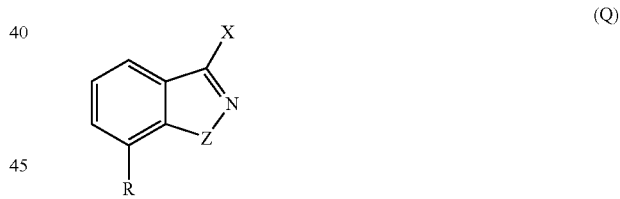

$R^2$ denotes a hydrogen atom, lower alkyl group, phenyl group or benzyl group, and $X^2$ denotes a lower alkyl group, aryl group or aralkyl group), X denotes independently $OR^1$, S-alkyl group with C1~4 or $NR^4R^5$ (wherein $R^4$ and $R^5$ denote each independently a hydrogen atom, lower alkyl group, benzyl group, lower alkanoyl group or $(CH_2)_n$ (CHOH)$_y$(CH$_2$)$_m$Q (wherein Q denotes N(CH$_3$)$_2$ or N(CH$_2$CH$_3$)$_2$)), Z denotes —CHR$^2$CHR$^3$—, —CR$^6$=CR$^3$— or —CR$^3$=N— (wherein R$^3$ denotes a hydrogen atom, alkyl group, phenyl group or benzyl group, and R$^6$ denotes a hydrogen atom, lower alkyl group, phenyl group, benzyl group, chlorine atom, bromine atom or NR$^7$R$^8$ (wherein R$^7$ and R$^8$ denote each independently a hydrogen atom or lower alkyl group)), and, when Z is —CR$^3$=N—, N in Z is bound to N on ring), are known, and, in WO9911624, compounds represented by a formula (R)

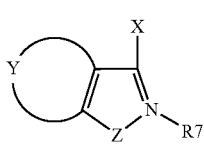

(R)

(wherein X denotes a double bond oxygen atom or hydroxy group, R$^7$ denotes a hydrogen atom or lower alkyl group, Y denotes independently an atom needed for forming monocyclic, bicyclic or tricyclic hydrocarbon ring consisting of 5- to 6-membered ring or condensed ring being a heterocycle, and Z denotes —CHR$^2$CHR$^3$— (wherein R$^2$ and R$^3$ denote each independently a hydrogen atom, alkyl group, aryl group or aralkyl group), —R$^6$C=CR$^3$— (wherein R$^3$ and R$^6$ denote each independently a hydrogen atom, lower alkyl group, aryl group, aralkyl group, halogen atom, —NO$_2$, —COOR$^7$ or —NR$^7$R$^8$ (wherein R$^8$ denotes a hydrogen atom or C$_1$~C$_9$ alkyl group), and R$^6$ and R$^3$ may constitute independently a 5- to 6-membered aromatic ring), —R$^2$C=N—, —CR$^2$ (OH) —NR$^7$ or —C(O)—NR$^7$—), are known. However, in the specifications of these patent applications, isoquinolinones with hydroxy group at 5-position and aryl group at 4-position, which is a feature of the inventive compounds, are not disclosed, and the PARP inhibitory activity of compounds disclosed in these cannot also be said to be sufficient.

Moreover, compounds represented by a formula (S) described in Table 2

TABLE 2

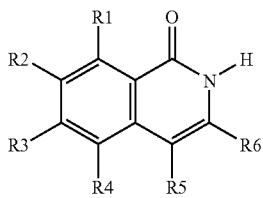

(S)

| Relevant patent application | R1, R2, R3, R4, R5 and R6 |
|---|---|
| US5516941 | R1, R2, R3, R4 and R5 denote each a hydrogen atom or nitroso group, either of R2 and R4 denotes a nitroso group, and R6 denotes a hydrogen atom. |
| WO9218123 | R1, R2, R3, R4, R5 and R6 denote each independently a hydrogen atom, hydroxy group, amino group, alkyl group, alkoxy group, cycloalkyl group, halogen atom, phenyl group or phenyl group which may be substituted with alkyl group, alkoxy group, hydroxy group or halogen atom. |
| WO9426730 | R1, R2, R3, R4 and R5 denote each independently a hydrogen atom, hydroxy group, amino group, nitroso group, nitro group, halogen atom, (C$_1$–C$_6$)alkyl group, (C$_1$–C$_6$)alkoxy group, (C$_3$–C$_7$)cycloalkyl group or phenyl group, and, among R1, R2, R3, R4 and R5, at least two |

TABLE 2-continued (S)

| Relevant patent application | R1, R2, R3, R4, R5 and R6 |
|---|---|
| | denote each a hydrogen atom, one denotes a nitro group, and R6 denotes a hydrogen atom. |
| WO9622791 | R1, R2, R3, R4 and R5 denote each independently a hydrogen atom, hydroxy group, nitroso group, nitro group, iodine atom, (C$_1$–C$_6$)alkyl group, (C$_1$–C$_6$)alkoxy group, (C$_3$–C$_7$)cycloalkyl group or phenyl group, and, among R1, R2, R3, R4 and R5, at least two denote each a hydrogen atom, one denotes a nitroso group or nitro group, and R6 denotes a hydrogen atom. |
| WO9851307 | R1, R2, R3, R4 and R5 denote each independently a hydrogen atom, hydroxy group, amino group, alkyl group, alkoxy group, cycloalky group or phenyl group which may be substituted with alkyl group, alkoxy group, hydroxy group or halogen atom, and, among R1, R2, R3, R4 and R5, at least one denotes an amino group, nitroso group or nitro group. |
| WO9851308 | R1, R2, R3, R4 and R5 denote each independently a hydrogen atom, hydroxy group, amino group, alkyl group, alkoxy group, cycloalkyl group or phenyl group which may be substituted with alkyl group, alkoxy group, hydroxy group or halogen atom, and, among R1, R2, R3, R4 and R5, at least one denotes an amino group. | are known, but the isoquinolinone derivatives disclosed in the specifications of these patent applications are only 5-nitrosoisoquinolinones, and there are no descriptions with respect to the isoquinolinone derivatives with hydroxy group at 5-position and aryl group at 4-position, which is a feature of the inventive compounds.

Furthermore, as structure-resemblant compounds with the PARP inhibitory activity, in WO0044726, compounds represented by a formula (T)

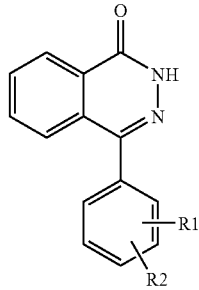

(T)

[wherein R1 denotes a C1~4 alkyl group substituted with hydroxy group or amino group, or -A1-A2-A3 (wherein A1 denotes —NR3C(O)—, —NR4C(S)—, —NR5SO$_2$— or the like, A2 denotes a C1~8 alkylene group, C2~8 alkenylene group, Cyc1 or the like, and A3 denotes a hydrogen atom, —NR17R18, Cyc2, —OR19 or the like)] (a part was extracted for the explanation of substituents), and, in WO0067734, compounds represented by a formula (U)

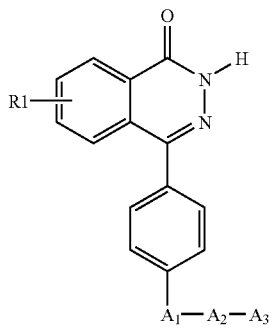

(U)

[wherein R1 denotes a hydrogen atom, halogen atom, straight chain or branched $C_1$-$C_6$-alkyl group, hydroxy group, nitro group, $CF_3$, CN, NR11R12, NH—CO—R13 or O—$C_1$-$C_4$-alkyl group (wherein R11 and R12 denote each independently a hydrogen atom or $C_1$-$C_4$-alkyl group, and R13 denotes a hydrogen atom, C1-C4-alkyl group, C1-C4-alkyl-phenyl group or phenyl group), $A_1$ denotes a straight chain or branched $C_0$—$C_6$-alkylene group, $A_2$ denotes NR2, NR2-$C_1$-$C_6$-alkyl-, O or the like, and $A_3$ denotes a 5- to 6-membered monocyclic or bicyclic aromatic ring which may have substituents or hetero aromatic ring] (a part was extracted for the explanation of substituents), are known, but all of these are phthalazinone derivatives, hence the structure is different from that of the inventive compounds being isoquinolinone derivatives. In addition, no compounds with hydroxy group at a portion corresponding to 5-position of isoquinolinone, that is, at 5-position of phthalazinone are disclosed.

Moreover, as structure-resemblant compounds of 4-substituted aryl-5-hydroxyisoquinolinone derivatives, in U.S. Pat. No. 4,897,391, as compounds with antiallergy, anti-inflammation and inhibitory effect on abnormal proliferation, compounds represented by a formula (V)

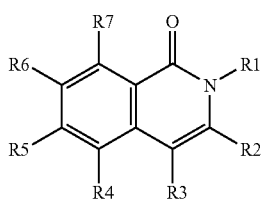

(V)

[wherein R1 denotes a hydrogen atom, alkyl group, arylmethyl group or the like, R2 denotes a hydrogen atom, alkyl group, aryl group or the like, R3 denotes a hydrogen atom, alkyl group, arylmethyl group, aryl group or the like, R4 and R6 denote each independently a hydrogen atom, halogen atom, —OR8 (wherein R8 denotes independently a hydrogen atom or alkyl group) or the like, and, between R4 and R6, at least one denotes —SH, —OH, —NHR8 or the like, and R5 and R7 denote each independently a hydrogen atom, halogen atom, —$CF_3$ or the like] (a part was extracted for the explanation of substituents), are known, but all of the compounds described in the specification of this patent application have the same substituents at 5-position and 7-position of isoquinolinone ring, and no compounds with hydroxy group only at 5-position as the inventive compounds do are disclosed. In addition, it is difficult to prepare the compounds with hydroxy group only at 5-position as the inventive compounds through the preparative process disclosed. Further, also with respect to aryl group at 4-position, only phenyl group is disclosed and phenyl group having substituents and hetero aryl group is not disclosed. Also, the PARP inhubitory activity is not described at all.

Moreover, compounds represented by a formula (W) described in Table 3

TABLE 3

(W)

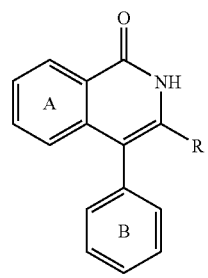

| Relevant patent application | Ring A, ring B and R | Effect |
|---|---|---|
| JP05132463 | Ring A and ring B are benzene rings which may have substituents, and R is NHCO—Y—R2. | ACAT inhibitory effect |
| JP06321906 | Ring A and ring B are benzene rings which may have substituents, and R is 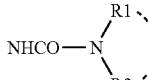 | Antagonism against tachykinin |
| JP0776573 | Ring A and ring B are benzene rings which may have substituents, and R is $(CH_2)_m$—X—CO—Y—$(CH_2)_n$—Ar. | Inhibition of calcium release, protection of cerebral ischemic disorder, anti-cerebral edema, protection of nervous disorder, antagonism against tachykinin |
| JP10298164 | Ring A and ring B are benzene rings which may have substituents, and R is —COOR3 or —CON(R4)(R5). | PDE V inhibitory effect |
| JP200072675 | Ring A and ring B are benzene rings which may have substituents, and R is —COOR3 or —CON(R4)(R5). | PDE V inhibitory effect | are known, but compounds with substituent other than hydrogen atom at 2-position and hydroxy group at 5-position as well are not disclosed in all cases, hence the structure is different from that of the inventive compounds. Alao, the PARP inhibitory activity is not described at all.

The invention is to provide a novel compound with PARP inhibitory activity, the development of which is expected as a preventive and/or therapeutic drug for the diseases originating from excessive activation of PARP, for example, various ischemic diseases (cerebral infarction, cardiac infarction, acute renal failure, etc.), inflammatory diseases (inflammatory enteric disease, multiple cerebrosclerosis, arthritis, chronic rheumatism, etc.), nerve-degenerative diseases (Alzheimer's disease, Huntington's chorea, Parkinson disease, etc.), diabetes and its complications, cephalic injury and the like.

DISCLOSURE OF THE INVENTION

As a result of diligent studies aiming at the development of a novel compound with PARP inhibitory activity, the inventors have found that 4-substituted aryl-5-hydroxyisoquinolinone derivatives and their pharmacologically acceptable addition salts have excellent PARP inhibitory effect.

Namely, according to the invention, it has been found that 4-substituted aryl-5-hydroxyisoquinolinone derivatives represented by a general formula (1)

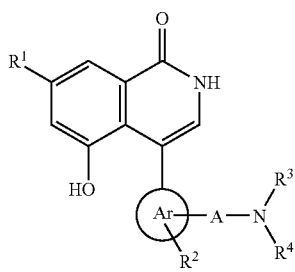

(1)

[wherein ring Ar denotes a phenyl group, naphthyl group, 5- or 6-membered heterocycle and its condensed ring, $R^1$ denotes a hydrogen atom or halogen atom, $R^2$ denotes a hydrogen atom, halogen atom, hydroxy group, lower alkyl group which may be substituted with halogen atom, cycloalkyl group which may be substituted with halogen atom, lower alkoxy group which may be substituted with halogen atom, aralkyloxy group which may have substituents, nitro group, amino group which may have substituents, aralkyl group which may have substituents, phenyl group which may have substituents, naphthyl group which may have substituents, or 5- or 6-membered heterocycle which may have substituents and its condensed ring, A denotes a $C_1$~$C_4$ alkylene or $C_2$~$C_4$ alkenylene, $R^3$ denotes a hydrogen atom, lower alkyl group which may be substituted with halogen atom, or general formula (2)

-$Q^1$-$R^5$ (2)

(wherein $Q^1$ denotes a $C_1$~$C_4$ alkylene, and $R^5$ denotes a hydroxy group, lower alkoxy group which may be substituted with halogen atom, amino group which may have substituents, lower alkoxycarbonyl group or carboxy group), $R^4$ denotes a lower alkyl group which may be substituted with halogen atom, cycloalkyl group which may have substituents, phenyl group which may have substituents, naphthyl group which may have substituents, or 5- or 6-membered heterocycle which may have substituents and its condensed ring, general formula (3)

-$Q^2$-$R^6$ (3)

(wherein $Q^2$ denotes a $C_1$~$C_4$ alkylene, and $R^6$ denotes a hydroxy group, lower alkoxy group which may be substituted with halogen atom, lower alkoxycarbonyl group, carboxy group, cycloalkyl group which may have substituents, cycloalkenyl group which may have substituents, phenyl group which may have substituents, naphthyl group which may have substituents, or 5- or 6-membered heterocycle which may have substituents and its condensed ring), or general formula (4)

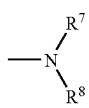

(4)

(wherein $R^7$ and $R^8$ denote identically or differently hydrogen atoms, lower alkyl groups which may be substituted with halogen atom, aralkyl groups which may have substituents, or $R^7$ and $R^8$ are bound together to form a 5- or 6-membered heterocycle which may have substituents and its condensed ring), or $R^3$ and $R^4$ are bound together to form a 5- or 6-membered heterocycle which may have substituents and its condensed ring], and their pharmacologically acceptable addition salts, and 4-substituted aryl-5-hydroxyisoquinolinone derivatives represented by a general formula (1d)

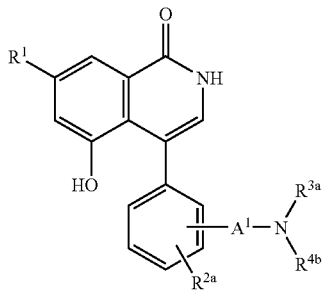

(1d)

[wherein $R^1$ denotes a hydrogen atom or halogen atom, $R^{2a}$ denotes a hydrogen atom, halogen atom, hydroxy group, lower alkyl group which may be substituted with halogen atom, lower alkoxy group which may be substituted with halogen atom, nitro group, or amino group which may have substituents, $A^1$ denotes a $C_1$~$C_4$ alkylene, $R^{3a}$ denotes a hydrogen atom or lower alkyl group which may be substituted with halogen atom, $R^{4b}$ denotes a lower alkyl group which may be substituted with halogen atom, or general formula (3a)

-$Q^2$-$R^{6a}$ (3a)

(wherein $Q^2$ denotes a $C_1$~$C_4$ alkylene, and $R^{6a}$ denotes a cycloalkyl group which may have substituents, cycloalkenyl group which may have substituents, phenyl group which may have substituents, naphthyl group which may have substituents, or 5- or 6-membered heterocycle which may have substituents and its condensed ring), or $R^{3a}$ and $R^{4b}$ are bound together to form a 5- or 6-membered heterocycle which may have substituents and its condensed ring], and their pharmacologically acceptable addition salts, have excellent PARP inhibitory effect, leading to the completion of the invention.

In the general formula (1) of the inventive compounds, preferably, compounds, ring Ar being phenyl group, $R^1$ being hydrogen atom, and A being $C_1$~$C_4$ alkylene, are mentioned. As these preferable compounds, for example, compounds listed in following Tables 4 through 12 can be mentioned, but the invention is not confined to these compounds or their pharmacologically acceptable addition salts.

TABLE 4

Structure: 1-oxo-1,2-dihydroisoquinoline with 5-OH and 4-(4-(CH₂NR³R⁴)phenyl) substituent

| No. | R³ | R⁴ |
|---|---|---|
| 1 | Me | Me |
| 2 | Et | Et |
| 3 | Pr | Pr |
| 4 | Bu | Bu |
| 5 | pentyl | pentyl |
| 6 | Me | Pr |
| 7 | Me | Bu |
| 8 | Me | pentyl |
| 9 | Me | hexyl |
| 10 | Me | Ph |
| 11 | Me | $CH_2Ph$ |
| 12 | Me | $CH_2Ph$-4-OMe |
| 13 | Me | $CH_2Ph$-3-OMe |
| 14 | Me | $CH_2Ph$-4-OH |
| 15 | Me | $CH_2Ph$-3-OH |
| 16 | Me | $CH_2Ph$-4-$NMe_2$ |
| 17 | Me | $CH_2Ph$-3-$NMe_2$ |
| 18 | Me | $CH_2Ph$-4-$NH_2$ |
| 19 | Me | $CH_2Ph$-3-$NH_2$ |
| 20 | Me | $CH_2Ph$-4-$NO_2$ |
| 21 | Me | $CH_2Ph$-3-$NO_2$ |
| 22 | Me | $CH_2Ph$-4-Cl |
| 23 | Me | $CH_2Ph$-3-Cl |
| 24 | Me | $CH_2Ph$-4-F |
| 25 | Me | $CH_2Ph$-3-F |
| 26 | Me | $CH_2Ph$-4-$CF_3$ |
| 27 | Me | $CH_2Ph$-3-$CF_3$ |
| 28 | Me | $CH_2Ph$-4-Me |
| 29 | Me | $CH_2Ph$-3-Me |
| 30 | Me | $CH_2Ph$-4-$CO_2H$ |
| 31 | Me | $CH_2Ph$-3-$CO_2H$ |
| 32 | Me | $CH_2Ph$-3,4-$(OMe)_2$ |
| 33 | Me | $CH_2Ph$-3,5-$(OMe)_2$ |
| 34 | Me | $CH_2Ph$-3,4,5-$(OMe)_3$ |
| 35 | Me | $CH_2Ph$-3,4-$F_2$ |
| 36 | Me | $CH_2Ph$-3,4-$Cl_2$ |
| 37 | Et | $CH_2Ph$ |
| 38 | $CH_2CO_2H$ | $CH_2Ph$ |
| 39 | $CH_2CH_2NMe_2$ | $CH_2Ph$ |
| 40 | $CH_2CH_2OH$ | $CH_2Ph$ |
| 41 | Me | 4-picolyl |
| 42 | Me | 3-picolyl |
| 43 | Me | 2-picolyl |
| 44 | Me | $CH_2$-1-naphthyl |
| 45 | Me | $CH_2$-2-naphthyl |
| 46 | $CH_2CH_2OH$ | $CH_2CH_2OH$ |

TABLE 5

Structure: 1-oxo-1,2-dihydroisoquinoline with 5-OH and 4-(3-(CH₂NR³R⁴)phenyl) substituent

| No. | R³ | R⁴ |
|---|---|---|
| 1 | Me | Me |
| 2 | Et | Et |
| 3 | Pr | Pr |
| 4 | Bu | Bu |
| 5 | pentyl | pentyl |
| 6 | Me | Pr |
| 7 | Me | Bu |
| 8 | Me | pentyl |
| 9 | Me | hexyl |
| 10 | Me | Ph |
| 11 | Me | $CH_2Ph$ |
| 12 | Me | $CH_2Ph$-4-OMe |
| 13 | Me | $CH_2Ph$-3-OMe |
| 14 | Me | $CH_2Ph$-4-OH |
| 15 | Me | $CH_2Ph$-3-OH |
| 16 | Me | $CH_2Ph$-4-$NMe_2$ |
| 17 | Me | $CH_2Ph$-3-$NMe_2$ |
| 18 | Me | $CH_2Ph$-4-$NH_2$ |
| 19 | Me | $CH_2Ph$-3-$NH_2$ |
| 20 | Me | $CH_2Ph$-4-$NO_2$ |
| 21 | Me | $CH_2Ph$-3-$NO_2$ |
| 22 | Me | $CH_2Ph$-4-Cl |
| 23 | Me | $CH_2Ph$-3-Cl |
| 24 | Me | $CH_2Ph$-4-F |
| 25 | Me | $CH_2Ph$-3-F |
| 26 | Me | $CH_2Ph$-4-$CF_3$ |
| 27 | Me | $CH_2Ph$-3-$CF_3$ |
| 28 | Me | $CH_2Ph$-4-Me |
| 29 | Me | $CH_2Ph$-3-Me |
| 30 | Me | $CH_2Ph$-4-$CO_2H$ |
| 31 | Me | $CH_2Ph$-3-$CO_2H$ |
| 32 | Me | $CH_2Ph$-3,4-$(OMe)_2$ |
| 33 | Me | $CH_2Ph$-3,5-$(OMe)_2$ |
| 34 | Me | $CH_2Ph$-3,4,5-$(OMe)_3$ |
| 35 | Me | $CH_2Ph$-3,4-$F_2$ |
| 36 | Me | $CH_2Ph$-3,4-$Cl_2$ |
| 37 | Et | $CH_2Ph$ |
| 38 | $CH_2CO_2H$ | $CH_2Ph$ |
| 39 | $CH_2CH_2NMe_2$ | $CH_2Ph$ |
| 40 | $CH_2CH_2OH$ | $CH_2Ph$ |
| 41 | Me | 4-picolyl |
| 42 | Me | 3-picolyl |
| 43 | Me | 2-picolyl |
| 44 | Me | $CH_2$-1-naphthyl |
| 45 | Me | $CH_2$-2-naphthyl |
| 46 | $CH_2CH_2OH$ | $CH_2CH_2OH$ |

TABLE 6

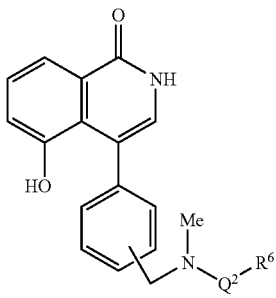

| No. | position | Q² | R⁶ |
|---|---|---|---|
| 1 | 4 | $CH_2$ | cyclopentyl |
| 2 | 4 | $CH_2$ | cyclohexyl |
| 3 | 4 | $CH_2$ | cyclohexen-1-yl |
| 4 | 4 | $(CH_2)_2$ | cyclopentyl |
| 5 | 4 | $(CH_2)_2$ | cyclohexyl |
| 6 | 4 | $(CH_2)_2$ | cyclohexen-1-yl |
| 7 | 4 | $(CH_2)_2$ | Ph |
| 8 | 4 | $(CH_2)_2$ | Ph-4-OMe |
| 9 | 4 | $(CH_2)_2$ | Ph-4-OH |
| 10 | 4 | $(CH_2)_2$ | Ph-4-NMe$_2$ |
| 11 | 4 | $(CH_2)_2$ | Ph-4-NH$_2$ |
| 12 | 4 | $(CH_2)_2$ | Ph-4-NO$_2$ |
| 13 | 4 | $(CH_2)_2$ | Ph-4-Cl |
| 14 | 4 | $(CH_2)_2$ | Ph-4-F |
| 15 | 4 | $(CH_2)_2$ | Ph-4-CF$_3$ |
| 16 | 4 | $(CH_2)_2$ | Ph-4-Me |
| 17 | 4 | $(CH_2)_2$ | Ph-4-CO$_2$H |
| 18 | 4 | $(CH_2)_2$ | 4-pyridyl |
| 19 | 4 | $(CH_2)_2$ | 3-pyridyl |
| 20 | 4 | $(CH_2)_2$ | 2-pyridyl |
| 21 | 4 | $(CH_2)_2$ | 1-naphthyl |
| 22 | 4 | $(CH_2)_2$ | 2-naphthyl |
| 23 | 4 | $(CH_2)_3$ | cyclohexyl |
| 24 | 4 | $(CH_2)_3$ | Ph |
| 25 | 4 | $(CH_2)_3$ | Ph-4-OMe |
| 26 | 4 | $(CH_2)_3$ | Ph-4-OH |
| 27 | 4 | $(CH_2)_3$ | Ph-4-NMe$_2$ |
| 28 | 4 | $(CH_2)_3$ | Ph-4-NH$_2$ |
| 29 | 4 | $(CH_2)_3$ | Ph-4-NO$_2$ |
| 30 | 4 | $(CH_2)_3$ | Ph-4-Cl |
| 31 | 4 | $(CH_2)_3$ | Ph-4-CO$_2$H |
| 32 | 4 | $(CH_2)_3$ | 4-pyridyl |
| 33 | 4 | $(CH_2)_3$ | 2-naphthyl |
| 34 | 4 | $(CH_2)_4$ | cyclohexyl |
| 35 | 4 | $(CH_2)_4$ | Ph |
| 36 | 4 | $(CH_2)_4$ | Ph-4-OMe |
| 37 | 4 | $(CH_2)_4$ | Ph-4-NMe$_2$ |
| 38 | 4 | $(CH_2)_4$ | Ph-4-NH$_2$ |
| 39 | 4 | $(CH_2)_4$ | Ph-4-NO$_2$ |
| 40 | 4 | $(CH_2)_4$ | 4-pyridyl |
| 41 | 4 | $(CH_2)_4$ | 2-naphthyl |
| 42 | 3 | $CH_2$ | cyclohexyl |
| 43 | 3 | $CH_2$ | Ph |
| 44 | 3 | $CH_2$ | Ph-4-OMe |
| 45 | 3 | $CH_2$ | Ph-4-NMe$_2$ |
| 46 | 3 | $CH_2$ | Ph-4-NH$_2$ |
| 47 | 3 | $(CH_2)_2$ | cyclohexyl |
| 48 | 3 | $(CH_2)_2$ | cyclohexen-1-yl |
| 49 | 3 | $(CH_2)_2$ | Ph |
| 50 | 3 | $(CH_2)_2$ | Ph-4-OMe |
| 51 | 3 | $(CH_2)_2$ | Ph-4-NMe$_2$ |
| 52 | 3 | $(CH_2)_2$ | Ph-4-NH$_2$ |
| 53 | 3 | $(CH_2)_3$ | cyclohexyl |
| 54 | 3 | $(CH_2)_3$ | Ph |
| 55 | 3 | $(CH_2)_3$ | Ph-4-OMe |
| 56 | 3 | $(CH_2)_3$ | Ph-4-NMe$_2$ |
| 57 | 3 | $(CH_2)_3$ | Ph-4-NH$_2$ |
| 58 | 3 | $(CH_2)_4$ | cyclohexyl |
| 59 | 3 | $(CH_2)_4$ | Ph |
| 60 | 3 | $(CH_2)_4$ | Ph-4-OMe |
| 61 | 3 | $(CH_2)_4$ | Ph-4-NMe$_2$ |
| 62 | 3 | $(CH_2)_4$ | Ph-4-NH$_2$ |

TABLE 7

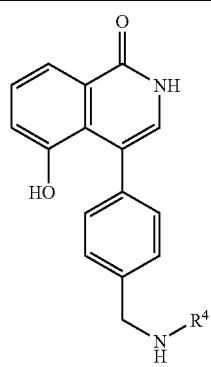

| No. | R⁴ |
|---|---|
| 1 | Me |
| 2 | Et |
| 3 | Pr |
| 4 | Bu |
| 5 | pentyl |
| 6 | hexyl |
| 7 | Ph |
| 8 | $CH_2CO_2H$ |
| 9 | $CH_2CH_2CO_2H$ |
| 10 | $CH_2OH$ |
| 11 | $CH_2CH_2NEt_2$ |
| 12 | $CH_2$-cyclohexyl |
| 13 | $CH_2Ph$ |
| 14 | $CH_2Ph$-4-OMe |
| 15 | $CH_2Ph$-3-OMe |
| 16 | $CH_2Ph$-4-OH |
| 17 | $CH_2Ph$-3-OH |
| 18 | $CH_2Ph$-4-NMe$_2$ |
| 19 | $CH_2Ph$-3-NMe$_2$ |
| 20 | $CH_2Ph$-4-NH$_2$ |
| 21 | $CH_2Ph$-3-NH$_2$ |
| 22 | $CH_2Ph$-4-NO$_2$ |
| 23 | $CH_2Ph$-3-NO$_2$ |
| 24 | $CH_2Ph$-4-Cl |
| 25 | $CH_2Ph$-3-Cl |
| 26 | $CH_2Ph$-4-F |
| 27 | $CH_2Ph$-3-F |
| 28 | $CH_2Ph$-4-CF$_3$ |
| 29 | $CH_2Ph$-3-CF$_3$ |
| 30 | $CH_2Ph$-4-Me |
| 31 | $CH_2Ph$-3-Me |
| 32 | $CH_2Ph$-4-CO$_2$H |
| 33 | $CH_2Ph$-3-CO$_2$H |
| 34 | $CH_2Ph$-3,4-(OMe)$_2$ |
| 35 | $CH_2Ph$-3,5-(OMe)$_2$ |
| 36 | $CH_2Ph$-3,4,5-(OMe)$_3$ |
| 37 | $CH_2Ph$-3,4-F$_2$ |
| 38 | $CH_2Ph$-3,4-Cl$_2$ |
| 39 | 4-picolyl |
| 40 | 3-picolyl |
| 41 | 2-picolyl |
| 42 | $CH_2$-1-naphthyl |
| 43 | $CH_2$-2-naphthyl |
| 44 | $CH_2CH_2$-cyclohexyl |
| 45 | $CH_2CH_2$-cyclohexen-1-yl |
| 46 | $CH_2CH_2Ph$ |
| 47 | $CH_2CH_2Ph$-4-OMe |
| 48 | $CH_2CH_2Ph$-4-OH |
| 49 | $CH_2CH_2CH_2Ph$ |
| 50 | $CH_2CH_2CH_2CH_2Ph$ |

TABLE 8

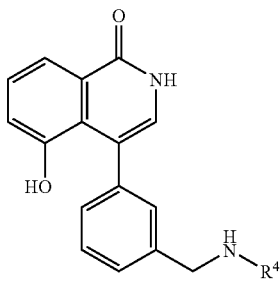

| No. | R⁴ |
|---|---|
| 1 | Me |
| 2 | Et |
| 3 | Pr |
| 4 | Bu |
| 5 | pentyl |
| 6 | hexyl |
| 7 | Ph |
| 8 | $CH_2CO_2H$ |
| 9 | $CH_2CH_2CO_2H$ |
| 10 | $CH_2CH_2OH$ |
| 11 | $CH_2CH_2NEt_2$ |
| 12 | $CH_2$-cyclohexyl |
| 13 | $CH_2Ph$ |
| 14 | $CH_2Ph$-4-OMe |
| 15 | $CH_2Ph$-3-OMe |
| 16 | $CH_2Ph$-4-OH |
| 17 | $CH_2Ph$-3-OH |
| 18 | $CH_2Ph$-4-$NMe_2$ |
| 19 | $CH_2Ph$-3-$NMe_2$ |
| 20 | $CH_2Ph$-4-$NH_2$ |
| 21 | $CH_2Ph$-3-$NH_2$ |
| 22 | $CH_2Ph$-4-$NO_2$ |
| 23 | $CH_2Ph$-3-$NO_2$ |
| 24 | $CH_2Ph$-4-Cl |
| 25 | $CH_2Ph$-3-Cl |
| 26 | $CH_2Ph$-4-F |
| 27 | $CH_2Ph$-3-F |
| 28 | $CH_2Ph$-4-$CF_3$ |
| 29 | $CH_2Ph$-3-$CF_3$ |
| 30 | $CH_2Ph$-4-Me |
| 31 | $CH_2Ph$-3-Me |
| 32 | $CH_2Ph$-4-$CO_2H$ |
| 33 | $CH_2Ph$-3-$CO_2H$ |
| 34 | $CH_2Ph$-3,4-$(OMe)_2$ |
| 35 | $CH_2Ph$-3,5-$(OMe)_2$ |
| 36 | $CH_2Ph$-3,4,5-$(OMe)_3$ |
| 37 | $CH_2$-3,4-$F_2$ |
| 38 | $CH_2Ph$-3,4-$Cl_2$ |
| 39 | 4-picolyl |
| 40 | 3-picolyl |
| 41 | 2-picolyl |
| 42 | $CH_2$-1-naphthyl |
| 43 | $CH_2$-2-naphthyl |
| 44 | $CH_2CH_2$-cyclohexyl |
| 45 | $CH_2CH_2$-cyclohexen-1-yl |
| 46 | $CH_2CH_2Ph$ |
| 47 | $CH_2CH_2Ph$-4-OMe |
| 48 | $CH_2CH_2Ph$-4-OH |
| 49 | $CH_2CH_2CH_2Ph$ |
| 50 | $CH_2CH_2CH_2CH_2Ph$ |

TABLE 9

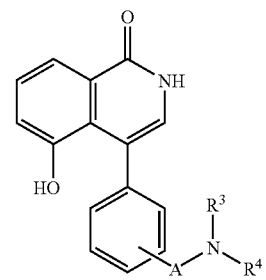

| No. | position | A | NR³R⁴ |
|---|---|---|---|
| 1 | 4 | $(CH_2)_2$ | $NMe_2$ |
| 2 | 4 | $(CH_2)_2$ | $NPr_2$ |
| 3 | 4 | $(CH_2)_2$ | N(Me)Pr |
| 4 | 4 | $(CH_2)_2$ | N(Me)pentyl |
| 5 | 4 | $(CH_2)_2$ | $N(Me)(CH_2)_2NMe_2$ |
| 6 | 4 | $(CH_2)_2$ | $N(Me)CH_2$-cyclohexyl |
| 7 | 4 | $(CH_2)_2$ | $N(Me)CH_2Ph$ |
| 8 | 4 | $(CH_2)_2$ | $N(Me)CH_2Ph$-4-OMe |
| 9 | 4 | $(CH_2)_2$ | $N(Me)CH_2Ph$-3-OMe |
| 10 | 4 | $(CH_2)_2$ | $N(Me)CH_2Ph$-4-OH |
| 11 | 4 | $(CH_2)_2$ | $N(Me)CH_2Ph$-3-OH |
| 12 | 4 | $(CH_2)_2$ | $N(Me)CH_2Ph$-4-$NH_2$ |
| 13 | 4 | $(CH_2)_2$ | $N(Me)CH_2Ph$-4-$NMe_2$ |
| 14 | 4 | $(CH_2)_2$ | $N(Me)(CH_2)_2$-cyclohexenyl |
| 15 | 4 | $(CH_2)_2$ | $N(Me)(CH_2)_2Ph$ |
| 16 | 4 | $(CH_2)_2$ | $N(Me)(CH_2)_2Ph$-4-OMe |
| 17 | 4 | $(CH_2)_2$ | $N(Me)(CH_2)_2Ph$-4-OH |
| 18 | 4 | $(CH_2)_2$ | $N(Me)(CH_2)_2Ph$-4-$NH_2$ |
| 19 | 4 | $(CH_2)_2$ | $N(Me)(CH_2)_2Ph$-4-$NMe_2$ |
| 20 | 4 | $(CH_2)_3$ | $NMe_2$ |
| 21 | 4 | $(CH_2)_3$ | $NPr_2$ |
| 22 | 4 | $(CH_2)_3$ | $N(Me)(CH_2)_2NMe_2$ |
| 23 | 4 | $(CH_2)_3$ | $N(Me)CH_2Ph$ |
| 24 | 4 | $(CH_2)_3$ | $N(Me)CH_2Ph$-4-OMe |
| 25 | 4 | $(CH_2)_3$ | $N(Me)CH_2Ph$-4-$NMe_2$ |
| 26 | 4 | $(CH_2)_3$ | $N(Me)(CH_2)_2Ph$ |
| 27 | 4 | $(CH_2)_3$ | $N(Me)(CH_2)_2Ph$-4-OMe |
| 28 | 3 | $(CH_2)_2$ | $NMe_2$ |
| 29 | 3 | $(CH_2)_2$ | $NPr_2$ |
| 30 | 3 | $(CH_2)_2$ | N(Me)Pr |
| 31 | 3 | $(CH_2)_2$ | $N(Me)CH_2$-cyclohexyl |
| 32 | 3 | $(CH_2)_2$ | $N(Me)CH_2Ph$ |
| 33 | 3 | $(CH_2)_2$ | $N(Me)CH_2Ph$-4-OMe |
| 34 | 3 | $(CH_2)_2$ | $N(Me)(CH_2)_2$-cyclohexenyl |
| 35 | 3 | $(CH_2)_2$ | $N(Me)(CH_2)_2Ph$ |
| 36 | 3 | $(CH_2)_3$ | $NMe_2$ |
| 37 | 3 | $(CH_2)_3$ | $N(Me)CH_2Ph$ |
| 38 | 3 | $(CH_2)_3$ | $N(Me)(CH_2)_2Ph$ |

TABLE 10

Structure: 4-(4-substituted-phenyl)-5-hydroxyisoquinolin-1(2H)-one with substituent -A-NR³R⁴ on para position of phenyl

| No. | A | NR³R⁴ |
|---|---|---|
| 1 | CH₂ | pyrrolidin-1-yl |
| 2 | CH₂ | piperidin-1-yl |
| 3 | CH₂ | morpholin-4-yl |
| 4 | CH₂ | piperazin-1-yl |
| 5 | CH₂ | 4-methylpiperazin-1-yl |
| 6 | CH₂ | 4-phenylpiperazin-1-yl |
| 7 | CH₂ | 4-benzylpiperazin-1-yl |
| 8 | CH₂ | 3-(pyrrolidin-1-yl)piperidin-1-yl |
| 9 | CH₂ | [1,4'-bipiperidin]-1'-yl |
| 10 | CH₂ | 4-phenyl-3,6-dihydro-2H-pyridin-1-yl |
| 11 | CH₂ | 4-(4-methoxyphenyl)-3,6-dihydro-2H-pyridin-1-yl |
| 12 | CH₂ | 4-(4-hydroxyphenyl)-3,6-dihydro-2H-pyridin-1-yl |
| 13 | CH₂ | 4-(4-dimethylaminophenyl)-3,6-dihydro-2H-pyridin-1-yl |
| 14 | CH₂ | 4-benzyl-3,6-dihydro-2H-pyridin-1-yl |
| 15 | CH₂ | 4-benzyl-4-hydroxypiperidin-1-yl |
| 16 | CH₂ | 2-methyl-1,2,3,4-tetrahydroisoquinolin-2-yl |
| 17 | (CH₂)₂ | pyrrolidin-1-yl |
| 18 | (CH₂)₂ | piperidin-1-yl |
| 19 | (CH₂)₂ | 4-benzylpiperazin-1-yl |
| 20 | (CH₂)₂ | 4-phenyl-3,6-dihydro-2H-pyridin-1-yl |
| 21 | (CH₂)₂ | 2-methyl-1,2,3,4-tetrahydroisoquinolin-2-yl |
| 22 | (CH₂)₃ | pyrrolidin-1-yl |
| 23 | (CH₂)₃ | piperidin-1-yl |

TABLE 10-continued

[Structure: 5-hydroxy-4-(4-substituted-phenyl)isoquinolin-1(2H)-one with A-NR³R⁴ substituent at para position]

| No. | A | NR³R⁴ |
|---|---|---|
| 24 | (CH₂)₃ | piperazine N-benzyl |
| 25 | (CH₂)₃ | 4-phenyl-1,2,3,6-tetrahydropyridine |
| 26 | (CH₂)₃ | 2-methyl-1,2,3,4-tetrahydroisoquinolin-2-yl |

TABLE 11

[Structure: 5-hydroxy-4-(3-substituted-phenyl)isoquinolin-1(2H)-one with A-NR³R⁴ substituent at meta position]

| No. | A | NR³R⁴ |
|---|---|---|
| 1 | CH₂ | pyrrolidin-1-yl |
| 2 | CH₂ | piperidin-1-yl |
| 3 | CH₂ | morpholin-4-yl |
| 4 | CH₂ | piperazin-1-yl (NH) |
| 5 | CH₂ | 4-methylpiperazin-1-yl |
| 6 | CH₂ | 4-phenylpiperazin-1-yl |
| 7 | CH₂ | 4-benzylpiperazin-1-yl |
| 8 | CH₂ | 4-(pyrrolidin-1-yl)piperidin-1-yl |
| 9 | CH₂ | 4-(piperidin-1-yl)piperidin-1-yl |
| 10 | CH₂ | 4-phenyl-1,2,3,6-tetrahydropyridin-1-yl |
| 11 | CH₂ | 4-(4-methoxyphenyl)-1,2,3,6-tetrahydropyridin-1-yl |
| 12 | CH₂ | 4-(4-hydroxyphenyl)-1,2,3,6-tetrahydropyridin-1-yl |
| 13 | CH₂ | 4-(4-dimethylaminophenyl)-1,2,3,6-tetrahydropyridin-1-yl |
| 14 | CH₂ | 4-benzyl-1,2,3,6-tetrahydropyridin-1-yl |
| 15 | CH₂ | 4-hydroxy-4-benzylpiperidin-1-yl |
| 16 | CH₂ | 2-methyl-1,2,3,4-tetrahydroisoquinolin-2-yl |

TABLE 11-continued

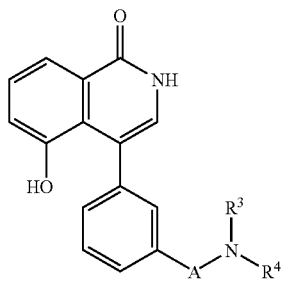

| No. | A | NR³R⁴ |
|---|---|---|
| 17 | (CH₂)₂ | pyrrolidin-1-yl |
| 18 | (CH₂)₂ | piperidin-1-yl |
| 19 | (CH₂)₂ | 4-benzylpiperazin-1-yl |
| 20 | (CH₂)₂ | 4-phenyl-1,2,3,6-tetrahydropyridin-1-yl |
| 21 | (CH₂)₂ | 2-methyl-1,2,3,4-tetrahydroisoquinolin-2-yl |
| 22 | (CH₂)₃ | pyrrolidin-1-yl |
| 23 | (CH₂)₃ | piperidin-1-yl |
| 24 | (CH₂)₃ | 4-benzylpiperazin-1-yl |
| 25 | (CH₂)₃ | 4-phenyl-1,2,3,6-tetrahydropyridin-1-yl |
| 26 | (CH₂)₃ | 2-methyl-1,2,3,4-tetrahydroisoquinolin-2-yl |

TABLE 12

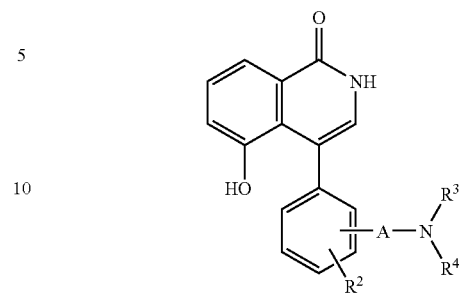

| No. | R² | A—NR³R⁴ |
|---|---|---|
| 1 | 4-OMe | 3-(CH₂NMe₂) |
| 2 | 4-OMe | 3-(CH₂NPr₂) |
| 3 | 4-OMe | 3-(CH₂N(Me)Pr) |
| 4 | 4-OMe | 3-(CH₂N(Me)CH₂-cyclohexyl) |
| 5 | 4-OMe | 3-(CH₂N(Me)CH₂Ph) |
| 6 | 4-OMe | 3-(CH₂N(Me)(CH₂)₂Ph) |
| 7 | 4-OH | 3-(CH₂NMe₂) |
| 8 | 4-OH | 3-(CH₂NPr₂) |
| 9 | 4-OH | 3-(CH₂N(Me)Pr) |
| 10 | 4-OH | 3-(CH₂N(Me)CH₂-cyclohexyl) |
| 11 | 4-OH | 3-(CH₂N(Me)CH₂Ph) |
| 12 | 4-OH | 3-(CH₂N(Me)(CH₂)₂Ph) |
| 13 | 4-F | 3-(CH₂NMe₂) |
| 14 | 4-F | 3-(CH₂NPr₂) |
| 15 | 4-F | 3-(CH₂N(Me)Pr) |
| 16 | 4-F | 3-(CH₂N(Me)CH₂-cyclohexyl) |
| 17 | 4-F | 3-(CH₂N(Me)CH₂Ph) |
| 18 | 4-F | 3-(CH₂N(Me)(CH₂)₂Ph) |
| 19 | 3-NO₂ | 4-((CH₂)₂NMe₂) |
| 20 | 3-NO₂ | 4-((CH₂)₂NPr₂) |
| 21 | 3-NO₂ | 4-((CH₂)₂N(Me)Pr) |
| 22 | 3-NO₂ | 4-((CH₂)₂N(Me)CH₂-cyclohexyl) |
| 23 | 3-NO₂ | 4-((CH₂)₂N(Me)CH₂Ph) |
| 24 | 3-NO₂ | 4-((CH₂)₂N(Me)(CH₂)₂Ph) |
| 25 | 3-NH₂ | 4-((CH₂)₂NMe₂) |
| 26 | 3-NH₂ | 4-((CH₂)₂NPr₂) |
| 27 | 3-NH₂ | 4-((CH₂)₂N(Me)Pr) |
| 28 | 3-NH₂ | 4-((CH₂)₂N(Me)CH₂-cyclohexyl) |
| 29 | 3-NH₂ | 4-((CH₂)₂N(Me)CH₂Ph) |
| 30 | 3-NH₂ | 4-((CH₂)₂N(Me)(CH₂)₂Ph) |

In Tables 4 through 12 aforementioned, as more preferable compounds, exemplified nos. 1 to 12, 14, 16, 18, 37 to 39, 42 and 44 described in Table 4, exemplified nos. 1 to 3 described in Table 5, exemplified nos. 2, 6 to 9, and 24 described in Table 6, exemplified nos. 2, 3, 8, 9, 11 to 18, 20, 22, 24, 32, 34, 36, 39, 40 and 48 described in Table 7, exemplified nos. 1 to 17, 20 to 22, 24, 25 and 27 to 29 described in Table 9, exemplified nos. 1 to 4, 6, 7, 9, 10, 14 to 16, 19 to 21 and 24 described in Table 10, exemplified nos. 1 and 2 described in Table 11, and exemplified nos. 2, 8, 19 and 25 described in Table 12 can be mentioned.

In the description of the general formula (1) of the invention, for "halogen atoms" in "lower alkyl group which may be substituted with halogen atom", "cycloalkyl group which may be substituted with halogen atom" and "lower alkoxy group which may be substituted with halogen atom", fluorine, chlorine, bromine and iodine are mentioned, for "lower alkyl groups", straight chain or branched ones with carbon atoms of 1 to 6 such as methyl, ethyl, n-propyl and iso-propyl are mentioned, for "cycloalkyl groups", ones with carbon atoms of 3 to 7 such as cyclopropyl, cyclopentyl and cyclohexyl are mentioned, and, for "lower alkoxy groups", straight chain or branched ones with carbon atoms of 1 to 5 such as methoxy, ethoxy and propoxy are mentioned. Moreover, in the text, for substituents in "cycloalkyl group which may have substituents", "cycloalkenyl group which may have substituents", "aralkyl group which may have substituents", "aralkyloxy group which may have substituents", "phenyl group which may have substituents", "naphthyl group which may have substituents", and "5- or 6-membered heterocycle which may have substituents and its condensed ring", halogen atom, hydroxy group, lower alkyl group which may be substituted with halogen atom, lower alkoxy group which may be substituted with halogen atom, lower alkylthio group, lower alkoxycarbonyl group, nitro group, amino group which may have substituents, cyano group, carboxy group, aldehyde group, lower alkyl group substituted with hydroxy group, lower alkyl group substituted with carboxy group, lower alkyl group substituted with amino group, which may be substituted with lower alkyl group which may be substituted with halogen atom or aralkyl group which may have substituents, lower alkyl group substituted with 5- or 6-membered cycloamino group which may have substituents, lower alkoxy group substituted with hydroxy group, lower alkoxy group substituted with carboxy group, lower alkoxy group substituted with amino group, which may be substituted with lower alkyl group which may be substituted with halogen atom or aralkyl group which may have substituents, lower alkoxy group substituted with 5- or 6-membered cycloamino group which may have substituents, aralkyl group which may have substituents, phenyl group which may have substituents, naphthyl group which may have substituents, 5- or 6-membered heterocycle group which may have substituents, etc. are mentioned, for "lower alkoxycarbonyl groups", straight chain or branched ones with carbon atoms of 1 to 6 such as methoxycarbonyl and ethoxycarbonyl, for "amino groups which may have substituents", amino groups, which may be substituted with acyl group, lower alkylsulfonyl group which may be substituted with halogen atom or arylsulfonyl group, for example, with acetyl, methanesulfonyl, phenylsulfonyl or the like, or which may be substituted with lower alkyl group which may be substituted with halogen atom, phenyl group which may have substituents and aralkyl group which may have substituents, are mentioned, for "5- or 6-membered cycloamino groups" in "5- or 6-membered cycloamino group which may have substituents", pyrrolidyl, piperidyl, piperazyl, morpholyl, thiomorpholyl, etc. are mentioned, for "cycloalkenyl groups" in "cycloalkenyl group which may have substituents", ones with carbon atoms of 5 to 7 such as cyclopentenyl and cyclohexenyl are mentioned, and, for "aralkyl groups" in "aralkyl group which may have substituents" and "aralkyloxy group which may have substituents", benzyl, diphenylmethyl, phenethyl, phenylpropyl, etc. are mentioned. The substituents referred to so here indicate "substituents" as explained above. Moreover, "heterocycles" in "5- or 6-membered heterocycle and its condensed ring" are saturated or unsaturated monocyclic or polycyclic heterocycle groups which may have substituents and which can contain one or more nitrogen, oxygen or sulfur atoms, and, for example, pyrrolidyl, piperidyl, piperazyl, morpholyl, thiomorpholyl, tetrahydropyridyl, furanyl, thienyl, pyrazolyl, imidazolyl, oxazolyl, thiazolyl, pyridyl, pyrimidyl, pyridazyl, pyrazyl, etc. are mentioned, and "its condensed ring" indicates benzene-condensed rings of said "heterocycles" (for example, indolyl, tetrahydroquinolyl, benzoxazolidinyl, benzothiazolidinyl, benzofuranyl, benzothienyl, benzimidazolyl, quinolyl, tetrahydroquinolyl, isoquinolyl, tetrahydroisoquinolyl, quinazolyl, quinoxalyl, cinnolyl, etc. are mentioned), or condensed rings consisting of two rings selected arbitrarily from said "heterocycles" (for example, imidazopyridine, pyrazolopyridine, imidazopyrimidine, etc. are mentioned).

The compounds represented by the general formula (1) of the invention can be converted to pharmacologically acceptable salts, if need be. For the pharmacologically acceptable salts, for example, salts with inorganic acids such as hydrochloric acid, hydrobromic acid and sulfuric acid, salts with organic acids such as acetic acid, fumaric acid, maleic acid, oxalic acid, citric acid, methanesulfonic acid and tosylic acid, and salts with bases such as sodium salt, potassium salt, calcium salt and ammonium salt are mentioned.

Moreover, the compounds represented by the general formula (1) and their pharmacologically acceptable salts of the invention may be their intramolecular salts, their anhydrides, hydrates or solvates.

The compounds with PARP inhibitory activity of the invention represented by the general formula (1) can be prepared through processes shown below, or in combination of publicly known processes.

[Preparative process I]

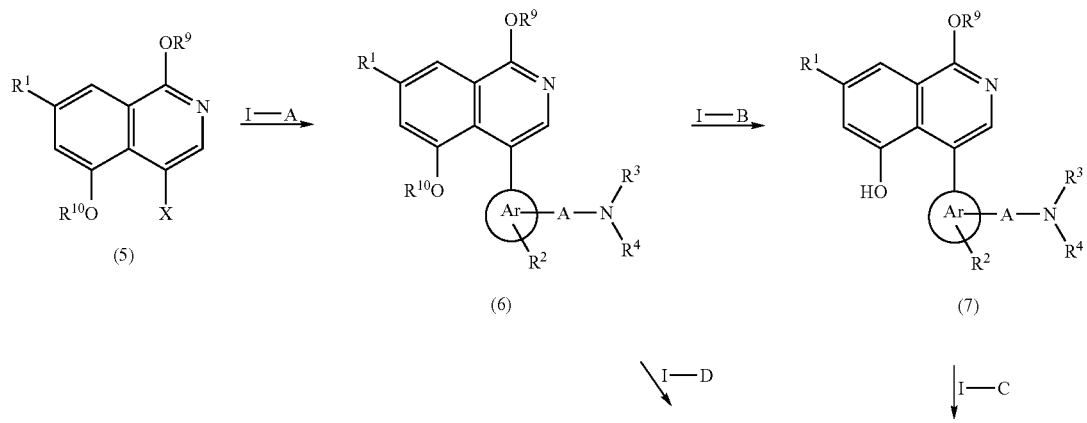

-continued

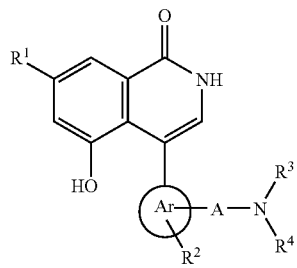

(1)

In said formulae, ring Ar, A, $R^1$, $R^2$, $R^3$ and $R^4$ denote the same meanings as described above, $R^9$ denotes a lower alkyl group which may be substituted with halogen atom or aralkyl group which may have substituents, $R^{10}$ denotes a lower alkyl group which may be substituted with halogen atom, aralkyl group which may have substituents or acyl group, and X denotes a halogen atom.

The conversion from compounds represented by the general formula (5) to compounds represented by the general formula (6) (process I-A) can be performed by using compounds represented by a general formula (8)

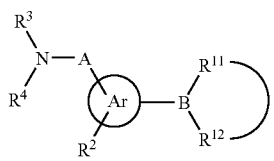

(8)

(wherein ring Ar, A, $R^2$, $R^3$ and $R^4$ denote the same meanings as described above, $R^{11}$ and $R^{12}$ denote identically or differently hydroxy groups, lower alkyl groups or lower alkoxy groups, or $R^{11}$ and $R^{12}$ may be bound together to form a 5- or 6-membered cyclic pinacol ester which may be substituted with lower alkyl group), and by reacting for 1 to 48 hours at 20 to 160° C. in a suitable solvent, for example, tetrahydrofuran, N,N-dimethylformamide, benzene, toluene, mixed solvent thereof or the like in the presence of a suitable catalyst, for example, tetrakis(triphenylphosphine)palladium(0), bis(triphenylphosphine)palladium(II) chloride, (1,1'-bis(diphenylphosphino)ferrocene)palladium(II) chloride or the like, after adding a suitable base, for example, sodium hydroxide, sodium carbonate, potassium carbonate, sodium hydrogencarbonate, triethylamine, N,N-diisopropylethylamine or the like.

Compounds, $R^{10}$ being acyl group, among compounds represented by the general formula (6) can be converted to compounds represented by the general formula (7) (process I-B). Namely, the conversion can be performed by using a suitable base, for example, sodium hydroxide, potassium hydroxide, lithium hydroxide, potassium carbonate, sodium hydrogencarbonate, ammonia or the like, and by reacting for 0.5 to 24 hours at 0 to 100° C. in a suitable solvent, for example, water, methanol, ethanol, tetrahydrofuran, 1,4-dioxane, mixed solvent thereof or the like.

The conversion from compounds represented by the general formula (7) to compounds represented by the general formula (1) (process I-C) can be performed by using a suitable acid, for example, hydrochloric acid, hydrobromic acid, sulfuric acid, trifluoroacetic acid or the like, or a suitable dealkylating agent, for example, trimethylsilyl iodide, boron tribromide or the like, and by reacting for 1 to 72 hours at 20 to 120° C. without solvent or in a suitable solvent, for example, water, acetic acid, methanol, dichloromethane, mixed solvent thereof or the like.

Moreover, compounds, $R^{10}$ being lower alkyl group which may be substituted with halogen atom or aralkyl group which may have substituents, among compounds represented by the general formula (6) can be converted directly to compounds represented by the general formula (1) (process I-D). Namely, the conversion can be performed by using a suitable acid, for example, hydrochloric acid, hydrobromic acid, sulfuric acid, trifluoroacetic acid or the like, or a suitable dealkylating agent, for example, trimethylsilyl iodide, boron tribromide or the like, and by reacting for 1 to 72 hours at 20 to 120° C. without solvent or in a suitable solvent, for example, water, acetic acid, methanol, dichloromethane, mixed solvent thereof or the like. Also, it is possible to react these suitable acid and suitable dealkylating agent over twice stepwise.

[Preparative process II]

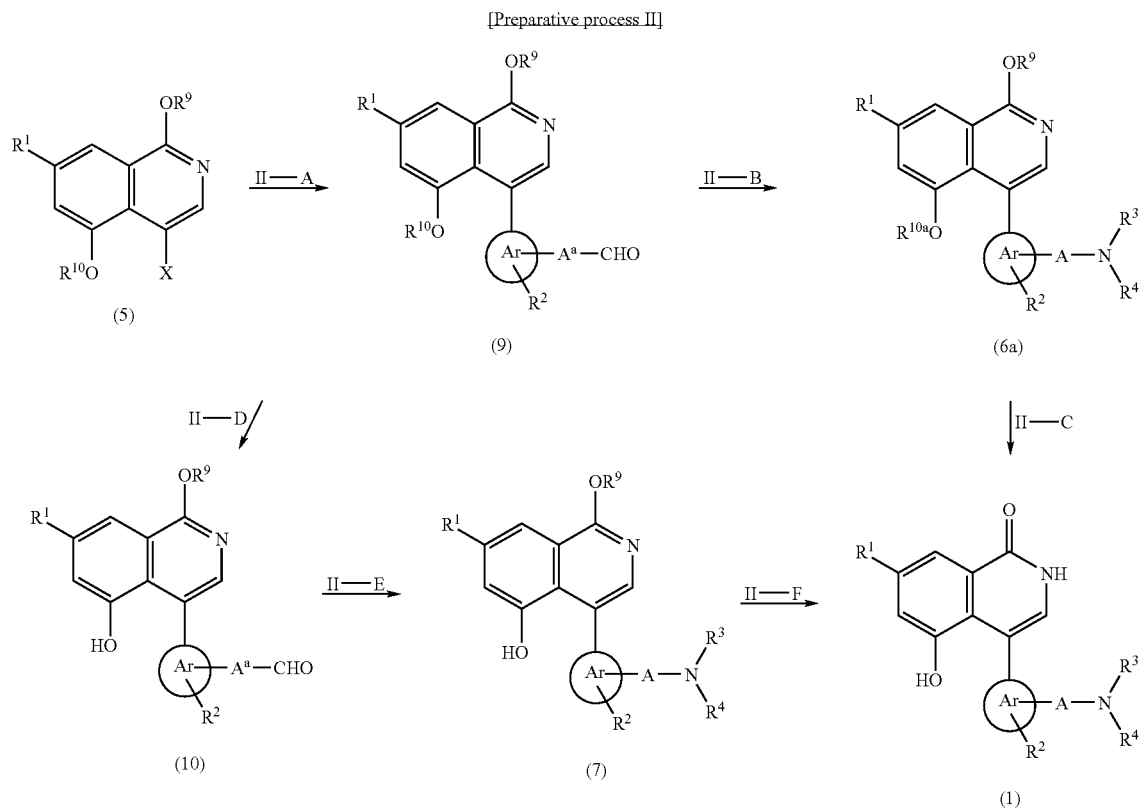

In said formulae, ring Ar, A, $R^1$, $R^2$, $R^3$, $R^4$, $R^9$, $R^{10}$ and X denote the same meanings as described above, $A^a$ denotes a single bond, $C_1$~$C_3$ alkylene or $C_2$~$C_3$ alkenylene, and $R^{10a}$ denotes a lower alkyl group which may be substituted with halogen atom or aralkyl group which may have substituents. The conversion from compounds represented by the general formula (5) to compounds represented by the general formula (9) (process II-A) can be performed through the process similar to process I-A, using compounds represented by a general formula (11)

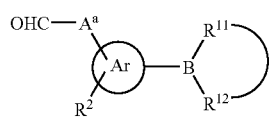

(wherein ring Ar, $A^a$, $R^2$, $R^{11}$ and $R^{12}$ denote the same meanings as described above).

Compounds, $R^{10}$ being lower alkyl group which may be substituted with halogen atom or aralkyl group which may have substituents, among compounds represented by the general formula (9) can be converted to compounds represented by the general formula (6a) (process II-B). Namely, the conversion can be performed by using compounds represented by a general formula (12)

(wherein $R^3$ and $R^4$ denote the same meanings as described above), and by reacting for 1 to 24 hours at 0 to 60° C. in a suitable solvent, for example, methanol, ethanol, dichloromethane, chloroform, mixed solvent thereof or the like, and, if need be, in the presence of a suitable acid, for example, hydrochloric acid, hydrobromic acid, acetic acid or the like, or a suitable Lewis acid, for example, aluminum chloride, zinc chloride or the like, after adding a suitable reducing agent, for example, lithium borohydride, sodium borohydride, sodium cyanoborohydride or the like.

The conversion from compounds represented by the general formula (6a) to compounds represented by the general formula (1) (process II-C) can be performed through the process similar to process I-D.

Moreover, compounds, $R^{10}$ being acyl group, among compounds represented by the general formula (9) can be converted to compounds represented by the general formula (10) (process II-D) through the process similar to process I-B.

The conversion from compounds represented by the general formula (10) to compounds represented by the general formula (7) (process II-E) can be performed through the process similar to process II-B, using compounds represented by the general formula (12)

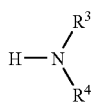

(12)

(wherein $R^3$ and $R^4$ denote the same meanings as described above).

The conversion from compounds represented by the general formula (7) to compounds represented by the general formula (1) (process II-F) can be performed through the process similar to process I-C.

In said formulae, ring Ar, A, $A^a$, $R^1$, $R^2$, $R^3$, $R^4$, $R^9$, $R^{10}$ and X denote the same meanings as described above.

The conversion from compounds represented by the general formula (5) to compounds represented by the general formula (13) (process III-A) can be performed through the process similar to process I-A, using compounds represented by a general formula (15)

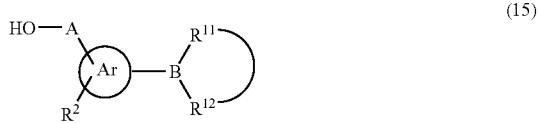

(15)

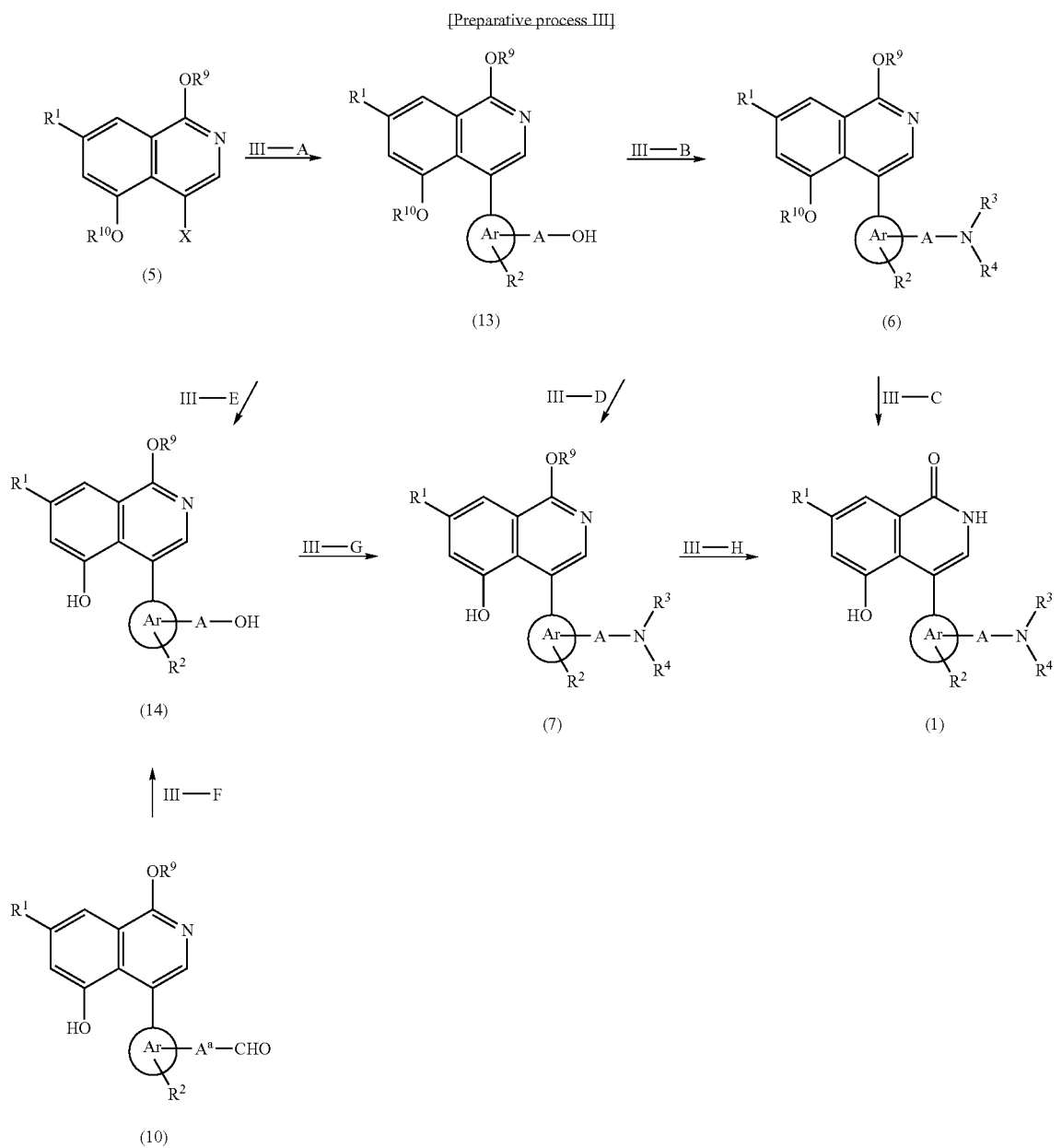

(wherein ring Ar, A, $R^2$, $R^{11}$ and $R^{12}$ denote the same meanings as described above).

The conversion from compounds represented by the general formula (13) to compounds represented by the general formula (6) (process III-B) can be performed by using a suitable halogenating agent, for example, thionyl chloride, phosphorus oxychloride, thionyl bromide or the like, and by reacting for 0.5 to 6 hours at −20 to 80° C. without solvent or in a suitable solvent, for example, dichloromethane, chloroform, tetrahydrofuran, mixed solvent thereof or the like, or by using a suitable sulfonylating agent, for example, methanesulfonyl chloride, trifluoromethanesulfonic anhydride or the like, and by reacting for 0.5 to 3 hours at −20 to 60° C. in a suitable solvent, for example, dichloromethane, tetrahydrofuran, N,N-dimethylformamide, mixed solvent thereof or the like, and then by using compounds represented by the general formula (12)

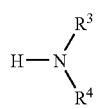

(12)

(wherein $R^3$ and $R^4$ denote the same meanings as described above), and by reacting for 1 to 12 hours at 0 to 120° C. in a suitable solvent, for example, methanol, dichloromethane, tetrahydrofuran, N,N-dimethylformamide, mixed solvent thereof or the like, and, if need be, in the presence of a suitable iodide, for example, sodium iodide, potassium iodide, tetrabutylammonium iodide or the like, or a suitable base, for example, triethylamine, pyridine, N,N-diisopropylethylamine or the like.

Compounds, $R^{10}$ being lower alkyl group which may be substituted with halogen atom or aralkyl group which may have substituents, among compounds represented by the general formula (6) can be converted to compounds represented by the general formula (1) (process III-C) through the process similar to process I-D.

Moreover, compounds, $R^{10}$ being acyl group, among compounds represented by the general formula (6) can be converted to compounds represented by the general formula (7) (process III-D) through the process similar to process I-B.

Compounds, $R^{10}$ being acyl group, among compounds represented by the general formula (13) can be converted to compounds represented by the general formula (14) (process III-E) through the process similar to process I-B.

Moreover, compounds represented by the general formula (14) can also be converted from compounds represented by the general formula (10) (process III-F). Namely, the conversion can be performed by using a suitable reducing agent, for example, lithium borohydride, sodium borohydride, sodium cyanoborohydride or the like, and by reacting for 0.5 to 12 hours at 0 to 80° C. in a suitable solvent, for example, methanol, ethanol, isopropanol, tetrahydrofuran, mixed solvent thereof or the like.

The conversion from compounds represented by the general formula (14) to compounds represented by the general formula (7) (process III-G) can be performed by using a suitable halogenating agent, for example, thionyl chloride, phosphorus oxychloride, thionyl bromide or the like, and by reacting for 0.5 to 6 hours at −20 to 80° C. without solvent or in a suitable solvent, for example, dichloromethane, chloroform, tetrahydrofuran, mixed solvent thereof or the like, and then by using compounds represented by the general formula (12)

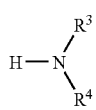

(12)

(wherein $R^3$ and $R^4$ denote the same meanings as described above), and by reacting for 1 to 12 hours at 0 to 120° C. in a suitable solvent, for example, methanol, dichloromethane, tetrahydrofuran, N,N-dimethylformamide, mixed solvent thereof or the like, and, if need be, in the presence of a suitable iodide, for example, sodium iodide, potassium iodide, tetrabutylammonium iodide or the like.

The conversion from compounds represented by the general formula (7) to compounds represented by the general formula (1) (process III-H) can be performed through the process similar to process I-C.

In the Preparative process III aforementioned, compounds represented by the general formula (13a), $R^{10}$ being lower alkyl group which may be substituted with halogen atom or aralkyl group which may have substituents, among compounds represented by the general formula (13) and compounds represented by the general formula (14) can also be synthesized by a separate synthetic process (Preparative process IV) shown below.

[Preparative process IV]

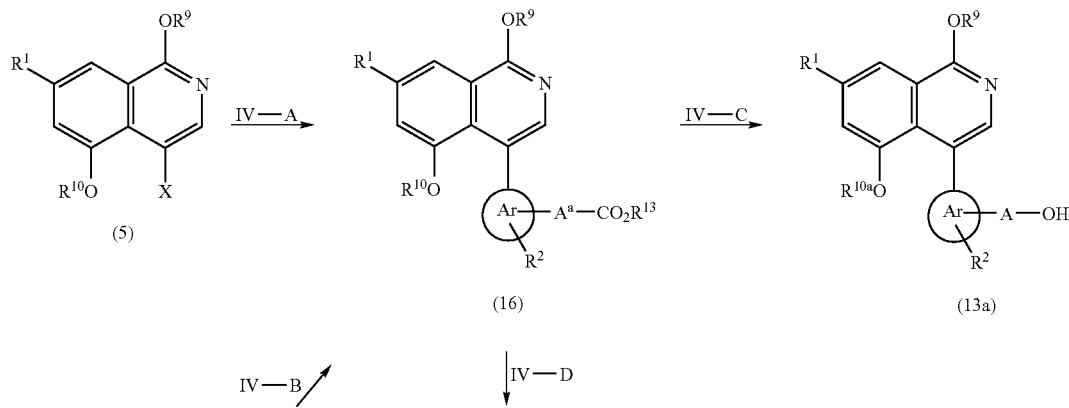

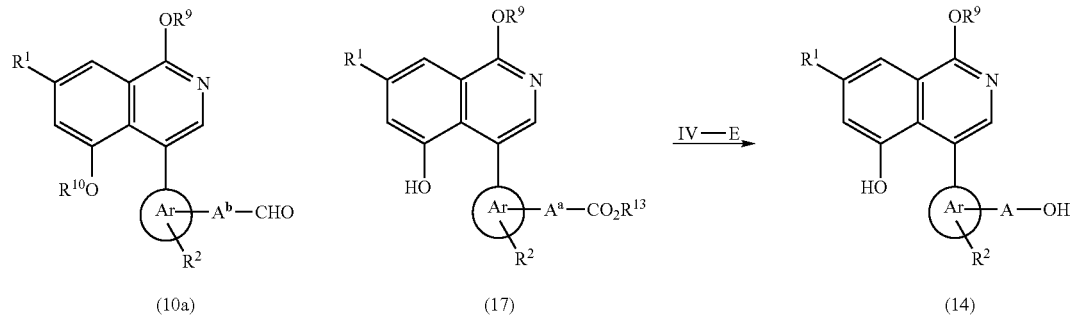

In said formulae, ring Ar, A, $A^a$, $R^1$, $R^2$, $R^9$, $R^{10}$, $R^{10a}$ and X denote the same meanings as described above, $A^b$ denotes a single bond or methylene group, and $R^{13}$ denotes a lower alkyl group which may be substituted with halogen atom or aralkyl group which may have substituents.

The conversion from compounds represented by the general formula (5) to compounds represented by the general formula (16) (process IV-A) can be performed through the process similar to process I-A, using compounds represented by a general formula (18)

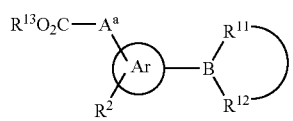

(18)

(wherein ring Ar, $A^a$, $R^2$, $R^{11}$, $R^{12}$ and $R^{13}$ denote the same meanings as described above).

Moreover, compounds, $A^a$ being $C_2$~$C_3$ alkenylene, among compounds represented by the general formula (16) can also be converted from compounds represented by the general formula (10a) (process IV-B). Namely, the conversion can be performed by using compounds represented by a general formula (19)

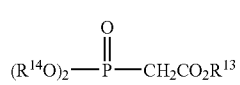

(19)

(wherein $R^{13}$ denotes the same meaning as described above, and $R^{14}$ denotes a lower alkyl group), and by reacting for 1 to 6 hours at −78 to 80° C. in a suitable solvent, for example, methanol, benzene, tetrahydrofuran, N,N-dimethylformamide, mixed solvent thereof or the like, in the presence of a suitable base, for example, sodium hydride, potassium carbonate, triethylamine, pyridine or the like.

Compounds, $A^{10}$ being lower alkyl group which may be substituted with halogen atom or aralkyl group which may have substituents, among compounds represented by the general formula (16) can be converted to compounds represented by the general formula (13a) through the process IV-C. Namely, the conversion can be performed by using a suitable reducing agent, for example, lithium borohydride, lithium aluminum hydride or the like, and by reacting for 0.5 to 6 hours at −20 to 60° C. in a suitable solvent, for example, diethyl ether, tetrahydrofuran or the like.

Moreover, compounds, $R^{10}$ being acyl group, among compounds represented by the general formula (16) can be converted to compounds represented by the general formula (17) through the process IV-D. Namely, the conversion can be performed by using a suitable sodium lower alkoxide, for example, sodium methoxide, sodium ethoxide or the like, and by reacting for 0.5 to 5 hours at −20 to 20° C. in a suitable solvent, for example, methanol, ethanol or the like.

The conversion from compounds represented by the general formula (17) to compounds represented by the general formula (14) (process IV-E) can be performed through the process similar to process IV-C.

Moreover, compounds represented by a general formula (1h) and general formula (1i), A being ethylene or ethenylene and $R^2$ being nitro group which is substituted at ortho position of group $-A-NR^3R^4$, among compounds represented by the general formula (1) can also be synthesized, using processes shown below (Preparative process V).

[Preparation process V]

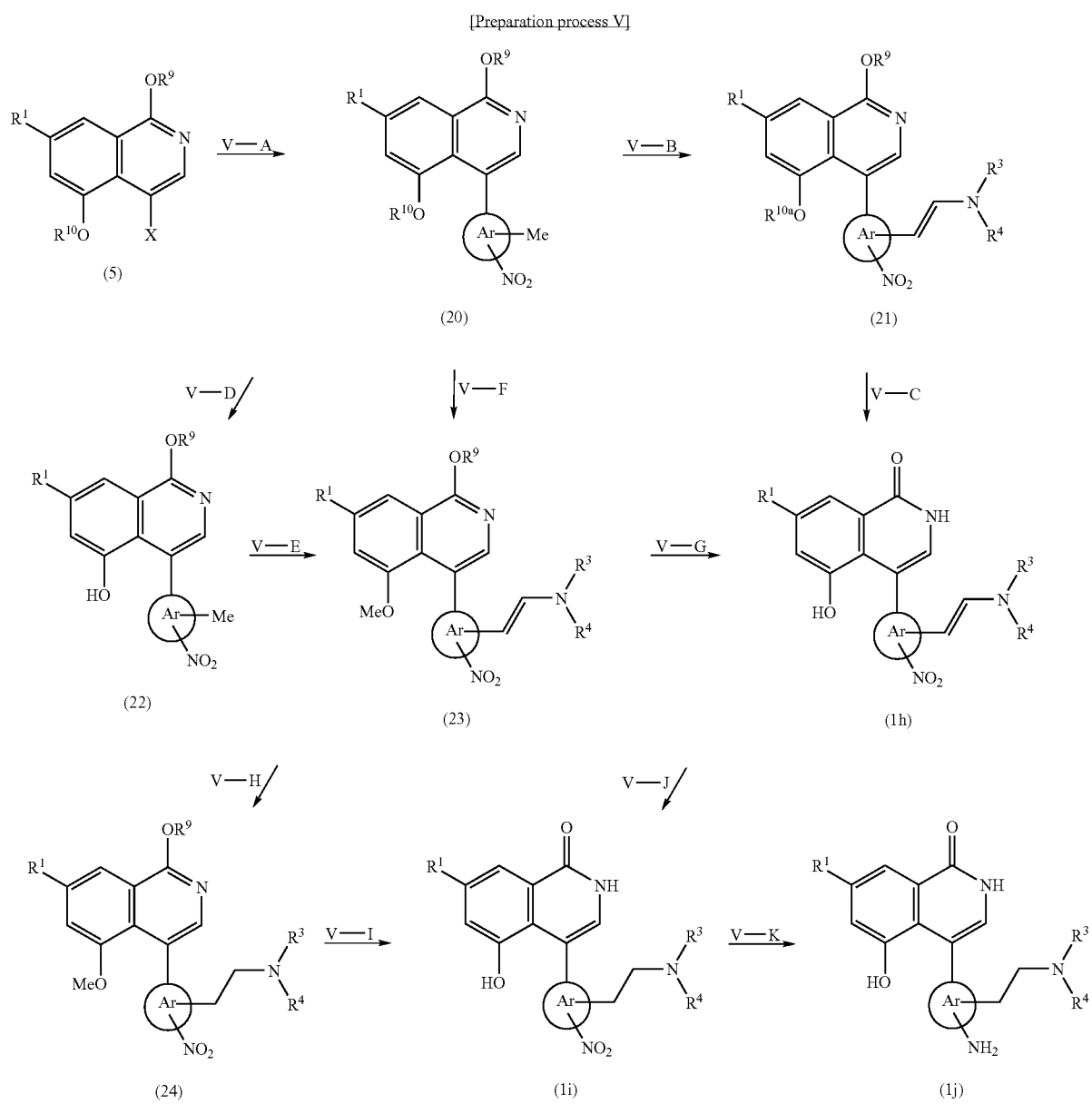

In said formulae, ring Ar, $R^1$, $R^2$, $R^3$, $R^4$, $R^9$, $R^{10}$, $R^{10a}$ and X denote the same meanings as described above.

The conversion from compounds represented by the general formula (5) to compounds represented by the general formula (20) (process V-A) can be performed through the process similar to process I-A, using compounds represented by a general formula (25)

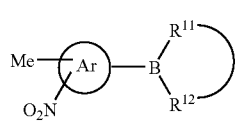

(wherein ring Ar, $R^{11}$ and $R^{12}$ denote the same meanings as described above, and nitro group is substituted at ortho position of methyl group).

Compounds, $R^{10}$ being lower alkyl group which may be substituted with halogen atom or aralkyl group which may have substituents, among compounds represented by the general formula (20) can be converted to compounds represented by the general formula (21) through process V-B. Namely, the conversion can be performed by using compounds represented by a general formula (26)

(wherein $R^{15}$ denotes a lower alkyl group), and by reacting for 1 to 24 hours at 100 to 180° C. in a suitable solvent, for example, N,N-dimethylformamide, N,N-dimethylacetamide, N-methyl-2-pyrrolidinone or the like, after adding compounds represented by the general formula (12)

(12)

(wherein $R^3$ and $R^4$ denote the same meanings as described above), if need be.

The conversion from compounds represented by the general formula (21) to compounds represented by the general formula (1h) (process V-C) can be performed through the process similar to process I-D.

Compounds, $R^{10}$ being acyl group, among compounds represented by the general formula (20) can be converted to compounds represented by the general formula (22) through the process similar to process I-B.

The conversion from compounds represented by the general formula (22) to compounds represented by the general formula (23) (process V-E) can be performed through the process similar to process V-B, using N,N-dimethylformamide as a solvent.

Moreover, compounds represented by the general formula (23) can also be converted directly from compounds, $R^{10}$ being acyl group, among compounds represented by the general formula (20), (process V-F) through the process similar to process V-E.

The conversion from compounds represented by the general formula (23) to compounds represented by the general formula (1h) (process V-G) can be performed through the process similar to process I-D.

Moreover, compounds represented by the general formula (23) can be converted to compounds represented by the general formula (24) through process V-H. Namely, the conversion can be performed by using a suitable reducing agent, for example, sodium borohydride, lithium borohydride or the like, and by reacting for 0.5 to 6 hours at 20 to 80° C. in a suitable solvent, for example, methanol, ethanol, tetrahydrofuran, mixed solvent thereof or the like.

The conversion from compounds represented by the general formula (24) to compounds represented by the general formula (1i) (process V-I) can be performed through the process similar to process I-D.

Moreover, compounds represented by the general formula (1i) can be converted from compounds represented by the general formula (1h) (process V-J) through the process similar to process V-H.

Furthermore, compounds represented by the general formula (1i) can also be converted to compounds, A being ethylene and $R^2$ being amino group which is substituted at ortho position of group -A-$NR^3R^4$, among compounds represented by the general formula (1) (process V-K). Namely, the conversion can be performed by using a suitable catalyst, for example, palladium on carbon, platinum on carbon or the like, and by submitting to the hydrogenating reaction for 1 to 12 hours at 20 to 80° C. under ambient pressure or, if need be, under pressure in a suitable solvent, for example, methanol, tetrahydrofuran, N,N-dimethylformamide, mixed solvent thereof or the like.

In the Preparative processes I through V, compounds represented by the general formula (5), being starting compounds, can be synthesized through processes shown below (Preparative process VI).

[Preparative process VI]

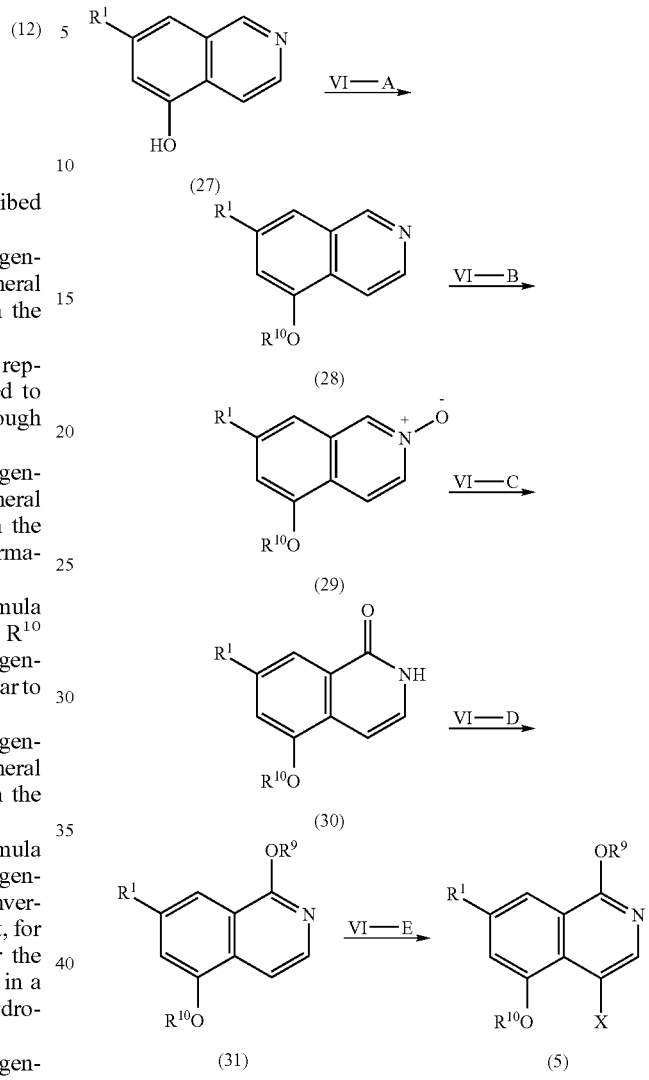

In said formulae, $R^1$, $R^9$, $R^{10}$ and X denote the same meanings as described above.

The conversion from compounds represented by the general formula (27) to compounds represented by the general formula (28) (process VI-A) can be performed, using compounds represented by a general formula (32)

$$R^{10}-X^1 \quad (32)$$

(wherein $R^{10}$ denotes the same meaning as described above, and $X^1$ denotes a halogen atom), and by reacting for 2 to 48 hours at 0 to 140° C. in a suitable solvent, for example, toluene, ethyl acetate, tetrahydrofuran, N,N-dimethylformamide, mixed solvent thereof or the like in the presence of a suitable base, for example, sodium hydride, potassium carbonate, triethylamine or the like.

The conversion from compounds represented by the general formula (28) to compounds represented by the general formula (29) (process VI-B) can be performed by using a suitable peroxide, for example, 3-chloroperbenzoic acid, magnesium monoperoxyphthalate or the like, and by reacting for 4 to 72 hours at 0 to 80° C. in a suitable solvent, for example, benzene, dichloromethane, ethyl acetate, methanol or the like.

The conversion from compounds represented by the general formula (29) to compounds represented by the general formula (30) (process VI-C) can be performed by using a suitable acid anhydride, for example, acetic anhydride, trifluoroacetic anhydride or the like, and by reacting for 1 to 24 hours at 40 to 120° C. without solvent or in a suitable solvent, for example, acetic acid, toluene, 1,4-dioxane, mixed solvent thereof or the like, followed by using water and by reacting for 2 to 48 hours at 60 to 120° C. without solvent or in a suitable solvent, for example, acetic acid, methanol, ethanol, acetonitrile, mixed solvent thereof or the like.

The conversion from compounds represented by the general formula (30) to compounds represented by the general formula (31) (process VI-D) can be performed by using compounds represented by a general formula (33)

(wherein $R^9$ denotes the same meaning as described above, and $X^2$ denotes a halogen atom), and by reacting for 1 to 24 hours at 60 to 110° C. in a suitable solvent, for example, benzene, toluene, ethyl acetate, mixed solvent thereof or the like in the presence of a suitable silver salt, for example, silver oxide, silver trifluoroacetate or the like, or by using a suitable halogenating agent, for example, thionyl chloride, thionyl bromide, phosphorus oxychloride or the like, and by reacting for 0.5 to 12 hours at 0 to 100° C. without solvent or in a suitable solvent, for example, dichloromethane, chloroform, tetrahydrofuran or the like, and then by using compounds represented by a general formula (34)

(wherein $R^9$ denotes the same meaning as described above, and M denotes sodium or potassium), and by reacting for 0.5 to 12 hours at 0 to 100° C. in a suitable solvent, for example, methanol, ethanol, tetrahydrofuran, N,N-dimethylformamide, mixed solvent thereof or the like.

The conversion from compounds represented by the general formula (31) to compounds represented by the general formula (5) (process VI-E) can be performed by using a suitable halogenating agent, for example, bromine, N-bromosuccinimide, N-chlorosuccinimide or the like, and by reacting for 2 to 72 hours at −20 to 120° C. in a suitable solvent, for example, acetic acid, dichloromethane, N,N-dimethylformamide, N,N-dimethylacetamide, mixed solvent thereof or the like.

Moreover, in the Preparative processes I through V, compounds represented by the general formulae (8), (11), (15), (18) and (25) can be synthesized easily through publicly known processes, for example, through the processes described in Tetrahedron Lett., 38, 3447(1997), J. Org. Chem., 60, 7508 (1995), Chem. Rev., 95, 2457 (1995), etc.

In compounds represented by the general formula (1) or compounds represented by the general formula (6) and general formula (7), being synthetic intermediates in the Preparative processes I through III, the conversion of $R^2$ to other substituent in the case of need can also be performed through publicly known processes. For example, compounds, $R^2$ being lower alkoxy group which may be substituted with halogen atom, among compounds represented by the general formula (1) can be converted to compounds, $R^2$ being hydroxy group, among compounds represented by the general formula (1), by using a suitable acid, for example, hydrochloric acid, hydrobromic acid or the like, and by reacting for 1 to 24 hours at 60 to 110° C. without solvent or in a suitable solvent, for example, water, acetic acid, mixed solvent thereof or the like.

Moreover, compounds, $R^2$ being nitro group, among compounds represented by the general formula (1) can be converted to compounds, $R^2$ being amino group, among compounds represented by the general formula (1), by using a suitable catalyst, for example, palladium on carbon, platinum on carbon or the like, and by submitting to the hydrogenating reaction for 1 to 72 hours at 20 to 80° C. under ambient pressure or, if need be, under pressure in a suitable solvent, for example, methanol, ethanol, tetrahydrofuran, N,N-dimethylformamide, mixed solvent thereof or the like, and further they can be converted to compounds, $R^2$ being amino group which may have substituents, among compounds represented by the general formula (1), by using a suitable acylating agent, for example, acetic anhydride, acetyl chloride or the like, or a suitable sulfonylating agent, for example, methanesulfonyl chloride, 4-toluenesulfonyl chloride or the like, and by reacting for 1 to 24 hours at 0 to 80° C. in a suitable solvent, for example, chloroform, tetrahydrofuran, N,N-dimethylformamide, mixed solvent thereof or the like without base or in the presence of a suitable base, for example, triethylamine, pyridine or the like.

Similarly, in the case of compounds, $R^4$ being general formula (3) and $R^6$ being phenyl group which may have substituents, naphthyl group which may have substituents or 5- or 6-membered heterocycle which may have substituents and its condensed ring, wherein the substituent is lower alkoxy group which may be substituted with halogen atom or nitro group, among compounds represented by the general formula (1) or compounds represented by the general formula (6) and general formula (7), being synthetic intermediates in the Preparative processes I through III, it is also possible to convert to hydroxy group, amino group and amino group which may have substituents.

Processes for converting $R^2$ in compounds represented by the general formula (1) or compounds represented by the general formula (6) and general formula (7), being synthetic intermediates in the Preparative processes I through III, and the substituent in compounds, $R^4$ being general formula (3) and $R^6$ being phenyl group which may have substituents, naphthyl group which may have substituents or 5- or 6-membered heterocycle which may have substituents and its condensed ring, among compounds represented by the general formula (1) or compounds represented by the general formula (6) and general formula (7), being synthetic intermediates in the Preparative processes I through III, to other substituents, if need be, are not confined to these.

The 4-substituted aryl-5-hydroxyisoquinolinone derivatives represented by the general formula (1) and their addition salts of the invention exhibit excellent PARP inhibitory activity. When using the inventive compounds for therapeutic or preventive agents, they can be used solely or by mixing opportunely with pharmacologically acceptable excipient, diluent or the like, and administered orally in a form of tablet, capsule, granule, powder, syrup or the like, or parenterally in a form of injection, percutaneous absorption, suppository or the like.

Moreover, the inventive compounds can be used in combination with other drugs. In this case, they may be used for combination administrations or formulating agents. As the drugs to be used for combination, fibrinolytic agent, antiplatelet, protector of brain, antiedemic agent, anticoagulant, antipyretic, improver of cerebral circulatory metabolism, antiepileptic, antidepressant, anti-inflammatory drug, ACE inhibitor, antiphlogistic analgesic, blood glucose regulator, etc. are mentioned.

Moreover, the inventive compounds can be used in combination, even in the cases of surgical therapy, hypothermic therapy, hyperbaric oxygen therapy, etc.

BEST MODE FOR CARRYING OUT THE INVENTION

In following, referential examples, examples and test examples will be shown to illustrate the invention in more detail, but the scope of the invention is not confined thereto.

REFERENTIAL EXAMPLE 1

5-Benzoyloxyisoquinoline

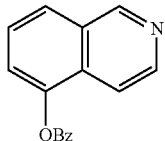

To a solution of 5-hydroxyisoquinoline (15.0 g, 103 mmol) in dichloromethane (300 ml) was added triethylamine (10.9 g, 108 mmol), and the mixture was cooled to 0° C. Under stirring, benzoyl chloride (15.2 g, 108 mmol) was added dropwise and the temperature was raised to room temperature. After stirring for 6 hours at room temperature, dichloromethane was added. The solution was washed with saturated aqueous solution of sodium hydrogencarbonate, then dried over anhydrous magnesium sulfate and solvent was distilled off, thereby affording 26.6 g of the title compound as a light brown liquid. Yield quantitative. $^1$H-NMR (DMSO-$d_6$, δ): 7.68(2H, t, J=7.3 Hz), 7.75(1H, d, J=5.9 Hz), 7.79-7.85 (3H, m), 8.12-8.16(1H, m), 8.28(2H, d, J=7.3 Hz), 8.55 (1H, d, J=5.9 Hz), 9.45(1H, s).

REFERENTIAL EXAMPLE 2

5-Benzoyloxyisoquinoline N-oxide

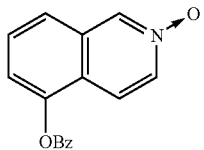

To a solution of the compound of Referential example 1 (1.92 g, 7.70 mmol) in dichloromethane (100 ml) was added 3-chloroperbenzoic acid (2.45 g, 9.24 mmol), and the mixture was stirred for 6 hours at room temperature. Saturated aqueous solution of sodium hydrogencarbonate was added and the solution was extracted with dichloromethane. The extract was dried over anhydrous magnesium sulfate and solvent was distilled off, thereby affording 2.35 g of the title compound as light brown powder. Yield quantitative. $^1$H-NMR (DMSO-$d_6$, δ): 7.61(1H, d, J=7.8 Hz), 7.67(2H, t, J=8.3 Hz),7.75 (1H, t, J=7.8 Hz), 7.82(1H, t, J=8.3 Hz), 7.86-7.88(2H, m),8.14(1H, d, J=7.3 Hz), 8.26(2H, d, J=8.3 Hz), 9.07(1H, s).

REFERENTIAL EXAMPLE 3

5-Benzoyloxy-1,2-dihydro-1-oxoisoquinoline

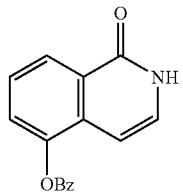

To the compound of Referential example 2 (29.9 g, 123 mmol) was added acetic anhydride (100 mL), and the mixture was refluxed for 4 hours. After the reaction mixture was concentrated under reduced pressure, ethanol (100 ml) and water (50 ml) were added and the mixture was refluxed for 30 minutes. Ethanol was added to the residue obtained by distilling off solvent. The precipitated crystals were collected by filtration, washed with ethanol, and then air-dried, thereby affording 19.0 g of the title compound as brown powder. Yield 64%. $^1$H-NMR(DMSO-$d_6$, δ): 6.40(1H, d, J=7.3 Hz), 7.21 (1H, t, J=6.3 Hz), 7.57 (1H, t, J=7.8 Hz), 7.64-7.72(3H, m), 7.81(1H, t, J=7.3 Hz), 8.16(1H, d, J=7.3 Hz), 8.23(2H, d, J=7.8 Hz), 11.45(1H, brs).

REFERENTIAL EXAMPLE 4

5-Benzoyloxy-1-methoxyisoquinoline

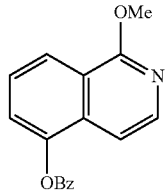

To a solution of the compound of Referential example 3 (22.1 g, 83.3 mmol) in toluene (300 mL) was added silver oxide (I) (57.9 g, 250 mmol) and methyl iodide (30 mL), and the mixture was refluxed for 8 hours. The reaction mixture was filtered using celite and the residue obtained by distilling off solvent was purified by silica gel column chromatography [hexane:ethyl acetate (20:1→10:1)], thereby affording 9.83 g of the title compound as colorless powder. Yield 42%. $^1$H-NMR(DMSO-$d_6$, δ): 4.10(3H, s), 7.29(1H, d, J=5.8 Hz), 7.66-7.73 (3H, m), 7.77(1H, dd, J=7.8, 1.0 Hz), 7.82(1H, t, J=7.3 Hz),8.05(1H, d, J=5.8 Hz), 8.16(1H, d, J=7.8 Hz), 8.26(2H, d, J=7.3 Hz).

REFERENTIAL EXAMPLE 5

5-Benzoyloxy-4-bromo-1-methoxyisoquinoline

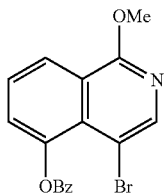

A solution of the compound of Referential example 4 (9.83 g, 35.2 mmol) in N,N-dimethylformamide (200 mL) was cooled to 0° C. and, under stirring, N-bromosuccinimide (6.39 g, 35.9 mmol) was added little by little. After stirring for 30 minutes at 0° C., the temperature was raised to room temperature and the mixture was stirred for 16 hours. The residue obtained by concentrating the reaction mixture was purified by silica gel column chromatography [hexane:ethyl acetate (20:1→10:1)], thereby affording 11.6 g of the title compound as colorless powder. Yield 92%. $^1$H-NMR (DMSO-$d_6$, δ): 4.10(3H, s), 7.66(2H, t, J=8.3 Hz), 7.77-7.82 (3H, m), 8.22(2H, d, J=8.3 Hz), 8.26(1H, s), 8.28-8.32(1H, m).

REFERENTIAL EXAMPLE 6

5-Benzoyloxy-4-(4-formylphenyl)-1-methoxyisoquinoline

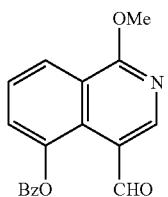

To a suspension of the compound of Referential example 5 (20.0 g, 55.8 mmol) and 4-formylphenylboric acid (12.6 g, 83.8 mmol) in toluene (50 mL) were added [1,1'-bis(diphenylphosphino)ferrocene]dichloropalladium(II)-dichloromethane(1:1) complex (1.22 g, 1.67 mmol) and 2 mol/L aqueous solution of sodium carbonate, and the mixture was refluxed for 5 hours. After cooling, the organic layer was separated, dried over anhydrous sodium sulfate, and then solvent was distilled off. A small quantity of ethyl acetate was added to the residue obtained. The crystals were collected by filtration, washed with ethyl acetate, and then air-dried, thereby affording 16.08 g of the title compound as yellow powder. Yield 78%. $^1$H-NMR (DMSO-$d_6$, δ): 4.15(3H, s), 7.30(2H, t, J=7.8 Hz), 7.42(2H, d, J=7.8 Hz), 7.51-7.55(5H, m), 7.68(1H, d, J=7.3 Hz), 7.78(1H, d, J=7.8 Hz), 7.81(1H, s), 8.32(1H, d, J=8.3 Hz), 9.59(1H, s).

REFERENTIAL EXAMPLE 7

5-Benzoyloxy-4-(3-formylphenyl)-1-methoxyisoquinoline

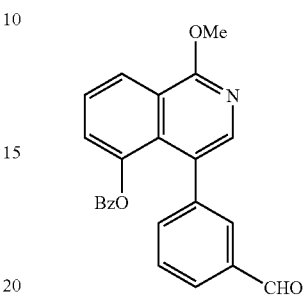

Using the compound of Referential example 5 (3.58 g, 10.0 mmol) and 3-formylphenylboric acid (2.55 g, 15.0 mmol), through the process similar to Referential example 6, 2.91 g of the title compound were afforded as colorless powder. Yield 76%. $^1$H-NMR (DMSO-$d_6$, δ): 4.14(3H, s), 7.23-7.33 (4H, m), 7.46-7.49(2H, m), 7.53-7.60(2H, m), 7.67(1H, dd, J=7.8, 1.5 Hz), 7.73-7.80(3H, m), 8.32 (1H, dd, J=8.3, 1.5 Hz), 9.77(1H, s).

REFERENTIAL EXAMPLE 8

4-(4-Formylphenyl)-5-hydroxy-1-methoxyisoquinoline

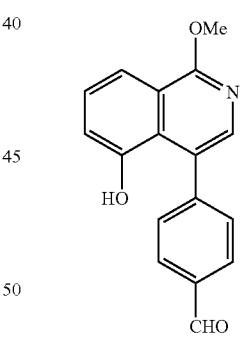

To a suspension of the compound of Referential example 6 (6.65 g, 17.3 mmol) in ethanol-water (2:1, 150 mL) was added 1 mol/L aqueous solution of sodium hydroxide (17.3 mL, 17.3 mmol), and the mixture was refluxed for 1 hour. After cooling, water was added to the reaction mixture, which was extracted with ethyl acetate. The extract was dried over anhydrous sodium sulfate, and then solvent was distilled off. The residue obtained was purified by silica gel column chromatography [hexane: ethyl acetate=4:1], thereby affording 2.08 g of the title compound as pale yellow powder. Yield 43%. $^1$H-NMR (DMSO-$d_6$, δ): 4.08(3H, s), 7.05(1H, dd, J=7.8, 1.0 Hz), 7.48 (1H, t, J=7.8 Hz), 7.55(2H, d, J=8.3 Hz), 7.70(1H, s), 7.74(1H, dd, J=8.3, 1.0 Hz), 7.89(2H, d, J=8.3 Hz), 10.04(1H, s), 10.06(1H, s).

REFERENTIAL EXAMPLE 9

4-(3-Formylphenyl)-5-hydroxy-1-methoxyisoquinoline

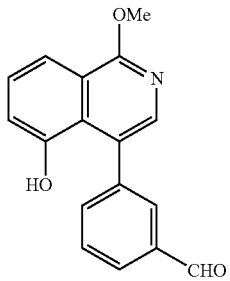

Using the compound of Referential example 7 (4.46 g, 11.6 mmol), through the process similar to Referential example 8, 2.43 g of the title compound were afforded as a pale yellow amorphous material.

Yield 75%. $^1$H-NMR (DMSO-$d_6$, δ): 4.07(3H, s), 7.04(1H, dd, J=7.8, 1.0 Hz), 7.47 (1H, t, J=7.8 Hz), 7.58(1H, t, J=7.8 Hz), 7.66-7.70(2H, m), 7.74(1H, dd, J=8.3, 1.0 Hz), 7.85-7.87(2H, m), 10.06(1H, s), 9.80-10.20(1H, br).

REFERENTIAL EXAMPLE 10

5-Benzoyloxy-4-(3-formyl-4-methoxyphenyl)-1-methoxyisoquinoline

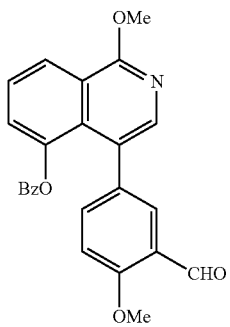

Using the compound of Referential example 5 (1.79 g, 5.00 mmol) and 3-formyl-4-methoxyphenylboric acid (1.35 g, 7.50 mmol), through the process similar to Referential example 6, 317 mg of the title compound were afforded as light brown powder. Yield 15%. $^1$H-NMR (DMSO-$d_6$, δ): 3.55(3H, s), 4.18(3H, s), 6.54(1H, d, J=8.8 Hz), 7.29(2H, t, J=7.8 Hz), 7.35-7.40(2H, m), 7.53(1H, t, J=7.8 Hz), 7.60-7.67(3H, m), 7.74-7.76(2H, m), 8.34(1H, dd, J=8.3, 1.0 Hz), 10.20 (1H, s).

REFERENTIAL EXAMPLE 11

4-(3-Formyl-4-methoxyphenyl)-5-hydroxy-1-methoxyisoquinoline

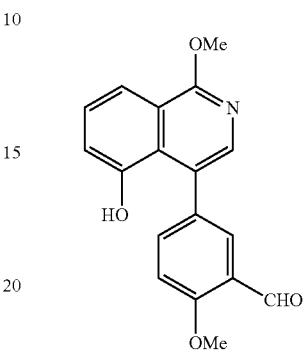

Using the compound of Referential example 10 (315 mg, 762 μmol), through the process similar to Referential example 8, 192 mg of the title compound were afforded as pale yellow powder. Yield 81%. $^1$H-NMR (DMSO-$d_6$, δ): 3.97(3H, s), 4.06(3H, s), 7.03(1H, d, J=7.8 Hz), 7.22(1H, d, J=8.3 Hz), 7.45(1H, t, J=7.8 Hz), 7.60-7.65(3H, m), 7.72 (1H, d, J=8.3 Hz), 10.42(1H, s).

REFERENTIAL EXAMPLE 12

5-Benzoyloxy-1-methoxy-4-(4-methyl-3-nitrophenyl)isoquinoline

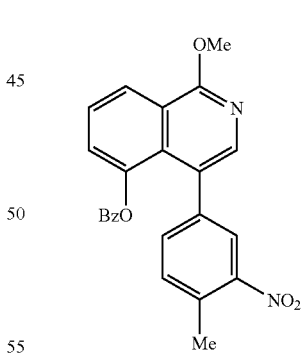

Using the compound of Referential example 5 (2.51 g, 7.00 mmol) and 4-methyl-3-nitrophenylboric acid (1.90 g, 10.5 mmol), through the process similar to Referential example 6, 2.51 g of the title compound were afforded as colorless powder. Yield 87%. $^1$H-NMR (DMSO-$d_6$, δ): 2.04(3H, s), 4.14 (3H, s), 7.14(1H, d, J=7.8 Hz), 7.38(2H, t, J=7.3 Hz), 7.46 (1H, dd, J=7.8, 2.0 Hz), 7.57(2H, dd, J=8.3, 1.0 Hz), 7.62-7.69(2H, m), 7.77-7.81(3H, m), 8.32(1H, dd, J=8.3, 1.0 Hz).

REFERENTIAL EXAMPLE 13

1,5-Dimethoxy-4-[4-(2-dimethylamino)ethyl-3-nitrophenyl]isoquinoline

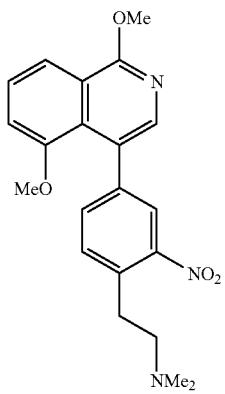

To a solution of the compound of Referential example 12 (2.07 g, 5.00 mmol) in N,N-dimethylformamide (50 mL) was added N,N-dimethylformamidodimethylacetal (3.32 mL, 25.0 mmol), and the mixture was refluxed for 6 hours. After cooling, ethanol (50 mL) and successively sodium borohydride (567 mg, 15.0 mmol) were added to the residue obtained by concentrating the reaction mixture under reduced pressure and the mixture was refluxed for 5 hours. After cooling, water was added to the reaction mixture, which was extracted with ethyl acetate, dried over anhydrous sodium sulfate, and then solvent was evaporated. The obtained residue was purified by silica gel column chromatography [hexane-ethyl acetate (1:1) →ethyl acetate-methanol-triethylamine (10:1:0.1)], thereby affording 498 mg of the title compound as a brown viscous liquid. Yield 26%. $^1$H-NMR (DMSO-$d_6$, δ): 2.36(6H, s), 2.68 (2H, t, J=7.8 Hz), 3.14(2H, brs), 3.56(3H, s), 4.16(3H, s), 7.02(1H, d, J=7.3 Hz), 7.36(1H, d, J=7.8 Hz), 7.48-7.53(2H, m), 7.78(1H, s), 7.88(1H, d, J=2.0 Hz), 7.95(1H, dd, J=8.3, 1.0 Hz).

REFERENTIAL EXAMPLE 14

2-[4-(4,4,5,5-Tetramethyl-1,3,2-dioxobororan-2-yl)phenyl]ethanol

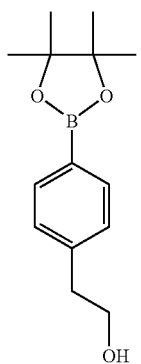

To a solution of 2-(4-bromophenyl)ethanol (500 mg, 2.49 mmol) in dimethylsulfoxide (5 mL) were added bis(pinacolato)diboron (632 mg, 2.49 mmol), potassium acetate (733 mg, 7.47 mmol) and [1,1'-bis (diphenylphosphino)ferrocene] dichloropalladium(II)-dichloromethane (1:1) complex (102 mg, 124 μmol), and the mixture was stirred for 5 hours at 120° C. Ice water and toluene were added to the reaction mixture and the insolubles were filtered off. The organic layer was separated, washed with water, then dried over anhydrous sodium sulfate, and solvent was distilled off. The residue obtained was purified by silica gel column chromatography [hexane-ethyl acetate=1:1], thereby affording 455 mg of the title compound as a pale yellow oil. Yield 89%. $^1$H-NMR (CDCl$_3$, δ): 1.34(12H, s), 2.89(2H, t, J=6.3 Hz), 3.87(2H, q, J=6.3 Hz), 7.25(2H, d, J=7.8 Hz), 7.77(2H, d, J=8.3 Hz).

REFERENTIAL EXAMPLE 15

2-[3-(4,4,5,5-Tetramethyl-1,3,2-dioxobororane-2-yl)phenyl]ethanol

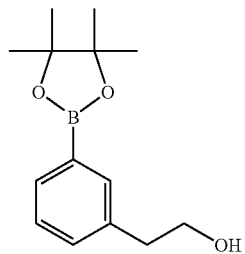

Using 2-(3-bromophenyl)ethanol (4.17 g, 20.7 mmol), through the process similar to Referential example 14, 3.98 g of the title compound were afforded as a yellow oil. Yield 77%. $^1$H-NMR (CDCl$_3$, δ): 1.35(12H, s), 2.88(2H, t, J=6.3 Hz), 3.87(2H, q, J=6.3 Hz), 7.32-7.37(2H, m), 7.67-7.69(2H, m).

REFERENTIAL EXAMPLE 16

3-[4-(4,4,5,5-Tetramethyl-1,3,2-dioxobororane-2-yl)phenyl]propanol

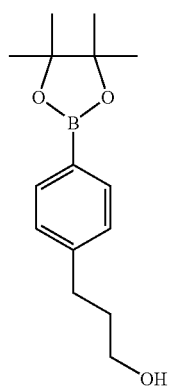

Using 3-(4-bromophenyl)propanol (508 mg, 2.36 mmol), through the process similar to Referential example 14, 229 mg of the title compound were afforded as a yellow oil. Yield 37%. $^1$H-NMR (CDCl$_3$, δ): 1.34(12H, s), 1.86-1.93(2H, m), 2.70-2.75 (2H, m), 3.65-3.69(2H, m), 7.22(2H, d, J=8.3 Hz), 7.74(2H, d, J=7.8 Hz).

REFERENTIAL EXAMPLE 17

5-Benzoyloxy-4-[4-(2-hydroxyethyl)phenyl]-1-methoxyisoquinoline

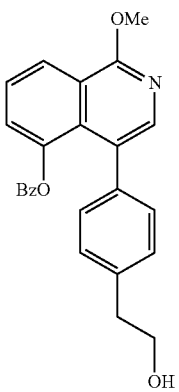

Using the compound of Referential example 5 (634 mg, 1.77 mmol) and the compound of Referential example 14 (440 mg, 1.77 mmol), through the process similar to Referential example 6, 225 mg of the title compound were afforded as pale yellow powder. Yield 32%. $^1$H-NMR (CDCl$_3$, δ): 2.45(2H, t, J=6.3 Hz), 3.53(2H, q, J=6.3 Hz), 4.18 (3H, s), 6.89(2H, d, J=7.8 Hz), 7.21(2H, d, J=7.8 Hz), 7.31(2H, t, J=8.3 Hz), 7.38(1H, dd, J=7.8, 1.0 Hz), 7.51-7.55(1H, m), 7.61(1H, t, J=7.8 Hz), 7.68(2H, dd, J=8.3, 1.5 Hz), 7.77(1H, s), 8.34(1H, dd, J=8.3, 1.0 Hz).

REFERENTIAL EXAMPLE 18

5-Benzoyloxy-4-[3-(2-hydroxyethyl)phenyl]-1-methoxyisoquinoline

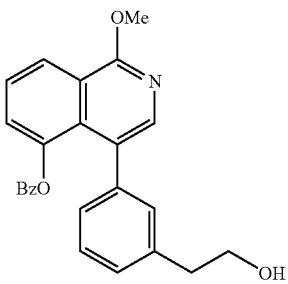

Using the compound of Referential example 5 (5.07 g, 14.2 mmol) and the compound of Referential example 15 (3.52 g, 14.2 mmol), through the process similar to Referential example 6, 4.05 g of the title compound were afforded as a yellow oil. Yield 71%. $^1$H-NMR (CDCl$_3$, δ): 2.54-2.64(2H, m), 3.64(2H, q, J=6.3 Hz), 4.18(3H, s), 6.66(1H, d, J=7.3 Hz), 7.02(1H, t, J=7.8 Hz), 7.08(1H, s), 7.17-7.19 (1H, m), 7.28-7.31(2H, m), 7.39(1H, dd, J=7.3, 1.0 Hz), 7.49-7.54(1H, m), 7.59-7.63(3H, m), 7.77(1H, s), 8.34(1H, dd, J=8.3, 1.5 Hz).

REFERENTIAL EXAMPLE 19

5-Benzoyloxy-4-[4-(3-hydroxypropyl)phenyl]-1-methoxyisoquinoline

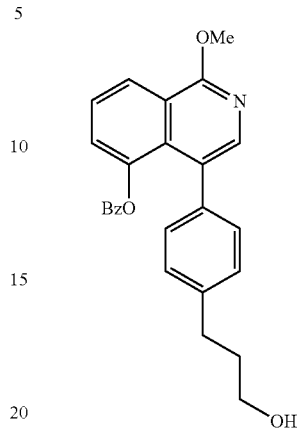

Using the compound of Referential example 5 (5.12 g, 14.3 mmol) and the compound of Referential example 16 (3.75 g, 14.3 mmol), through the process similar to Referential example 6, 3.03 g of the title compound were afforded as pale yellow powder. Yield 51%. $^1$H-NMR (CDCl$_3$, δ): 1.52-1.59 (2H, m), 2.27(2H, t, J=7.3 Hz), 3.53(2H, q, J=6.3 Hz), 4.18 (3H, s), 6.85(2H, d, J=7.8 Hz), 7.18(2H, d, J=7.8 Hz), 7.29 (2H, t, J=7.8 Hz), 7.38(1H, dd, J=7.8, 1.0 Hz), 7.50(1H, t, J=7.3 Hz), 7.60(1H, t, J=8.3 Hz), 7.65(2H, dd, J=8.3, 1.0 Hz), 7.78(1H, s),8.33(1H, dd, J=8.3, 1.0 Hz).

REFERENTIAL EXAMPLE 20

5-Benzoyloxy-4-(5-formyl-2-thienyl-1-methoxyisoquinoline

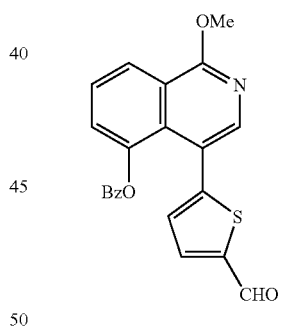

To a solution of the compound of Referential example 5 (1.00 g, 279 mmol) in anhydrous 1,4-dioxane (60 mL) were added 5-formyl-2-thiopheneboric acid (1.31 g, 8.38 mmol), triethylamine (1.17 mL,8.38 mmol) and [1,1'-bis(diphenylphosphino)ferrocene]dichloropalladium(II)-dichloromethane(1:1) complex (228 mg,280 μmol), and the mixture was refluxed for 9 hours. After cooling, the reaction mixture was filtered through celite and the filtrate was concentrated under reduced pressure. The residue obtained was purified by silica gel column chromatography [hexane:ethyl acetate (4:3→1:1)], thereby affording 990 mg of the title compound as pale yellow powder.

Yield 91%. $^1$H-NMR (CDCl$_3$, δ): 4.19(3H, s), 6.92(1H, d, J=3.9 Hz), 7.03(1H, d, J=3.4 Hz), 7.34(2H, t, J=7.8 Hz), 7.47(1H, dd, J=8.3, 1.5 Hz), 7.55(1H, t, J=7.8 Hz), 7.66(1H, t, J=8.3 Hz), 7.82(2H, dd, J=8.3, 1.5 Hz), 7.93(1H, s), 8.35 (1H, dd, J=8.3, 1.5 Hz), 9.38(1H, s).

REFERENTIAL EXAMPLE 21

4-(5-Formyl-2-thienyl)-5-hydroxy-1-methoxyiso-quinoline

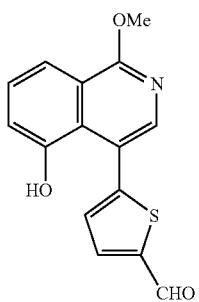

To a solution of the compound of Referential example 20 (49.3 mg, 127 μmol) in ethanol (3 mL) was added sodium hydrogencarbonate (31.9 mg, 380 μmol), and the mixture was refluxed for 8 hours. After cooling, water was added and the solution was brought to pH 1 using 1 mol/L hydrochloric acid. This was extracted with ethyl acetate, washed with brine, then dried over anhydrous sodium sulfate, and solvent was distilled off. The residue obtained was purified by silica gel column chromatography [hexane:ethyl acetate=4:1], thereby affording 30.3 mg of the title compound as pale yellow powder. Yield 84%. $^1$H-NMR (CDCl$_3$, δ): 4.17(3H, s), 7.14(1H, dd, J=7.8, 1.0 Hz), 7.51(1H, t, J=7.8 Hz), 7.81(1H, d, J=3.4 Hz), 7.92(1H, s), 7.97(1H, dd, J=8.3, 1.0 Hz), 9.96 (1H, s).

REFERENTIAL EXAMPLE 22

5-Benzoyloxy-4-(4-formyl-1-naphthyl-1-methoxy-isoquinoline

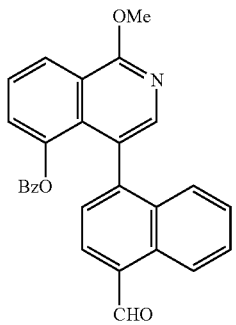

Using the compound of Referential example 5 (1.43 g, 4.00 mmol) and 4-formyl-1-naphthaleneboric acid (1.00 g, 5.00 mmol), through the process similar to Referential example 6, 1.23 g of the title compound were afforded as pale yellow powder. Yield 71%. $^1$H-NMR (DMSO-d$_6$, δ): 4.19(3H, s), 6.82-6.84(2H, m), 7.09(2H, t, J=7.9 Hz), 7.40-7.52(4H, m), 7.58(1H, dd, J=6.7, 1.2 Hz), 7.65-7.69(1H, m), 7.75-7.82(2H, m), 7.88(1H, s), 8.38(1H, dd, J=7.3, 1.2 Hz), 8.96(1H, d, J=8.6 Hz),9.95(1H, s).

REFERENTIAL EXAMPLE 23

4-(4-Formyl-1-naphthyl)-5-hydroxy-1-methoxyiso-quinoline

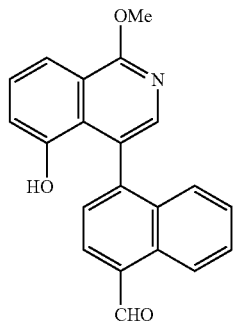

To a solution of the compound of Referential example 22 (610 mg, 1.41 mmol) in ethanol (15 mL) was added potassium hydroxide (92.0 mg, 1.41 mmol), and the mixture was refluxed for 1 hour. After cooling, the residue obtained by concentrating the reaction mixture was purified by silica gel column chromatography [hexane:ethyl acetate=10:1], then diisopropyl ether was added and the precipitated crystals were collected by filtration, thereby affording 328 mg of the title compound as colorless powder. Yield 71%. $^1$H-NMR (DMSO-d$_6$, δ): 4.14(3H, s), 6.90(1H, brd, J=6.7 Hz), 7.41-7.50 (3H, m), 7.64-7.70(2H, m), 7.76-7.80(2H, m), 8.22(1H, d, J=6.7 Hz), 9.25 (1H, d, J=9.2 Hz), 9.74(1H, brs), 10.45(1H, s).

REFERENTIAL EXAMPLE 24

5-Benzoyloxy-4-(4-fluoro-3-formylphenyl)-1-methoxyisoquinoline

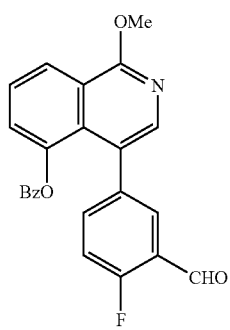

To a solution of the compound of Referential example 5 (1.79 g, 5.00 mmol) in toluene (50 mL) were added 4-fluoro-3-formylphenylboric acid (1.01 g, 6.00 mmol), 2 mol/L aqueous solution of sodium carbonate (5.00 mL, 10.0 mmol) and [1,1'-bis(diphenylphosphino)ferrocene]dichloropalladium (II)-dichloromethane(1:1) complex (204 mg, 250 μmol), and the mixture was refluxed for 5 hours. After cooling, the organic layer was separated, dried over anhydrous sodium sulfate, and then solvent was distilled off. The residue obtained was purified by silica gel column chromatography [hexane:ethyl acetate=4:1], thereby affording 1.58 g of the title compound as colorless powder.

Yield 79%.

¹H-NMR (DMSO-d₆, δ): 4.14(3H, s), 7.07(1H, dd, J=7.9, 10.4 Hz), 7.40 (2H, t, J=7.9 Hz), 7.54-7.69(6H, m), 7.77-7.80 (2H, m), 8.32(1H, d, J=8.6 Hz), 9.92(1H, s).

REFERENTIAL EXAMPLE 25

4-(4-Fluoro-3-formylphenyl)-5-hydroxy-1-methoxyisoquinoline

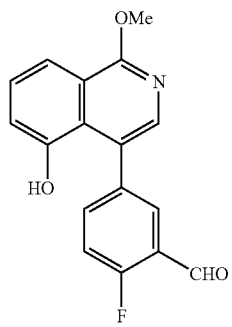

To a solution of the compound of Referential example 24 (1.58 g, 3.93 mmol) in ethanol (80 mL) was added sodium hydrogen carbonate (991 mg, 11.8 mmol), and the mixture was refluxed for 8 hours. After cooling, brine was added and the solution was extracted with ethyl acetate, dried over anhydrous sodium sulfate, and then solvent was distilled off. Dichloromethane was added to the residue obtained, The precipitates were collected by filtration and dried, thereby affording 765 mg of the title compound as pale yellow powder. The filtrate was concentrated and purified by silica gel column chromatography [hexane:ethyl acetate=4:1], thereby affording 155 mg additionally.

Total yield 97%.

¹H-NMR (DMSO-d₆, δ): 4.07(3H, s), 7.04-7.06(1H, m), 7.39(1H, dd, J=10.4, 7.9 Hz), 7.47(1H, t, J=7.9 Hz), 7.68-7.77(4H, m), 10.05(1H, s), 10.28(1H, s).

REFERENTIAL EXAMPLE 26

Ethyl 4-(5-hydroxy-1-methoxyisoquinoline-4-yl)cinnamate

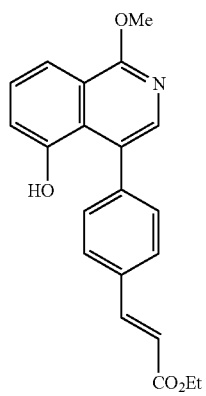

To a suspension of 60% sodium hydride in oil (301 mg, 7.52 mmol) in tetrahydrofuran (35 mL) was added dropwise ethyl diethylphosphonoacetate (853 µL, 4.30 mmol) under cooling with ice, and the mixture was stirred for 15 minutes. A solution of the compound of Referential example 8 (1.00 g, 3.58 mmol) in tetrahydrofuran (15 mL) was added dropwise thereto, and the mixture was stirred for 4 hours, while gradually returning the temperature to room temperature. The reaction mixture was poured in ice water (100 mL) and stirred for 30 minutes at room temperature. This was extracted with ethyl acetate, dried over anhydrous sodium sulfate, and then solvent was distilled off. The residue obtained was purified by silica gel column chromatography [hexane:ethyl acetate=4:1], thereby affording 947 mg of the title compound as pale yellow powder. Yield 76%.

¹H-NMR (DMSO-d₆, δ): 1.26(3H, t, J=7.3 Hz), 4.05(3H, s), 4.19(2H, q, J=7.3 Hz), 6.64(1H, d, J=15.9 Hz), 7.01(1H, d, J=7.3 Hz), 7.35(2H, d, J=7.9 Hz), 7.44(1H, t, J=7.9 Hz), 7.65-7.72(5H, m), 9.96(1H, brs).

REFERENTIAL EXAMPLE 27

5-Hydroxy-4-[4-(3-hydroxypropene-1-yl)phenyl]-1-methoxyisoquinoline

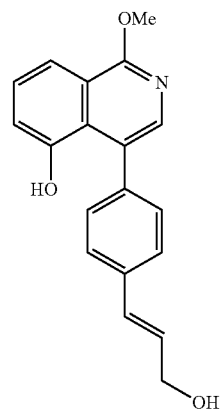

To a suspension of lithium aluminum hydride (146 mg, 3.07 mmol) in tetrahydrofuran (10 mL) was added dropwise a solution of the compound of Referential example 26 (537 mg, 1.54 mmol) in tetrahydrofuran (10 mL) under cooling with ice, and the mixture was stirred for 3 hours, while gradually returning the temperature to room temperature. Water (5 mL) and 2 mol/L aqueous solution of sodium hydroxide (1 mL) were added and the mixture was stirred for 30 minutes. This was filtered using celite and the residue was washed with ethyl acetate (20 mL). The organic layer of the filtrate was separated, washed with brine, dried over anhydrous sodium sulfate, and then solvent was distilled off. The residue obtained was purified by silica gel column chromatography [hexane:ethyl acetate=1:1], thereby affording 173 mg of the title compound as colorless powder. Yield 37%.

¹H-NMR(CDCl₃, δ): 4.15(3H, s), 4.39(2H, dt, H=5.5, 1.2 Hz), 5.48(1H, s), 6.48(1H, dt, H=15.9, 5.5 Hz), 6.71(1H, d, J=15.9 Hz), 7.10(1H, dd, J=7.3, 1.2 Hz), 7.44-7.50(3H, m), 7.54(2H, d, J=7.9 Hz), 7.73(1H, s),7.93-7.96 (1H, m).

EXAMPLE 1

1,2-Dihydro-4-[4-(dimethylaminomethyl)phenyl]-5-hydroxy-1-oxoisoquinoline

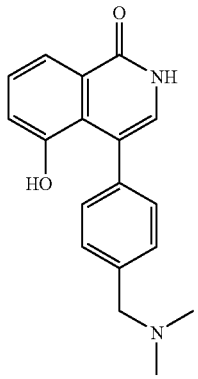

Process 1: To a solution of the compound of Referential example 8 (300 mg, 1.07 mmol) in methanol (15 mL) were added 2 mol/L dimethylamine-methanol solution (3.21 mL, 6.42 mmol) and zinc chloride (73.2 mg, 537 μmol), and the mixture was stirred for 1 hour at room temperature. To the reaction mixture was added sodium cyanoborohydride (67.2 mg, 1.07 mmol), and the mixture was stirred for 4 hours at room temperature. Water was added to the reaction mixture, which was extracted with dichloromethane, dried over anhydrous sodium sulfate, and then solvent was distilled off. A small quantity of dichloromethane was added to the residue obtained. The crystals were collected by filtration, washed with dichloromethane and then air-dried, thereby affording 262 mg of 4-[4-(dimethylaminomethyl)phenyl]-5-hydroxy-1-methoxyisoquinoline as light brown powder. Yield 79%.

$^1$H-NMR (DMSO-d$_6$, δ): 2.19(6H, s), 3.43(2H, s), 4.06 (3H, s), 7.01 (1H, d, J=7.8 Hz), 7.25(4H, s), 7.44(1H, t, J=7.8 Hz), 7.64(1H, s), 7.71 (1H, d, J=8.3 Hz), 9.88(1H, s).

Process 2: To a solution of 4-[4-(dimethylaminomethyl) phenyl]-5-hydroxy-1-methoxyisoquinoline (102 mg, 331 μmol) in acetic acid (15 mL) were added 47% hydrobromic acid (1.5 mL) and water (1.5 mL), and the mixture was refluxed for 1 hour. Water was added to the residue obtained by concentrating the reaction mixture under reduced pressure, which was made basic with saturated aqueous solution of sodium hydrogen carbonate. The precipitated crystals were collected by filtration, washed with water, and then air-dried, thereby affording 66.2 mg of the title compound as brown powder. Yield 68%.

$^1$H-NMR (DMSO-d$_6$, δ): 2.17(6H, s), 6.73(1H, d, J=5.4 Hz), 7.00(1H, d, J=6.8 Hz), 7.20(4H, s), 7.31(1H, t, J=7.8 Hz), 7.77(1H, dd, J=7.8, 1.0 Hz), 9.67(1H, bs), 11.27(1H, brs).

HR-MS (m/z): 294.1383 (+1.5 mmu).

EXAMPLES 2 THROUGH 44

Through the processes similar to Example 1, compounds listed in following Table 13 were afforded.

TABLE 13

| Example | Position | NR$^3$R$^4$ |
|---|---|---|
| 2 | 4 | NEt$_2$ |
| 3 | 4 | NPr$_2$ |
| 4 | 4 | NBu$_2$ |
| 5 | 4 | N(pentyl)$_2$ |
| 6 | 4 | N(Me)Pr |
| 7 | 4 | N(Me)Bu |
| 8 | 4 | N(Me)pentyl |
| 9 | 4 | N(Me)hexyl |
| 10 | 4 | N(CH$_2$CH$_2$OH)$_2$ |
| 11 | 4 | N(Me)Ph |
| 12 | 4 | N(Me)CH$_2$Ph |
| 13 | 4 | N(Me)CH$_2$Ph-4-OMe |
| 14 | 4 | N(Me)CH$_2$Ph-4-NMe$_2$ |
| 15 | 4 | N(Me)CH$_2$Ph-4-NH$_2$ |
| 16 | 4 | N(Et)CH$_2$Ph |
| 17 | 4 | N(CH$_2$CO$_2$H)CH$_2$Ph |
| 18 | 4 | N(CH$_2$CH$_2$NMe$_2$)CH$_2$Ph |
| 19 | 4 | N(Me)CH$_2$CH$_2$Ph |
| 20 | 4 | N(Me)CH$_2$CH$_2$Ph-4-OMe |
| 21 | 4 | N(Me)CH$_2$CH$_2$CH$_2$Ph |
| 22 | 4 | N(Me)-3-picolyl |
| 23 | 4 | N(Me)CH$_2$-cyclohexyl |
| 24 | 4 | N(Me)CH$_2$CH$_2$-cyclohexenyl |
| 25 | 4 | NHEt |
| 26 | 4 | NHPr |
| 27 | 4 | NHCH$_2$CH$_2$OH |
| 28 | 4 | NHCH$_2$CH$_2$NEt$_2$ |
| 29 | 4 | NHCH$_2$CO$_2$H |
| 30 | 4 | NHPh |
| 31 | 4 | NHCH$_2$Ph |
| 32 | 4 | pyrrolidin-1-yl |
| 33 | 4 | piperidin-1-yl |
| 34 | 4 | morpholin-1-yl |
| 35 | 4 | piperazin-1-yl |
| 36 | 4 | 1,2,3,4-tetrahydroisoquinolin-1-yl |
| 37 | 4 | 4-Ph-piperazin-1-yl |
| 38 | 4 | 4-Bn-piperazin-1-yl |
| 39 | 4 | 4-piperidinopiperidin-1-yl |
| 40 | 3 | NMe$_2$ |
| 41 | 3 | NEt$_2$ |
| 42 | 3 | NPr$_2$ |
| 43 | 3 | pyrrolidin-1-yl |
| 44 | 3 | piperidin-1-yl |

COMPOUND OF EXAMPLE 2

$^1$H-NMR (CDCl$_3$, δ): 1.07(6H, t, J=7.3 Hz), 2.57(4H, q, J=7.3 Hz), 3.64 (2H, s), 6.38(1H, brs), 7.13(1H, dd, J=7.8, 1.5 Hz), 7.40-7.46(3H, m), 7.49(2H, d, J=8.3 Hz), 8.12(1H, dd, J=8.3, 1.5 Hz), 9.38(1H, brs).

Anal. Calcd. for C$_{20}$H$_{22}$N$_2$O$_2$.¼H$_2$O: C, 73.48; H, 6.94; N, 8.57(%).

Found: C, 73.40; H, 6.83; N, 8.43(%).

HR-MS (m/z): 322.1681 (+0.0 mmu).

COMPOUND OF EXAMPLE 3

$^1$H-NMR (DMSO-d$_6$, δ): 0.85(6H, t, J=7.3 Hz), 1.43-1.48 (4H, m), 2.36 (4H, brs), 3.53(2H, s), 6.73(1H, d, J=5.9 Hz), 7.01(1H, d, J=8.3 Hz), 7.21(4H, s), 7.32(1H, t, J=8.3 Hz), 7.77(1H, d, J=7.8 Hz), 9.61(1H, s), 11.28(1H, brs).

Anal. Calcd. for $C_{22}H_{26}N_2O_2 \cdot \frac{3}{4}H_2O$: C, 72.60; H, 7.62; N, 7.70(%).
Found: C, 72.48; H, 7.25; N, 7.67(%).
HR-MS (m/z): 350.1965 (−3.0 mmu).

COMPOUND OF EXAMPLE 4

$^1$H-NMR (DMSO-$d_6$, δ): 0.86(6H, t, J=7.3 Hz), 1.24-1.33 (4H, m), 1.39-1.46(4H, m), 2.39(4H, t, J=7.3 Hz), 3.52(2H, s),6.71(1H, d, J=5.9 Hz), 7.01(1H, dd, J=7.8, 1.5 Hz), 7.20 (4H, s), 7.31(1H, t, J=7.8 Hz),7.77(1H, dd, J=7.8, 1.0 Hz), 9.58(1H, s),11.24(1H, d, J=5.4 Hz).
Anal. Calcd. for $C_{24}H_{30}N_2O_2 \cdot \frac{1}{8}H_2O$: C, 75.71; H, 8.01; N, 7.36(%).
Found: C, 75.65; H, 8.12; N, 7.32(%).
HR-MS (m/z): 378.2275 (−3.2 mmu).

COMPOUND OF EXAMPLE 5

$^1$H-NMR (DMSO-$d_6$, δ): 0.85(6H, t, J=7.3 Hz), 1.23-1.26 (6H, m), 1.42-1.45(4H, m), 2.38(4H, t, J=7.3 Hz), 3.52(2H, s), 6.71(1H, s), 7.01 (1H, dd, J=7.8, 1.0 Hz), 7.20(4H, s), 7.32(1H, t, J=7.8 Hz), 7.77(1H, dd, J=7.8, 1.0 Hz), 9.30-9.80 (1H, br), 11.10-11.40(1H, br).
Anal. Calcd. for $C_{26}H_{34}N_2O_2 \cdot \frac{1}{8}H_2O$: C, 76.39; H, 8.44; N, 6.85(%).
Found: C, 76.36; H, 8.70; N, 6.80(%).
HR-MS (m/z): 406.2613 (−0.7 mmu).

COMPOUND OF EXAMPLE 6

$^1$H-NMR (DMSO-$d_6$, δ): 0.88(3H, t, J=7.3 Hz), 1.45-1.54 (2H, m), 2.12 (3H, s), 2.31(2H, t, J=7.3 Hz), 3.45(2H, s), 6.73(1H, d, J=5.9 Hz), 7.00 (1H, d, J=7.8 Hz), 7.20(4H, s), 7.31(1H, t, J=7.8 Hz), 7.77(1H, d, J=7.8 Hz), 9.63(1H, s), 11.26(1H, d, J=4.9 Hz).
Anal. Calcd. for $C_{20}H_{22}N_2O_2 \cdot \frac{1}{10}H_2O$: C, 74.09; H, 6.90; N, 8.64(%).
Found: C, 74.17; H, 6.97; N, 8.69(%).
HR-FAB$^+$ (m/z): 323.1773 (+1.4 mmu).

COMPOUND OF EXAMPLE 7

$^1$H-NMR (DMSO-$d_6$, δ): 0.88(3H, t, J=7.3 Hz), 1.29-1.34 (2H, m), 1.42-1.48(2H, m), 2.12(3H, s), 2.34(2H, t, J=7.3 Hz), 3.45(2H, s), 6.72 (1H, d, J=5.4 Hz), 7.01(1H, d, J=7.8 Hz), 7.20(4H, s), 7.31(1H, t, J=7.8 Hz), 7.77(1H, d, J=7.8 Hz), 9.62(1H, s), 11.26(1H, d, J=4.9 Hz).
Anal. Calcd. for $C_{21}H_{24}N_2O_2 \cdot \frac{1}{10}H_2O$: C, 74.57; H, 7.21; N, 8.28(%).
Found: C, 74.50; H, 7.25; N, 8.35(%).
HR-MS (m/z): 336.1815 (−2.3 mmu).

COMPOUND OF EXAMPLE 8

$^1$H-NMR (DMSO-$d_6$, δ): 0.87(3H, t, J=6.9 Hz), 1.26-1.30 (4H, m), 1.40-1.55(2H, m), 2.11(3H, s), 2.34(2H, t, J=7.3 Hz), 3.45(2H, s), 6.73(1H, d, J=5.9 Hz), 7.00(1H, dd, J=7.8, 1.0 Hz), 7.20(4H, s), 7.32(1H, t, J=7.8 Hz), 7.77(1H, dd, J=7.8, 1.0 Hz), 9.63(1H, s), 11.27(1H, d, J=5.4 Hz).
Anal. Calcd. for $C_{22}H_{26}N_2O_2$: C, 75.40; H, 7.48; N, 7.99 (%).
Found: C, 75.21; H, 7.51; N, 8.07(%).
HR-FAB$^+$ (m/z): 351.2052 (−2.0 mmu).

COMPOUND OF EXAMPLE 9

$^1$H-NMR (DMSO-$d_6$, δ): 0.86(3H, t, J=6.9 Hz), 1.27-1.31 (6H, m), 1.44-1.47(2H, m), 2.11(3H, s), 2.34(2H, t, J=6.9 Hz), 3.45(2H, s), 6.73 (1H, d, J=5.4 Hz), 7.01(1H, d, J=7.8 Hz), 7.20(4H, s), 7.32(1H, t, J=7.8 Hz), 7.70(1H, d, J=7.8 Hz), 9.63(1H, s), 11.27(1H, d, J=4.9 Hz).
Anal. Calcd. for $C_{23}H_{28}N_2O_2 \cdot \frac{1}{10}H_2O$: C, 75.42; H, 7.76; N, 7.65(%).
Found: C, 75.35; H, 7.74; N, 7.72(%).
HR-MS (m/z): 364.2126 (−2.5 mmu).

COMPOUND OF EXAMPLE 10

$^1$H-NMR (DMSO-$d_6$, δ): 2.57(4H, t, J=6.4 Hz), 3.46-3.51 (4H, m), 3.66 (2H, s), 4.39(2H, t, J=5.4 Hz), 6.73(1H, d, J=5.9 Hz), 7.00(1H, d, J=7.8 Hz), 7.19-7.26(4H, m), 7.32(1H, t, J=7.8 Hz), 7.77(1H, d, J=7.8 Hz),9.65 (1H, s), 11.27(1H, d, J=5.9 Hz).
Anal. Calcd. for $C_{20}H_{22}N_2O_4 \cdot \frac{3}{10}H_2O$: C, 66.76; H, 6.33; N, 7.79(%).
Found: C, 66.79; H, 6.34; N, 7.66(%).
HR-FAB$^+$ (m/z): 355.1644 (−1.4 mmu).

COMPOUND OF EXAMPLE 11

$^1$H-NMR (DMSO-$d_6$, δ): 3.03(3H, s), 4.59(2H, s), 6.62 (1H, t, J=7.3 Hz), 6.71-6.76(3H, m), 6.99(1H, dd, J=7.8, 1.0 Hz), 7.11-7.22(6H, m), 7.31 (1H, t, J=7.8 Hz), 7.76(1H, dd, J=7.8, 1.0 Hz), 9.65(1H, s), 11.27(1H, d, J=5.9 Hz).
Anal. Calcd. for $C_{23}H_{20}N_2O_2 \cdot \frac{4}{5}H_2O$: C, 74.49; H, 5.87; N, 7.55(%).
Found: C, 74.42; H, 5.65; N, 7.42(%).
HR-FAB$^+$ (m/z): 357.1581 (−2.2 mmu).

COMPOUND OF EXAMPLE 12

$^1$H-NMR (DMSO-$d_6$, δ): 2.12(3H, s), 3.51(2H, s), 3.53 (2H, s),6.74 (1H, d, J=5.4 Hz), 6.99(1H, dd, J=7.8, 1.0 Hz), 7.22-7.39(10H, m), 7.77(1H, dd, J=7.8, 1.0 Hz), 9.63(1H, s), 11.26(1H, d, J=3.9 Hz).
Anal. Calcd. for $C_{24}H_{22}N_2O_2 \cdot \frac{1}{3}H_2O$: C, 76.57; H, 6.02; N, 7.44(%).
Found: C, 76.54; H, 6.01; N, 7.44(%).
HR-MS (m/z): 370.1671 (−1.0 mmu).

COMPOUND OF EXAMPLE 13

$^1$H-NMR (DMSO-$d_6$, δ): 2.09(3H, s), 3.46(2H, s), 3.48 (2H, s), 3.74(3H, s), 6.74(1H, d, J=5.4 Hz),6.91(2H, d, J=8.3 Hz),7.00(1H, d, J=7.8 Hz),7.21-7.33(7H, m), 7.75(1H, d, J=7.8 Hz), 9.63(1H, s), 11.27(1H, d, J=5.4 Hz).
Anal. Calcd. for $C_{25}H_{24}N_2O_3 \cdot \frac{1}{10}H_2O$: C, 74.64; H, 6.06; N, 6.96(%).
Found: C, 74.56; H, 6.17; N, 6.95(%).
HR-FAB$^+$ (m/z): 401.1855 (−1.1 mmu).

COMPOUND OF EXAMPLE 14

$^1$H-NMR(DMSO-$d_6$, δ): 2.08(3H, s), 2.87(6H, s), 3.41 (2H, s), 3.46(2H, s), 6.69-6.71(3H, m), 6.95(1H, d, J=7.3 Hz), 7.16(2H, d, J=8.3 Hz), 7.20-7.29(5H, m), 7.72(1H, d, J=7.3 Hz), 11.23(1H, brs).
Anal. Calcd. for $C_{26}H_{27}N_3O_2 \cdot 1H_2O$: C, 72.37; H, 6.77; N, 9.74(%).
Found: C, 72.60; H, 6.38; N, 9.73(%).
HR-MS (m/z): 413.2090 (−1.4 mmu).

COMPOUND OF EXAMPLE 15

$^1$H-NMR (DMSO-$d_6$, δ): 2.06(3H, s), 3.44(2H, s), 4.94 (2H, s), 6.53 (2H, d, J=7.8 Hz), 6.69(1H, s), 6.92(1H, brs), 7.00(2H, d, J=8.3 Hz), 7.19-7.27(5H, m), 7.69(1H, brs), 11.21(1H, brs).
HR-MS (m/z): 385.1805 (+1.5 mmu).

COMPOUND OF EXAMPLE 16

$^1$H-NMR (DMSO-$d_6$, δ): 1.04(3H, t, J=7.3 Hz), 3.56(2H, s), 3.57 (2H, s),6.73(1H, d, J=5.4 Hz), 6.99(1H, dd, J=7.8, 1.0 Hz), 7.21-7.40(10H, m),7.77(1H, dd, J=7.8, 1.0 Hz), 9.59 (1H, s), 11.25 (1H, d, J=4.9 Hz).
Anal. Calcd. for $C_{25}H_{24}N_2O_2$: C, 78.10; H, 6.29; N, 7.29 (%).
Found: C, 77.88; H, 6.47; N, 7.28(%).
HR-MS (m/z): 384.1802 (−3.5 mmu).

COMPOUND OF EXAMPLE 17

$^1$H-NMR (DMSO-$d_6$, δ): 3.20(2H, s), 3.76(2H, s), 3.79 (2H, s),6.74 (1H, d, J=5.4 Hz), 6.99(1H, d, J=7.8 Hz), 7.22-7.40(10H, m),7.77(1H, d, J=7.8 Hz), 9.64(1H, s), 11.28(1H, d, J=5.4 Hz).
Anal. Calcd. for $C_{25}H_{22}N_2O_4 \cdot 1/10 H_2O$: C, 72.14; H, 5.37; N, 6.73(%).
Found: C, 72.13; H, 5.49; N, 6.71(%).
HR-FAB$^+$ (m/z): 415.1630 (−2.8 mmu).

COMPOUND OF EXAMPLE 18

$^1$H-NMR (DMSO-$d_6$, δ): 2.10(6H, s), 3.59(2H, s), 3.60 (2H, s), 6.72-6.73(1H, m), 7.00(1H, d, J=7.8 Hz), 7.21-7.39 (10H, m), 7.77(1H, d, J=8.3 Hz), 9.60(1H, s), 11.27(1H, d, J=5.9 Hz).
Anal. Calcd. for $C_{27}H_{29}N_3O_2 \cdot 1/4 H_2O$: C, 75.06; H, 6.88; N, 9.73(%).
Found: C, 75.04; H, 6.92; N, 9.71(%).
HR-FAB$^+$ (m/z): 428.2350 (+1.2 mmu).

COMPOUND OF EXAMPLE 19

$^1$H-NMR (DMSO-$d_6$, δ): 2.21(3H, s), 2.60-2.64(2H, m), 2.80(2H, t, J=6.8 Hz), 3.54(2H, s), 6.72(1H, s), 7.00(1H, d, J=6.9 Hz), 7.15-7.33 (10H, m), 7.77(1H, d, J=8.3 Hz), 9.65 (1H, s), 11.26(1H, s).
Anal. Calcd. for $C_{25}H_{24}N_2O_2 \cdot 1/6 H_2O$: C, 77.49; H, 6.33; N, 7.23(%).
Found: C, 77.49; H, 6.41; N, 7.30(%).
HR-FAB$^+$ (m/z): 385.1923 (+0.7 mmu).

COMPOUND OF EXAMPLE 20

$^1$H-NMR (DMSO-$d_6$, δ): 2.19(3H, s), 2.55-2.59(2H, m), 2.71-2.75(2H, m), 3.53(2H, s), 3.71(3H, s), 6.73(1H, s), 6.84 (2H, d, J=8.3 Hz), 6.99-7.01(1H, m), 7.10-7.21(6H, m), 7.31 (1H, t, J=7.8 Hz), 7.77(1H, d, J=7.8 Hz), 9.30-9.80(1H, br), 11.10-11.40(1H, br).
HR-FAB$^+$ (m/z): 415.2039 (+1.8 mmu).

COMPOUND OF EXAMPLE 21

$^1$H-NMR (DMSO-$d_6$, δ): 1.76-1.81(2H, m), 2.13(3H, s), 2.38(2H, t, J=7.3 Hz), 2.62(2H, t, J=7.3 Hz), 3.46(2H, s), 6.72-6.74(1H, m), 7.01(1H, d, J=7.8 Hz), 7.15-7.34(10H, m), 7.78(1H, d, J=7.8 Hz), 9.64(1H, s), 11.28 (1H, d, J=5.4 Hz).
Anal. Calcd. for $C_{26}H_{26}N_2O_2 \cdot 1/10 H_2O$: C, 78.01; H, 6.60; N, 7.00(%).
Found: C, 78.00; H, 6.58; N, 7.06(%).
HR-FAB$^+$ (m/z): 399.2076 (+0.3 mmu).

COMPOUND OF EXAMPLE 22

$^1$H-NMR (DMSO-$d_6$, δ): 2.12(3H, s), 3.53(2H, s), 3.57 (2H, s),6.74 (1H, d, J=5.9 Hz), 7.00(1H, dd, J=7.8, 1.5 Hz), 7.22-7.28(4H, m),7.31 (1H, t, J=7.8 Hz), 7.39(1H, dd, J=7.8, 4.9 Hz), 7.76-7.79(2H, m),8.48 (1H, dd, J=4.9,2.0 Hz), 8.55 (1H, d, J=2.0 Hz), 9.63(1H, s), 11.28(1H, d, J=5.4 Hz).
Anal. Calcd. for $C_{23}H_{21}N_3O_2 \cdot 4/5 H_2O$: C, 71.60; H, 5.90; N, 10.89(%).
Found: C, 71.52; H, 5.89; N, 10.84(%).
HR-FAB$^+$ (m/z): 409.1943 (+2.7 mmu).

COMPOUND OF EXAMPLE 23

$^1$H-NMR (DMSO-$d_6$, δ): 0.70-0.90(2H, m), 1.10-1.30(3H, m), 1.50-1.70(4H, m), 1.75-1.85(2H, m), 2.10(3H, s), 2.15 (2H, d, J=7.3 Hz), 3.43(2H, s), 6.73(1H, d, J=5.4 Hz), 7.01 (1H, d, J=7.8 Hz), 7.20(4H, s), 7.32(1H, t, J=7.8 Hz), 7.76-7.78(1H, m), 9.62(1H, s), 11.27(1H, d, J=5.4 Hz).
Anal. Calcd. for $C_{24}H_{28}N_2O_2 \cdot 1/2 H_2O$: C, 74.77; H, 7.58; N, 7.27(%).
Found: C, 74.77; H, 7.37; N, 7.34(%).
HR-FAB$^+$ (m/z): 377.2219 (−1.0 mmu).

COMPOUND OF EXAMPLE 24

$^1$H-NMR (DMSO-$d_6$, δ): 1.48-1.57 (4H, m), 1.90-1.93 (4H, m), 2.10-2.13 (5H, m), 2.42-2.46(2H, m), 3.47(2H, s), 5.40(1H, s), 6.68(1H, s),6.92 (1H, s), 7.19(4H, s), 7.26(1H, t, J=7.8 Hz), 7.69(1H, d, J=7.3 Hz),10.90-11.50(1H, br).
HR-FAB$^+$ (m/z): 415.2039 (+1.8 mmu).

COMPOUND OF EXAMPLE 25

$^1$H-NMR (DMSO-$d_6$, δ): 1.23(3H, t, J=7.3 Hz), 6.73(1H, d, J=5.9 Hz), 7.06 (1H, d, J=7.3 Hz), 7.33-7.42(5H, m), 7.79(1H, d, J=7.8 Hz), 8.71(1H, brs), 9.67(1H, s), 11.36(1H, d, J=5.9 Hz).
HR-MS (m/z): 294.1383 (+1.5 mmu).

COMPOUND OF EXAMPLE 26

$^1$H-NMR (DMSO-$d_6$, δ): 0.88(3H, t, J=7.3 Hz), 1.41-1.50 (2H, m), 3.69 (2H, s), 6.71(1H, s), 7.00(1H, d, J=6.8 Hz), 7.19(2H, d, J=8.3 Hz), 7.23 (2H, d, J=8.3 Hz), 7.31(1H, t, J=7.8 Hz), 7.76-7.78(1H, m), 9.20-10.00 (1H, br), 10.90-11.60 (1H, br).
HR-MS (m/z): 308.1547 (+2.2 mmu).

COMPOUND OF EXAMPLE 27

$^1$H-NMR (DMSO-$d_6$, δ): 2.60(2H, t, J=5.9 Hz), 3.49(2H, brs), 3.72(2H, s), 7.00(1H, d, J=7.3 Hz), 7.19-7.25(4H, m), 7.31(1H, t, J=7.8 Hz), 7.77 (1H, d, J=7.8 Hz), 11.28(1H, brs).
HR-MS (m/z): 310.1307 (−1.0 mmu).

COMPOUND OF EXAMPLE 28

$^1$H-NMR (CDCl$_3$, δ): 1.03(6H, t, J=6.8 Hz), 2.58(4H, q, J=6.8 Hz), 2.63-2.76(4H, m), 3.83(2H, s), 6.77(1H, s), 7.12 (1H, d, J=7.3 Hz), 7.31-7.42(5H, m), 8.07(1H, d, J=7.3 Hz).
HR-MS (m/z): 365.2134 (+3.1 mmu).

COMPOUND OF EXAMPLE 29

$^1$H-NMR (DMSO-d$_6$, δ): 3.85(2H, s), 4.18(2H, s), 6.74 (1H, d, J=5.9 Hz), 7.06(1H, d, J=6.8 Hz), 7.33-7.41(5H, m), 7.79(1H, d, J=7.8 Hz), 9.69 (1H, s), 11.35(1H, d, J=6.3 Hz).
HR-FAB$^+$ (m/z): 325.1163 (−2.5 mmu).

COMPOUND OF EXAMPLE 30

$^1$H-NMR (CDCl$_3$, δ): 4.30(2H, s), 6.57(1H, brs), 6.67(2H, d, J=7.3 Hz), 6.71(1H, d, J=5.9 Hz), 7.00(1H, dd, J=7.8, 1.0 Hz), 7.08(2H, t, J=7.8 Hz), 7.21-7.33(5H, m), 7.77(1H, dd, J=7.8, 1.0 Hz), 9.63(1H, s), 11.28 (1H, d, J=5.9 Hz).
HR-MS (m/z): 342.1353 (−1.6 mmu).

COMPOUND OF EXAMPLE 31

$^1$H-NMR (CDCl$_3$, δ): 3.79(4H, brs), 6.72(1H, d, J=5.9 Hz), 7.01(1H, d, J=8.8 Hz), 7.23-7.41(10H, m), 7.78(1H, d, J=7.8 Hz), 9.63(1H, s), 11.29 (1H, d, J=5.4 Hz).
HR-MS (m/z): 356.1537 (+1.2 mmu).

COMPOUND OF EXAMPLE 32

$^1$H-NMR (DMSO-d$_6$, δ): 1.72(4H, s), 3.62(2H, s), 6.73 (1H, d, J=5.9 Hz), 6.99-7.01(1H, m), 7.22(4H, s), 7.32(1H, t, J=7.8 Hz), 7.76-7.78(1H, m), 9.65(1H, s), 11.28(1H, d, J=4.9 Hz).
HR-MS (m/z): 320.1518 (−0.7 mmu).

COMPOUND OF EXAMPLE 33

$^1$H-NMR (DMSO-d$_6$, δ): 1.41(2H, brs), 1.51(4H, brs), 2.35(4H, brs), 6.73 (1H, d, J=5.9 Hz), 7.00(1H, d, J=7.8 Hz), 7.20(4H, s), 7.31(1H, t, J=7.8 Hz), 7.77(1H, t, J=7.3 Hz), 9.65(1H, s), 11.27(1H, d, J=5.9 Hz).
HR-MS (m/z): 334.1694 (+1.3 mmu).

COMPOUND OF EXAMPLE 34

$^1$H-NMR (CDCl$_3$, δ): 2.49(4H, brs), 3.58(2H, s), 3.74(4H, t, J=4.9 Hz), 6.81(1H, d, J=4.9 Hz), 7.13(1H, dd, J=8.3, 1.5 Hz), 7.42-7.52(5H, m), 8.13(1H, dd, J=8.3, 1.5 Hz), 9.12(1H, brs).
Anal. Calcd. for C$_{20}$H$_{20}$N$_2$O$_3$.⅔H$_2$O: C, 68.95; H, 6.17; N, 8.04(%).
Found: C, 68.90; H, 6.15; N, 7.99(%).
HR-MS (m/z): 336.1468 (−0.6 mmu).

COMPOUND OF EXAMPLE 35

$^1$H-NMR (DMSO-d$_6$, δ): 2.45(4H, brs), 2.91(4H, t, J=4.8 Hz), 3.50(2H, s), 6.72(1H, s), 7.01(1H, dd, J=7.8, 1.5 Hz), 7.22(4H, s), 7.32(1H, t, J=7.8 Hz), 7.77(1H, dd, J=7.8, 1.5 Hz), 9.64(1H, brs), 11.28(1H, brs).
HR-MS (m/z): 335.1650 (+1.6 mmu).

COMPOUND OF EXAMPLE 36

$^1$H-NMR (DMSO-d$_6$, δ): 2.71(2H, t, J=5.9 Hz), 2.84(2H, t, J=5.9 Hz), 3.58 (2H, s), 3.67(2H, s), 6.75(1H, d, J=4.9 Hz), 7.00-7.02(2H, m), 7.09-7.11(3H, m), 7.23-7.34(5H, m), 7.78 (1H, d, J=7.8 Hz), 9.65(1H, s), 11.28(1H, d, J=5.4 Hz).
Anal. Calcd. for C$_{25}$H$_{22}$N$_2$O$_2$.⅙H$_2$O: C, 77.90; H, 5.84; N, 7.27(%).
Found: C, 77.88; H, 5.93; N, 7.31(%).
HR-MS (m/z): 382.1693 (+1.2 mmu).

COMPOUND OF EXAMPLE 37

$^1$H-NMR (DMSO-d$_6$, δ): 2.55(4H, t, J=4.9 Hz), 3.15(4H, t, J=4.9 Hz), 3.55 (2H, s), 6.74-6.79(2H, m), 6.93(2H, d, J=7.8 Hz), 7.01(1H, dd, J=7.8, 1.0 Hz), 7.19-7.24(6H, m), 7.32(1H, d, J=7.8 Hz), 7.78(1H, dd, J=7.8, 1.0 Hz), 9.67(1H, s), 11.27 (1H, d, J=5.4 Hz).
Anal. Calcd. for C$_{26}$H$_{25}$N$_3$O$_2$.⅔H$_2$O: C, 73.74; H, 6.27; N, 9.92(%).
Found: C, 73.65; H, 6.33; N, 9.70(%).
HR-FAB$^+$ (m/z): 412.1999 (−2.6 mmu).

COMPOUND OF EXAMPLE 38

$^1$H-NMR (DMSO-d$_6$, δ): 2.40(8H, brs), 3.46(2H, s), 3.47 (2H, s), 6.73 (1H, d, J=5.9 Hz), 6.99(1H, d, J=7.8 Hz), 7.20 (1H, s), 7.22-7.34(6H, m), 7.77(1H, d, J=7.8 Hz), 9.64(1H, s), 11.27(1H, d, J=5.4 Hz).
Anal. Calcd. for C$_{27}$H$_{27}$N$_3$O$_2$.⅒H$_2$O: C, 75.89; H, 6.42; N, 9.83(%).
Found: C, 75.84; H, 6.44; N, 9.77(%).
HR-MS (m/z): 425.2122 (+1.9 mmu).

COMPOUND OF EXAMPLE 39

$^1$H-NMR (DMSO-d$_6$, δ): 1.34-1.45(8H, m), 1.65(2H, d, J=11.7 Hz), 1.88 (2H, t, J=11.7 Hz), 2.14(1H, t, J=11.7 Hz), 2.41(4H, brs), 2.86(2H, d, J=11.2 Hz), 6.71(1H, s), 6.96(1H, d, J=7.3 Hz), 7.17(4H, s), 7.28(1H, t, J=7.8 Hz), 7.72(1H, d, J=7.8 Hz).
HR-FAB$^+$ (m/z): 418.2523 (+2.8 mmu).

COMPOUND OF EXAMPLE 40

$^1$H-NMR (DMSO-d$_6$, δ): 2.15(6H, s), 3.38(2H, s), 6.72 (1H, d, J=5.9 Hz), 7.02(1H, d, J=7.8 Hz), 7.14-7.17(3H, m), 7.22-7.26(1H, m), 7.32(1H, t, J=7.3 Hz), 7.78(1H, d, J=7.8 Hz), 9.62(1H, s), 11.28 (1H, d, J=4.9 Hz).
Anal. Calcd. for C$_{18}$H$_{18}$N$_2$O$_2$.⅛H$_2$O: C, 72.89; H, 6.20; N, 9.44(%).
Found: C, 72.86; H, 6.24; N, 9.45(%).

COMPOUND OF EXAMPLE 41

$^1$H-NMR (DMSO-d$_6$, δ): 0.97(6H, t, J=6.8 Hz), 3.52(2H, s), 6.71(1H, brs), 7.01(1H, d, J=7.8 Hz), 7.12(1H, d, J=6.8 Hz), 7.19-7.23(3H, m), 7.32 (1H, t, J=7.8 Hz), 7.77(1H, d, J=7.8 Hz), 11.26(1H, brs).
HR-MS (m/z): 322.1663 (−1.8 mmu).

COMPOUND OF EXAMPLE 42

$^1$H-NMR (DMSO-d$_6$, δ): 0.82(6H, t, J=6.9 Hz), 1.38-1.47 (4H, m), 2.35 (4H, t, J=7.3 Hz), 3.52(2H, s), 6.70(1H, d, J=5.4 Hz), 7.01(1H, d, J=6.9 Hz), 7.11(1H, d, J=6.9 Hz), 7.18-7.24 (3H, m), 7.32(1H, t, J=7.8 Hz), 7.77 (1H, d, J=7.8 Hz), 9.57 (1H, s), 11.24(1H, d, J=4.4 Hz).
Anal. Calcd. for C$_{22}$H$_{26}$N$_2$O$_2$.⅕H$_2$O: C, 74.63; H, 7.52; N, 7.91(%).
Found: C, 74.55; H, 7.81; N, 8.05(%).
HR-MS (m/z): 350.1974 (−2.0 mmu).

COMPOUND OF EXAMPLE 43

$^1$H-NMR (DMSO-d$_6$, δ): 1.69(4H, s), 2.44(4H, s), 3.57 (2H, s), 6.72 (1H, d, J=5.9 Hz), 7.01(1H, dd, J=7.8, 1.0 Hz), 7.13(1H, d, J=7.3 Hz), 7.17-7.25(3H, m), 7.32(1H, t, J=7.8 Hz), 7.77(1H, dd, J=7.8, 1.5 Hz), 9.63(1H, s), 11.28(1H, d, J=5.4 Hz).

Anal. Calcd. for $C_{17}H_{17}N_3O_2 \cdot 1/10 H_2O$: C, 74.56; H, 6.32; N, 8.69(%)

Found: C, 74.55; H, 6.49; N, 8.60(%).

COMPOUND OF EXAMPLE 44

$^1$H-NMR (DMSO-$d_6$, δ): 1.37-1.82(6H, m), 2.89(2H, brs), 4.29(2H, brs), 6.83(1H, brs), 7.05(1H, d, J=8.3 Hz), 7.33-7.39(5H, m), 7.80(1H, d, J=8.3 Hz), 9.17(1H, brs), 9.71(1H, s), 11.40(1H, brs).

HR-MS (m/z): 334.1700 (+1.9 mmu).

EXAMPLE 45

1,2-Dihydro-5-hydroxy-4-[4-[(4-nitrobenzyl)aminomethyl]phenyl]-1-oxoisoquinoline

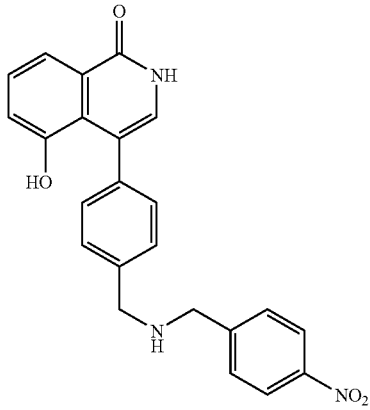

To a solution of the compound of Referential example 8 (200 mg, 716 μmol) in methanol (10 ml) were added zinc chloride (48.8 mg, 358 μmol) and successively 4-nitrobenzylamine (654 mg, 4.30 mmol), and the mixture was stirred for 1.5 hours at room temperature. To the reaction mixture was added sodium borohydride (27.1 mg, 716 μmol), and the mixture was stirred for 1 hour at room temperature. Following this, sodium borohydride (27.1 mg, 716 μmol) was added additionally, and the mixture was stirred further for 1 hour. Water was added to the reaction mixture, which was extracted with dichloromethane, dried over anhydrous sodium sulfate, and then solvent was distilled off. A mixed solution (5 mL) of acetic acid-47% hydrobromic acid-water (8:1:1) was added to the residue, and the mixture was refluxed for 1 hour. After cooling, water was added to the residue obtained by concentrating the reaction mixture under reduced pressure. After the solution was brought to pH 8 with saturated aqueous solution of sodium hydrogencarbonate, ethyl acetate was added and the mixture was stirred for 15 minutes at room temperature. The precipitated crystals were collected by filtration, washed with water and ethyl acetate in order, and then air-dried. These were submitted to silica gel column chromatography [ethyl acetate-methanol-triethylamine=10:1:1] to afford 76.2 mg of the title compound as yellowish brown powder. Yield 26%.

$^1$H-NMR (DMSO-$d_6$, δ): 3.74(2H, s), 3.88(2H, s), 6.72 (1H, d, J=5.9 Hz), 7.01-7.03(1H, m), 7.22(2H, d, J=7.8 Hz), 7.28(2H, d, J=8.3 Hz), 7.32(1H, t, J=7.8 Hz), 7.67(2H, d, J=8.8 Hz), 7.78(1H, dd, J=8.3, 1.5 Hz),8.22(2H, d, J=8.8 Hz), 9.63(1H, s), 11.28(1H, d, J=5.4 Hz).

Anal. Calcd. for $C_{23}H_{19}N_3O_4 \cdot 4/5 H_2O$: C, 66.43; H, 4.99; N, 10.11(%).

Found: C, 66.44; H, 4.75; N, 10.39(%).

HR-FAB$^+$ (m/z): 402.1439 (−1.5 mmu).

EXAMPLES 46 THROUGH 57

Through the process similar to Example 45, compounds listed in following Table 14 were afforded.

TABLE 14

| Example | R$^4$ |
|---|---|
| 46 | CH$_2$Ph-4-CO$_2$H |
| 47 | CH$_2$Ph-4-Cl |
| 48 | CH$_2$Ph-4-NMe$_2$ |
| 49 | CH$_2$Ph-4-NH$_2$ |
| 50 | CH$_2$Ph-4-OMe |
| 51 | CH$_2$Ph-3-OMe |
| 52 | CH$_2$Ph-3,4-(OMe)$_2$ |
| 53 | CH$_2$Ph-3,4,5-(OMe)$_3$ |
| 54 | CH$_2$CH$_2$Ph-4-OH |
| 55 | 4-picolyl |
| 56 | 3-picolyl |
| 57 | CH$_2$-cycloyhexyl |

COMPOUND OF EXAMPLE 46

$^1$H-NMR (DMSO-$d_6$, δ): 3.72(2H, s), 3.80(2H, s), 6.72 (1H, d, J=4.9 Hz), 7.01(2H, d, J=7.8 Hz), 7.27(2H, d, J=8.3 Hz), 7.32(1H, t, J=7.8 Hz), 7.49 (2H, d, J=8.3 Hz), 7.77(1H, d, J=8.3 Hz), 7.91(2H, d, J=7.8 Hz), 9.66(1H, s), 11.28(1H, d, J=4.4 Hz).

Anal. Calcd. for $C_{24}H_{20}N_2O_4 \cdot 2/3 H_2O$: C, 69.89; H, 5.18; N, 6.79(%).

Found: C, 69.90; H, 5.02; N, 6.77(%).

HR-FAB$^+$ (m/z): 401.1439 (−1.2 mmu).

COMPOUND OF EXAMPLE 47

$^1$H-NMR (DMSO-$d_6$, δ): 3.68(2H, s), 3.71(2H, s), 7.01 (1H, dd, J=7.8, 1.0 Hz), 7.21(2H, d, J=8.3 Hz), 7.26(2H, d, J=8.3 Hz), 7.32(1H, t, J=7.8 Hz), 7.39-7.42(4H, m), 7.77(1H, dd, J=7.8, 1.5 Hz), 9.40-9.70 (1H, br), 11.10-11.50(1H, br).

HR-FAB$^+$ (m/z): 390.1103 (−3.2 mmu).

COMPOUND OF EXAMPLE 48

$^1$H-NMR (DMSO-$d_6$, δ): 2.86(6H, s), 3.60(2H, s), 3.67 (2H, s), 6.68-6.70(2H, m), 7.00(1H, d, J=7.8 Hz), 7.17(2H, d,

J=8.8 Hz), 7.20(2H, d, J=7.8 Hz), 7.24(2H, d, J=8.3 Hz), 7.30(1H, t, J=7.8 Hz), 7.74(1H, d, J=7.8 Hz), 9.50-10.20 (1H, br), 11.10-11.50(1H, br).

HR-FAB$^+$ (m/z): 400.1999 (−2.6 mmu).

COMPOUND OF EXAMPLE 49

$^1$H-NMR (DMSO-d$_6$, δ): 3.54(2H, s), 3.67(2H, s), 4.90 (2H, s), 6.52(2H, d, J=7.8 Hz), 6.71(1H, s), 6.99-7.01(3H, m), 7.20(2H, d, J=7.8 Hz), 7.25 (2H, d, J=7.8 Hz), 7.31(1H, t, J=7.8 Hz), 7.77(1H, d, J=7.8 Hz), 9.60(1H, s), 11.25(1H, s).

Anal. Calcd. for C$_{23}$H$_{21}$N$_3$O$_2$.⅔H$_2$O: C, 72.96; H, 5.80; N, 11.10(%).

Found: C, 73.03; H, 5.81; N, 10.91(%).

HR-FAB$^+$ (m/z): 372.1711 (−0.1 mmu).

COMPOUND OF EXAMPLE 50

$^1$H-NMR (DMSO-d$_6$, δ): 3.65(2H, s), 3.68(2H, s), 3.74 (3H, s), 6.72(1H, s), 6.89(2H, d, J=8.3 Hz), 7.01(1H, d, J=7.8 Hz), 7.19-7.34(7H, m), 7.77 (1H, d, J=7.8 Hz), 9.61(1H, s), 11.26(1H, s).

Anal. Calcd. for C$_{24}$H$_{22}$N$_2$O$_3$.½H$_2$O: C, 72.89; H, 5.86; N, 7.08(%).

Found: C, 72.95; H, 5.73; N, 7.17(%).

HR-MS (m/z): 386.1607 (−2.3 mmu).

COMPOUND OF EXAMPLE 51

$^1$H-NMR (DMSO-d$_6$, δ): 3.69(4H, s), 3.75(3H, s), 6.72 (1H, s), 6.80 (1H, dd, J=7.8, 2.0 Hz), 6.94(1H, t, J=7.3 Hz), 7.01(1H, d, J=7.8 Hz), 7.20-7.27(5H, m), 7.32(1H, t, J=7.8 Hz), 7.77-7.79(1H, m), 9.50-9.70(1H, br), 11.20-11.40(1H, br).

Anal. Calcd. for C$_{24}$H$_{22}$N$_2$O$_3$.⅙H$_2$O: C, 74.02; H, 5.78; N, 7.19(%).

Found: C, 74.05; H, 5.83; N, 7.18(%).

HR-FAB$^+$ (m/z): 387.1691 (−1.8 mmu).

COMPOUND OF EXAMPLE 52

$^1$H-NMR (DMSO-d$_6$, δ): 3.65(2H, s), 3.68(2H, s), 3.73 (3H, s), 3.75(3H, s), 6.84-6.90(2H, m), 6.99-7.02(2H, m), 7.21(2H, d, J=7.8 Hz), 7.26(2H, d, J=8.3 Hz), 7.32(1H, t, J=7.8 Hz), 7.78(1H, dd, J=7.8, 1.0 Hz), 9.61(1H, s), 11.26 (1H, s).

Anal. Calcd. for C$_{25}$H$_{24}$N$_2$O$_4$.⅕H$_2$O: C, 71.48; H, 5.85; N, 6.67(%).

Found: C, 71.49; H, 5.82; N, 6.63(%).

HR-FAB$^+$ (m/z): 417.1834 (+2.0 mmu).

COMPOUND OF EXAMPLE 53

$^1$H-NMR (DMSO-d$_6$, δ): 3.63(3H, s), 3.66(2H, s), 3.70 (2H, s), 3.77(6H, s), 6.69(2H, s), 6.72(1H, s), 7.01(1H, dd, J=7.8, 1.0 Hz), 7.21(2H, d, J=7.8 Hz), 7.27(2H, d, J=8.3 Hz), 7.32(1H, t, J=7.8 Hz), 7.78(1H, dd, J=7.8, 1.0 Hz), 9.62(1H, s), 11.27(1H, s).

Anal. Calcd. for C$_{26}$H$_{26}$N$_2$O$_5$.⅕H$_2$O: C, 69.38; H, 5.91; N, 6.22(%).

Found: C, 69.35; H, 5.88; N, 6.25(%).

HR-FAB$^+$ (m/z): 447.1943 (+2.3 mmu).

COMPOUND OF EXAMPLE 54

$^1$H-NMR (DMSO-d$_6$, δ): 2.62-2.72(4H, m), 3.72(2H, s), 6.66(2H, d, J=8.3 Hz), 6.71(1H, s), 6.99-7.01(3H, m), 7.22 (2H, d, J=8.3 Hz), 7.31 (1H, t, J=7.8 Hz), 7.76-7.78(1H, m), 9.13(1H, s), 9.60(1H, brs),11.27 (1H, brs).

Anal. Calcd. for C$_{24}$H$_{22}$N$_2$O$_3$.⅕H$_2$O: C, 73.90; H, 5.79; N, 7.18(%).

Found: C, 73.86; H, 5.95; N, 7.16(%).

HR-FAB$^+$ (m/z): 387.1698 (−1.0 mmu).

COMPOUND OF EXAMPLE 55

$^1$H-NMR (DMSO-d$_6$, δ): 3.70(2H, s), 3.75(2H, s), 6.72 (1H, d, J=5.4 Hz), 7.01(1H, d, J=7.8 Hz), 7.21(2H, d, J=8.3 Hz), 7.27 (2H, d, J=8.3 Hz), 7.32(1H, t, J=7.8 Hz), 7.39(2H, d, J=5.9 Hz), 7.77-7.79 (1H, m), 8.50 (2H, d, J=5.9 Hz), 9.61(1H, s), 11.26(1H, d, J=4.9 Hz).

Anal. Calcd. for C$_{22}$H$_{19}$N$_3$O$_2$.⅓H$_2$O: C, 72.71; H, 5.45; N, 11.56(%).

Found: C, 72.71; H, 5.49; N, 11.42(%).

HR-MS (m/z): 351.1469 (−0.8 mmu).

COMPOUND OF EXAMPLE 56

$^1$H-NMR (DMSO-d$_6$, δ): 3.80(2H, s), 3.83(2H, s), 6.72 (1H, d, J=5.4 Hz), 7.03(1H, d, J=7.8 Hz), 7.24(2H, d, J=8.3 Hz), 7.29-7.34(2H, m), 7.39(1H, dd, J=7.8, 4.9 Hz), 7.77-7.83 (2H, m), 8.49(1H, d, J=4.4 Hz), 8.58 (1H, s), 9.63(1H, s), 11.29(1H, d, J=3.9 Hz).

Anal. Calcd. for C$_{22}$H$_{19}$N$_3$O$_2$.⅘H$_2$O: C, 71.07; H, 5.58; N, 11.30(%).

Found: C, 70.95; H, 5.46; N, 11.24(%).

HR-FAB$^+$ (m/z): 358.1588 (+3.3 mmu).

COMPOUND OF EXAMPLE 57

$^1$H-NMR (DMSO-d$_6$, δ): 0.80-1.00(2H, m), 1.10-1.30(3H, m), 1.40-1.50 (1H, m), 1.60-1.80(5H, m), 2.37(2H, d, J=6.9 Hz), 3.70(2H, s), 6.71(1H, s), 7.01(1H, d, J=7.8 Hz), 7.19(2H, d, J=7.8 Hz), 7.24(2H, d, J=7.8 Hz), 7.32(1H, t, J=7.8 Hz), 7.78(1H, d, J=7.8 Hz), 9.40-9.70 (1H, br),11.00-11.50(1H, br).

Anal. Calcd. for C$_{23}$H$_{26}$N$_2$O$_2$.⅓H$_2$O: C, 74.97; H, 7.29; N, 7.60(%).

Found: C, 74.85; H, 7.30; N, 7.81(%).

HR-MS (m/z): 362.1983 (−1.1 mmu).

EXAMPLE 58

1,2-Dihydro-5-hydroxy-4-[[N-(4-hydroxybenzyl)-N-methyl]aminomethyl]phenyl]-1-oxoisoquinoline

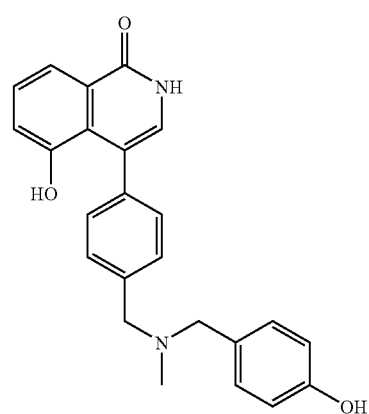

To a solution of the compound of Example 13 (168 mg, 420 μmol) in acetic acid (4 ml) was added 47% hydrobromic acid (2 ml), and the mixture was refluxed for 6 hours. After cooling, water was added to the residue obtained by concentrating the reaction mixture under reduced pressure, and the solution was brought to pH 8 with saturated aqueous solution of sodium hydrogencarbonate. This was extracted with ethyl acetate-methanol mixed solution (10:1), dried over anhydrous sodium sulfate, and then solvent was distilled off. A small quantity of ethyl acetate was added to the residue obtained. The crystals were collected by filtration, washed with ethyl acetate, and then air-dried, thereby affording 130 mg of the title compound as colorless powder. Yield 79%.

$^1$H-NMR (DMSO-$d_6$, δ): 2.08(3H, s), 3.40(2H, s), 3.47 (2H, s), 6.71-6.74(3H, m), 6.99(1H, dd, J=7.8, 1.0 Hz), 7.14 (2H, d, J=8.3 Hz), 7.21(2H, d, J=8.3 Hz), 7.25(2H, d, J=8.3 Hz), 7.31(1H, t, J=7.8 Hz), 7.77(1H, dd, J=7.8, 1.0 Hz), 9.27(1H, s), 9.63(1H, s), 11.27(1H, d, J=5.9 Hz).

Anal. Calcd. for $C_{24}H_{22}N_2O_3 \cdot \frac{1}{5}H_2O$: C, 73.90; H, 5.79; N, 7.18(%).

Found: C, 73.93; H, 5.75; N, 7.13(%).

HR-FAB$^+$ (m/z): 387.1704 (−0.4 mmu).

EXAMPLE 59

1,2-Dihydro-5-hydroxy-4-[4-[(3-hydroxybenzyl) aminomethyl]phenyl]-1-oxoisoquinoline

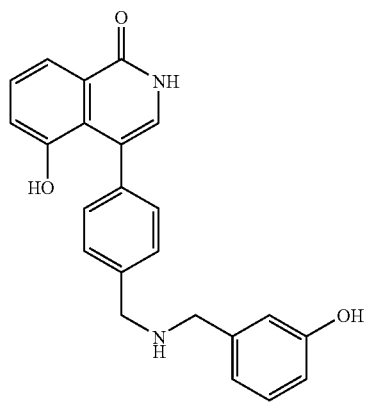

Using the compound of Example 51 (100 mg, 259 μmol), through the process similar to Example 58, 76.7 mg of the title compound were afforded as light brown powder. Yield 79%.

$^1$H-NMR (DMSO-$d_6$, δ): 3.63(2H, s), 3.68(2H, s), 6.72-6.80(3H, m), 7.00(1H, d, J=7.3 Hz), 7.08-7.11(1H, m), 7.21 (2H, d, J=6.9 Hz), 7.26 (2H, d, J=6.9 Hz), 7.32(1H, t, J=7.8 Hz), 7.77 (1H, d, J=7.3 Hz), 9.26 (1H, s), 9.62(1H, s), 11.27 (1H, s).

Anal. Calcd. for $C_{23}H_{20}N_2O_3 \cdot \frac{1}{5}H_2O$: C, 73.58; H, 5.46; N, 7.46(%).

Found: C, 73.56; H, 5.47; N, 7.41(%).

HR-FAB$^+$ (m/z): 373.1533 (−1.9 mmu).

EXAMPLE 60

1,2-Dihydro-5-hydroxy-4-[4-[(4-hydroxybenzyl) aminomethyl]phenyl]-1-oxoisoquinoline hydrobromide

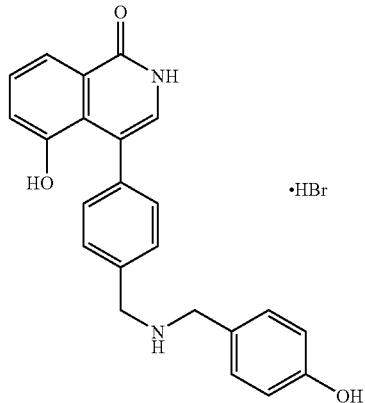

To a solution of the compound of Example 50 (195 mg, 505 μmol) in acetic acid (4 mL) was added 47% hydrobromic acid (2 mL), and the mixture was refluxed for 8 hours. After cooling, water was added to the residue obtained by concentrating the reaction mixture under reduced pressure. The precipitated crystals were collected by filtration, washed with water, and then air-dried, thereby affording 208 mg of the title compound as colorless powder. Yield 91%.

$^1$H-NMR (DMSO-$d_6$, δ): 3.98(2H, s), 4.06(2H, s), 6.73 (1H, d, J=5.4 Hz), 6.80(2H, d, J=8.3 Hz), 7.06(1H, dd, J=7.8, 1.0 Hz), 7.27-7.39 (7H, m), 7.79(1H, dd, J=7.8, 1.0 Hz), 9.61(1H, s), 9.64(1H, s), 11.33(1H, d, J=5.4 Hz).

HR-FAB$^+$ (m/z): 373.1568 (+1.6 mmu).

EXAMPLE 61

1,2-Dihydro-5-hydroxy-1-oxo-4-[4-[(4-phenyl-1,2,3,6-tetrahydropyridine-1-yl)methyl]phenyl]isoquinoline

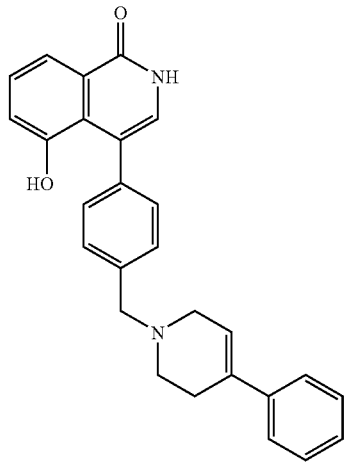

Using the compound of Referential example 8 (200 mg, 716 μmol) and 4-hydroxy-4-phenylpiperidine (762 mg, 4.30 mmol), through the process similar to Example 1, 126 mg of the title compound were afforded as colorless powder. Yield 42%.

$^1$H-NMR (DMSO-$d_6$, δ): 2.69(2H,s), 3.10(2H,d,J=2.9 Hz), 3.61(2H,s), 6.17(1H,s), 6.75(1H,d,J=3.3 Hz), 7.01(1H, d,J=7.8 Hz), 7.18-7.35(8H, m), 7.43-7.45(2H,m), 7.76-7.78 (1H,m), 9.68(1H,s), 11.27(1H,s).

Anal. Calcd. for $C_{27}H_{24}N_2O_2 \cdot \frac{3}{5}H_2O$: C, 77.34; H, 6.06; N, 6.68;(%).

Found: C, 77.31; H, 5.91; N, 6.69;(%).

HR-MS (m/z): 408.1829 (−0.9 mmu).

EXAMPLE 62

4-[4-[(4-Benzyl-1,2,3,6-tetrahydropyridine-1-yl) methyl]phenyl]-1,2-dihydro-5-hydroxy-1-oxoisoquinoline and 4-[4-[(4-benzyl-4-hydroxypiperidino) methyl]phenyl]-1,2-dihydro-5-hydroxy-1-oxoisoquinoline

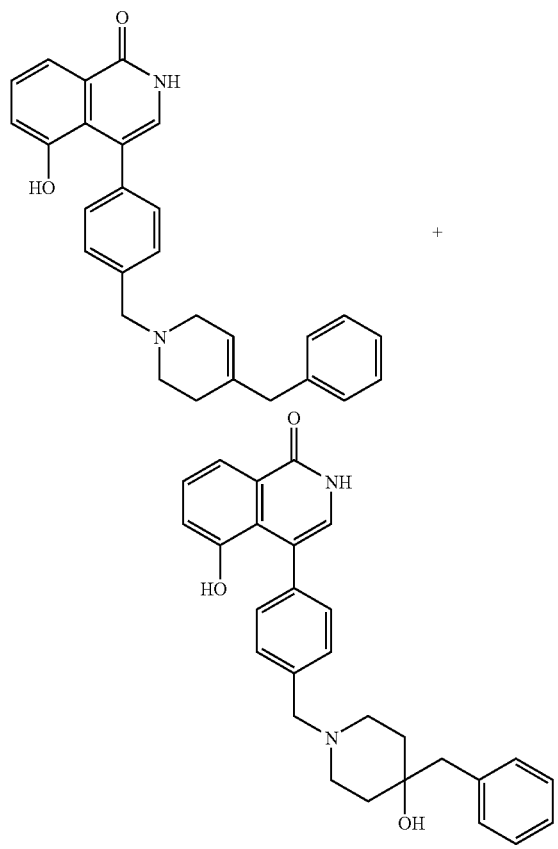

Using the compound of Referential example 8 (200 mg, 716 μmol) and 4-benzyl-4-hydroxypiperidine (822 mg, 4.30 mmol), through the process similar to Example 1, 51.9 mg (yield 17%) of 4-[4-[(4-benzyl-1,2,3,6-tetrahydropyridin-1-yl)methyl]phenyl]-1,2-dihydro-5-hydroxy-1-oxoisoquinoline and 164 mg (yield 52%) of 4-[4-[(4-benzyl-4-hydroxypiperidino)methyl]phenyl]-1,2-dihydro-5-hydroxy-1-oxoisoquinoline were afforded as colorless powder.

4-[4-[(4-Benzyl-1,2,3,6-tetrahydropyridin-1-yl)methyl]phenyl]-1,2-dihydro-5-hydroxy-1-oxoisoquinoline $^1$H-NMR (DMSO-$d_6$, δ): 1.95(2H,s), 2.89(2H,s), 3.26(2H, s), 3.52(2H,s), 5.40(1H,s), 6.72(1H,d,J=5.9 Hz), 6.98-7.00 (1H,m), 7.16-7.23(7H,m), 7.27-7.33(3H,m), 7.77(1H,dd, J=7.8,1.0 Hz), 9.63(1H,s), 11.27 (1H, d,J=5.4).

Anal. Calcd. for $C_{28}H_{26}N_2O_2 \cdot \frac{1}{2}H_2O$: C, 77.93; H, 6.31; N, 6.49;(%).

Found: C, 78.07; H, 6.32; N, 6.44;(%).

HR-FAB$^+$ (m/z): 423.2076 (+0.4 mmu).

4-[4-[(4-Benzyl-4-hydroxypiperidino)methyl]phenyl]-1,2-dihydro-5-hydroxy-1-oxoisoquinoline $^1$H-NMR(DMSO-$d_6$, δ): 1.35-1.38(2H,m), 1.47-1.54(2H, m),2.27-2.32 (2H,m), 2.67(2H,s), 3.43(2H,s), 4.14 (1H,s), 6.72(1H,d,J=5.9 Hz), 6.99-7.00(1H,m), 7.16-7.27(9H,m), 7.31 (1H,t,J=7.8 Hz),7.77(1H, dd,J=7.8,1.0 Hz), 9.62(1H,s), 11.26 (1H,d,J=5.4).

Anal. Calcd. for $C_{28}H_{28}N_2O_3 \cdot \frac{1}{5}H_2O$: C, 75.72; H, 6.45; N, 6.31;(%).

Found: C, 75.71; H, 6.52; N, 6.31;(%).

HR-MS (m/z): 441.2159 (−1.9 mmu).

EXAMPLE 63

1,2-Dihydro-4-[3-(dipropylamino)methyl-4-methoxyphenyl]-5-hydroxy-1-oxoisoquinoline

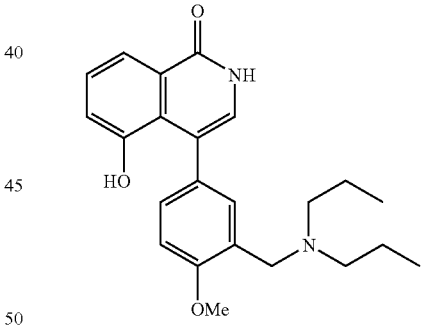

Using the compound of Referential example 11 (190 mg, 614 μmol) and dipropylamine (506 μL, 3.69 mmol), through the process similar to Example 1, 148 mg of the title compound were afforded as colorless powder. Yield 62%.

$^1$H-NMR (DMSO-$d_6$, δ): 0.80(6H,t,J=7.3 Hz), 1.36-1.43 (4H,m), 2.35 (4H,t,J=7.3 Hz), 3.51(2H,s), 3.78(2H,s), 6.67 (1H,d,J=5.9 Hz),6.87 (1H,d,J=8.3 Hz), 7.01(1H,dd,J=7.8,1.0 Hz), 7.08(1H,dd, J=8.3,2.4 Hz), 7.25(1H,d,J=2.4 Hz), 7.31 (1H,t,J=7.8 Hz), 7.75-7.77 (1H,m),9.49(1H, s), 11.20(1H,d, J=5.4 Hz).

Anal. Calcd. for $C_{23}H_{28}N_2O_3 \cdot \frac{1}{5}H_2O$: C, 71.92; H, 7.45; N, 7.29;(%).

Found: C, 71.86; H, 7.46; N, 7.14;(%).

HR-MS (m/z): 380.2090 (−1.0 mmu).

EXAMPLE 64

1,2-Dihydro-4-[3-(dipropylamino)methyl-4-hydroxyphenyl]-5-hydroxy-1-oxoisoquinoline

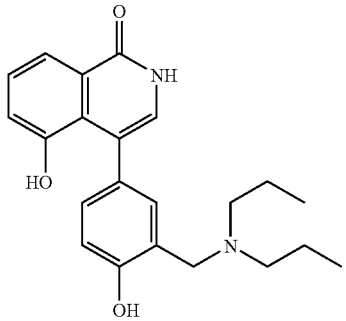

To a solution of the compound of Example 63 (84.6 mg, 222 μmol) in dichloromethane (5 mL) was added 1 mol/L boron tribromide-dichloromethane solution (1.11 mL, 1.11 mmol), and the mixture was refluxed for 24 hours. After cooling, the reaction mixture was poured in ice water and the solution was brought to pH 8 with sodium carbonate. This was extracted using dichloromethane, dried over anhydrous sodium sulfate, and then solvent was distilled off. The residue obtained was purified by Chromatolex NH column chromatography [ethyl acetate-methanol=20:1], thereby affording 69.8 mg of the title compound as colorless powder. Yield 86%.

$^1$H-NMR (DMSO-d$_6$, δ): 0.85(6H,t,J=7.3 Hz), 1.47-1.53 (4H,m), 2.42-2.46(4H,m), 3.70(2H,s), 6.62(1H,d,J=7.8 Hz), 6.67(1H,d,J=5.9 Hz), 6.95-7.01(3H,m), 7.30(1H,t,J=7.8 Hz), 7.76(1H,d,J=8.3 Hz), 9.20-9.80(1H,br), 11.19(1H,d,J=4.9 Hz).

HR-MS (m/z): 366.1954 (−1.0 mmu).

EXAMPLE 65

1,2-Dihydro-4-[4-(2-dimethylamino)ethyl-3-nitrophenyl]-5-hydroxy-1-oxoisoquinoline

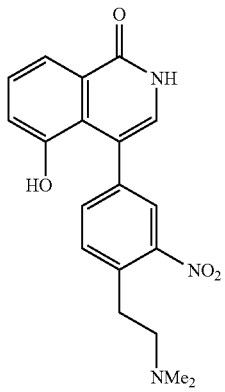

Using the compound of Referential example 13 (574 mg, 1.50 mmol), through the process similar to Example 64, 61.5 mg of the title compound were afforded as yellow powder. Yield 11%.

$^1$H-NMR (DMSO-d$_6$, δ): 2.20(6H,s), 2.98(2H,t,J=7.8 Hz), 6.89(1H,d, J=5.4 Hz), 7.04(1H,d,J=7.8 Hz), 7.35(1H,t,J=7.8 Hz), 7.45(1H,d, J=8.3 Hz), 7.55(1H,dd,J=7.8,1.5 Hz), 7.77-7.79(2H,m), 9.90(1H,s), 11.42 (1H,d,J=5.4 Hz).

Anal. Calcd. for C$_{19}$H$_{19}$N$_3$O$_4$·⅓H$_2$O: C, 63.50; H, 5.52; N, 11.69;(%).
Found: C, 63.51; H, 5.64; N, 11.53;(%).
HR-MS (m/z): 353.1413 (−1.0 mmu).

EXAMPLE 66

4-[3-Amino-4-(2-dimethylamino)ethylphenyl]-1,2-dihydro-5-hydroxy-1-oxoisoquinoline

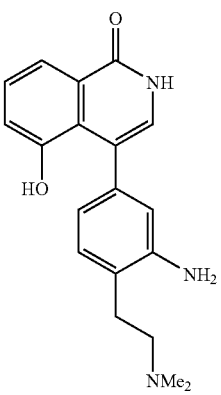

To a solution of the compound of Example 65 (46.0 mg, 130 μmol) in methanol-N,N-dimethylformamide (3:1, 4 mL) was added 10% palladium on carbon (moisture 51.1%, 5.00 mg), and the mixture was stirred for 2 hours at room temperature under hydrogen current (ambient pressure). Catalyst was filtered off using celite and solvent was distilled off. Acetone was added to the residue obtained. The crystals were collected by filtration, washed using acetone, and then air-dried, thereby affording 35.4 mg of the title compound as light brown powder.

Yield 84%.

$^1$H-NMR (DMSO-d$_6$, δ): 2.21(6H,s), 2.42(2H,t,J=7.8 Hz), 2.57(2H,t, J=7.8 Hz), 4.77(2H,s), 6.42(1H,dd,J=7.8,1.5 Hz), 6.54(1H,d,J=2.0 Hz), 6.65(1H,s), 6.84(1H,d,J=7.8 Hz), 6.95 (1H,d,J=7.3 Hz), 7.28(1H,t,J=7.8 Hz), 7.71(1H,d,J=7.3 Hz), 9.10-10.10(1H,br),10.80-11.30(1H,br).

HR-MS (m/z): 323.1647 (+1.4 mmu).

EXAMPLE 67

1,2-Dihydro-4-[[4-(2-dimethylamino)ethyl]phenyl]-5-hydroxy-1-oxoisoquinoline

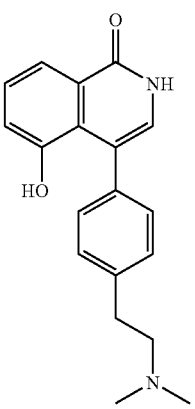

Process 1: To a solution of the compound of Referential example 17 (200 mg, 501 μmol) in tetrahydrofuran (5 mL) were added triethylamine (100 μL, 720 μmol) and methanesulfonyl chloride (60.0 μL, 780 μmol) under cooling with ice, and the mixture was stirred for 30 minutes at room temperature. Ice water was added to the reaction mixture, which was extracted with ethyl acetate, dried over anhydrous sodium sulfate, and then solvent was distilled off. The residue obtained was dissolved in N,N-dimethylformamide (10 mL) and, after 2 mol/L dimethylamine-tetrahydrofuran solution (5.00 mL, 10.0 mmol) and potassium iodide (83.2 mg, 501 μmol) were added, the mixture was stirred for 7 hours at 100° C. in a sealed tube. After cooling, water was added to the residue obtained by concentrating the reaction mixture under reduced pressure, and the solution was brought to pH 9 using sodium carbonate. This was extracted with dichloromethane, dried over anhydrous sodium sulfate, and then solvent was distilled off. The residue obtained was dissolved in ethanol (20 mL) and, after 1 mol/L aqueous solution of potassium hydroxide (5.00 mL, 5.00 mmol) was added, the mixture was refluxed for 1 hour. Water was added to the residue obtained by concentrating the reaction mixture under reduced pressure, which was extracted with dichloromethane, dried over anhydrous sodium sulfate, and then solvent was distilled off. The residue obtained was purified by silica gel column chromatography [ethyl acetate-methanol=1:1], thereby affording 98.7 mg of 4-[4-[2-(dimethylamino)ethyl]phenyl]-5-hydroxy-1-methoxyisoquinoline as pale yellow powder. Yield 61%.

$^1$H-NMR (CDCl$_3$,δ): 2.34(6H,s), 2.59-2.63(2H,m), 2.83-2.88 (2H,m), 4.15(3H,s), 7.07(1H,dd,J=7.8,1.0 Hz), 7.36 (2H,d,J=8.3 Hz), 7.41(2H, d,J=8.3 Hz), 7.47(1H,t,J=7.8 Hz), 7.72(1H,s), 7.93(1H,dd, J=8.3,1.0 Hz).

Process 2: To a solution of 4-[4-[2-(dimethylamino)ethyl]phenyl]-5-hydroxy-1-methoxyisoquinoline (91.3 mg, 283 μmol) in acetic acid (5 mL) were added 47% hydrobromic acid (0.5 mL) and water (0.5 mL), and the mixture was stirred for 1 hour at 100° C. Water was added to the residue obtained by concentrating the reaction mixture under reduced pressure. The solution was brought to pH 8 with saturated aqueous solution of sodium hydrogencarbonate and concentrated under reduced pressure. The residue obtained was purified by silica gel column chromatography [ethyl acetate-methanol=1:1], washed with ethyl acetate and water in order, and then air-dried, thereby affording 37.2 mg of the title compound as pale yellow powder. Yield 43%.

$^1$H-NMR (DMSO-d$_6$, δ): 2.20(6H,s), 2.72(2H,t,J=7.3 Hz), 6.71(1H,d, J=5.9 Hz), 6.99(1H,d,J=7.8 Hz), 7.13(2H,d,J=7.8 Hz), 7.17(2H,d, J=8.3 Hz), 7.31(1H,t,J=7.8 Hz), 7.76-7.78 (1H,m), 9.64(1H,s), 11.26 (1H,d,J=4.9 Hz).

Anal. Calcd. for C$_{19}$H$_{20}$N$_2$O$_2$·¼H$_2$O: C, 72.94; H, 6.60; N, 8.95;(%).

Found: C, 72.87; H, 6.49; N, 8.92;(%).

HR-FAB$^+$ (m/z): 309.1579 (−2.4 mmu).

EXAMPLES 68 THROUGH 92

Through the process similar to Example 67, compounds listed in following Table 15 were afforded.

TABLE 15

| Example | position | n | NR$^3$R$^4$ |
|---|---|---|---|
| 68 | 4 | 2 | NPr$_2$ |
| 69 | 4 | 2 | N(Me)Pr |
| 70 | 4 | 2 | N(Me)pentyl |
| 71 | 4 | 2 | N(Me)(CH$_2$)$_2$NMe$_2$ |
| 72 | 4 | 2 | N(Me)CH$_2$-cyclohexyl |
| 73 | 4 | 2 | N(Me)CH$_2$Ph |
| 74 | 4 | 2 | N(Me)CH$_2$Ph-4-OMe |
| 75 | 4 | 2 | N(Me)CH$_2$Ph-3-OMe |
| 76 | 4 | 2 | N(Me)CH$_2$Ph-4-NH$_2$ |
| 77 | 4 | 2 | N(Me)CH$_2$Ph-4-NMe$_2$ |
| 78 | 4 | 2 | N(Me)(CH$_2$)$_2$-cyclohexenyl |
| 79 | 4 | 2 | N(Me)(CH$_2$)$_2$Ph |
| 80 | 4 | 2 | N(Me)(CH$_2$)$_2$Ph-4-OMe |
| 81 | 4 | 2 | 1,2,3,4-tetrahydroisoquinolin-2-yl |
| 82 | 4 | 2 | 4-Ph-1,2,3,6-tetrahydropyridin-1-yl |
| 83 | 4 | 2 | 4-Bn-piperazin-1-yl |
| 84 | 3 | 2 | NMe$_2$ |
| 85 | 3 | 2 | NPr$_2$ |
| 86 | 4 | 3 | NMe$_2$ |
| 87 | 4 | 3 | NPr$_2$ |
| 88 | 4 | 3 | N(Me)(CH$_2$)$_2$NMe$_2$ |
| 89 | 4 | 3 | N(Me)CH$_2$Ph-4-OMe |
| 90 | 4 | 3 | N(Me)CH$_2$Ph-4-NMe$_2$ |
| 91 | 4 | 3 | N(Me)(CH$_2$)$_2$Ph-4-OMe |
| 92 | 4 | 3 | 4-Bn-piperazin-1-yl |

COMPOUND OF EXAMPLE 68

$^1$H-NMR (DMSO-d$_6$, δ): 0.92(6H,brs), 1.30-1.90(4H,br), 2.80-3.30 (4H,br), 6.70(1H,d,J=5.9 Hz), 7.03(1H,d,J=7.8 Hz), 7.22(4H,brs), 7.33(1H,t,J=7.8 Hz), 7.78(1H,d,J=7.8 Hz), 9.61(1H,s), 11.29(1H,d,J=5.9 Hz).

HR-FAB$^+$ (m/z): 365.2246 (+1.7 mmu).

COMPOUND OF EXAMPLE 69

$^1$H-NMR (DMSO-d$_6$, δ): 0.85(3H,t,J=7.3 Hz), 1.39-1.48 (2H,m), 2.22 (3H,s), 2.32(2H,t,J=7.3 Hz), 2.52-2.56(2H,m), 2.69-2.73(2H,m), 6.71(1H,d,J=5.4 Hz), 6.99(1H,dd,J=7.8, 1.5 Hz), 7.13(2H,d,J=8.3 Hz), 7.17(2H,d,J=8.3 Hz), 7.31(1H, t,J=7.8 Hz), 7.77(1H,dd,J=7.8,1.0 Hz), 9.62(1H,brs), 11.26 (1H,d,J=5.9 Hz).

Anal. Calcd. for C$_{21}$H$_{24}$N$_2$O$_2$: C, 74.97; H, 7.19; N, 8.33; (%).

Found: C, 74.86; H, 7.24; N, 8.39;(%).

HR-FAB$^+$ (m/z): 337.1938 (+2.2 mmu).

COMPOUND OF EXAMPLE 70

$^1$H-NMR (DMSO-d$_6$, δ): 0.87(3H,t,J=7.3 Hz), 1.23-1.32 (4H,m), 1.39-1.46(2H,m), 2.23(3H,s), 2.36(2H,brs), 2.56(2H,brs), 2.72(2H,t,J=7.8 Hz), 6.71(1H,d,J=5.9 Hz), 6.99(1H,d,J=7.8 Hz), 7.13(2H,d, J=8.3 Hz), 7.17(2H,d,J=7.8 Hz), 7.31(1H,t,J=7.8 Hz), 7.76-7.78(1H,m), 9.62 (1H,brs), 11.26(1H,d,J=5.4 Hz).

COMPOUND OF EXAMPLE 71

¹H-NMR (DMSO-d$_6$, δ): 2.14(6H,s), 2.24(3H,s), 2.30-2.34(2H,m), 2.45-2.48(2H,m), 2.56-2.60(2H,m), 2.70-2.73 (2H,m), 6.71(1H,d, J=5.4 Hz), 6.99(1H,dd,J=7.8,1.0 Hz), 7.13(2H,d,J=8.3 Hz), 7.17 (2H,d,J=8.3 Hz), 7.31(1H,t,J=7.8 Hz), 7.77(1H,dd,J=7.8,1.0 Hz), 9.50-9.80(1H,br), 11.25(1H, d,J=4.9 Hz).

Anal. Calcd. for $C_{22}H_{27}N_3O_2 \cdot \frac{1}{5}H_2O$: C, 71.59; H, 7.48; N, 11.39;(%).

Found: C, 71.57; H, 7.50; N, 11.29;(%).

HR-MS (m/z): 365.2078 (−2.6 mmu).

COMPOUND OF EXAMPLE 72

¹H-NMR (DMSO-d$_6$, δ): 0.70-1.00(2H,br), 1.10-1.30(4H, m), 1.50-1.80(6H,m), 2.00-2.40(4H,br), 2.60-2.90(2H,br), 6.70(1H,d, J=6.1 Hz), 7.00(1H,d,J=6.7 Hz), 7.10-7.25(4H, m), 7.32(1H,t,J=7.9 Hz), 7.77 (1H,d,J=7.9 Hz), 9.61(1H,s), 11.20-11.30(1H,m).

HR-FAB⁺ (m/z): 391.2389 (+0.3 mmu).

COMPOUND OF EXAMPLE 73

¹H-NMR (DMSO-d$_6$, δ): 2.20(3H,s), 2.59(2H,t,J=7.8 Hz), 2.79(2H,t, J=7.8 Hz), 3.55(2H,s), 6.71(1H,d,J=5.9 Hz), 6.98-7.00(1H,m), 7.11 (2H,d,J=8.3 Hz), 7.16(2H,d,J=8.3 Hz), 7.22-7.33(6H,m), 7.77 (1H,dd, J=7.8,1.0 Hz), 9.61(1H,s), 11.26(1H,d,J=5.4 Hz).

Anal. Calcd. for $C_{25}H_{24}N_2O_2 \cdot \frac{2}{5}H_2O$: C, 76.66; H, 6.38; N, 7.15;(%).

Found: C, 76.73; H, 6.28; N, 7.10;(%).

HR-MS (m/z): 384.1803 (−3.5 mmu).

COMPOUND OF EXAMPLE 74

¹H-NMR (DMSO-d$_6$, δ): 2.20(3H,brs), 2.54-2.58(2H,m), 2.70-2.85 (2H,m), 3.48(2H,brs), 3.73(3H,s), 6.71(1H,d,J=5.5 Hz), 6.87(2H, d,J=7.3 Hz), 6.99(1H,d,J=7.9 Hz), 7.11(2H,d, J=7.9 Hz), 7.16(2H,d, J=7.9 Hz), 7.20(2H,d,J=6.7 Hz), 7.31 (1H,t,J=7.9 Hz), 7.77(1H,d,J=7.3 Hz), 9.61(1H,s), 11.26(1H, d,J=6.1 Hz).

Anal. Calcd. for $C_{26}H_{26}N_2O_3 \cdot \frac{1}{2}H_2O$: C, 73.74; H, 6.43; N, 6.61;(%).

Found: C, 73.52; H, 6.28; N, 6.50;(%).

HR-MS (m/z): 414.1957 (+1.4 mmu).

COMPOUND OF EXAMPLE 75

¹H-NMR DMSO-d$_6$, δ): 2.22(3H,s), 2.57-2.61(2H,m), 2.77-2.81(2H,m), 3.52(2H,s), 3.72(3H,s), 6.72(1H,d,J=5.9 Hz), 6.79-6.81(1H,m), 6.85-6.87(2H,m), 6.99(1H,dd,J=7.8, 1.5 Hz), 7.11(2H,d,J=8.3 Hz), 7.16(2H, d,J=8.3 Hz), 7.22 (1H,t,J=7.8 Hz), 7.31(1H,t,J=7.8 Hz), 7.76-7.78 (1H,m), 9.61 (1H,s), 11.26(1H,d,J=5.4 Hz).

Anal. Calcd. for $C_{26}H_{26}N_2O_3 \cdot \frac{1}{5}H_2O$: C, 74.80; H, 6.36; N, 6.71;(%).

Found: C, 74.81; H, 6.35; N, 6.75;(%).

HR-MS (m/z): 414.1977 (+3.3 mmu).

COMPOUND OF EXAMPLE 76

¹H-NMR (DMSO-d$_6$, δ): 2.19(3H,brs), 2.76(2H,brs), 4.93 (2H,brs), 6.50(2H,d,J=8.3 Hz), 6.71(1H,d,J=5.9 Hz), 6.93 (2H,d,J=8.3 Hz), 6.98 (1H,d,J=7.8 Hz), 7.09(2H,d,J=8.3 Hz), 7.16(2H,d,J=8.3 Hz), 7.31(1H,t, J=7.8 Hz), 7.77(1H,d,J=7.8 Hz), 9.61(1H,s), 11.25(1H, d,J=6.3 Hz).

Anal. Calcd. for $C_{25}H_{25}N_3O_2 \cdot \frac{1}{5}H_2O$: C, 74.49; H, 6.35; N, 10.42;(%).

Found: C, 74.47; H, 6.37; N, 10.32;(%).

HR-FAB⁺ (m/z): 400.2002 (−2.3 mmu).

COMPOUND OF EXAMPLE 77

¹H-NMR (DMSO-d$_6$, δ): 2.20(3H,brs), 2.78(2H,brs), 2.87 (6H,s), 3.45 (2H,s), 6.67(2H,d,J=8.8 Hz), 6.71(1H,d,J=5.9 Hz), 6.99(1H,d,J=7.8 Hz), 7.10(4H,d,J=8.8 Hz), 7.16(2H,d, J=8.3 Hz), 7.31(1H,t, J=7.8 Hz), 7.77(1H,d,J=7.8 Hz), 9.62 (1H,s), 11.26(1H,d,J=5.9 Hz).

HR-MS (m/z): 427.2286 (+2.7 mmu).

COMPOUND OF EXAMPLE 78

¹H-NMR (DMSO-d$_6$, δ): 1.47-1.57(4H,m), 1.90-2.00(4H, m), 2.06 (2H,t, J=7.3 Hz), 2.24(3H,s), 2.45(2H,t,J=7.3 Hz), 2.57(2H,t,J=7.8 Hz), 2.72(2H,t,J=7.8 Hz), 5.40(1H,s), 6.70 (1H,d,J=5.9 Hz), 7.00 (1H,d,J=7.8 Hz), 7.13(2H,d,J=8.3 Hz), 7.17(2H,d,J=7.8 Hz), 7.31(1H,t,J=7.8 Hz), 7.77(1H,d,J=7.8 Hz), 9.62(1H,s), 11.26(1H,d,J=5.9 Hz).

HR-FAB⁺ (m/z): 403.2401 (+1.6 mmu).

COMPOUND OF EXAMPLE 79

¹H-NMR (DMSO-d$_6$, δ): 2.32(3H,s), 2.63-2.73(8H,m), 6.71(1H,d, J=5.4 Hz), 7.00(1H,d,J=7.8 Hz), 7.12-7.33(10H, m), 7.77(1H, d, J=7.8 Hz), 9.62(1H,s), 11.26(1H,d,J=5.4 Hz).

Anal. Calcd. for $C_{26}H_{26}N_2O_2 \cdot \frac{1}{5}H_2O$: C, 77.66; H, 6.62; N, 6.97;(%).

Found: C, 77.57; H, 6.65; N, 6.94;(%).

HR-FAB⁺ (m/z): 399.2053 (−2.0 mmu).

COMPOUND OF EXAMPLE 80

¹H-NMR (DMSO-d$_6$, δ): 2.74(8H,brs), 3.72(3H,s), 6.71 (1H,d,J=5.9 Hz), 6.87(2H,d,J=8.3 Hz), 7.01(1H,d,J=7.8 Hz), 7.17-7.19(6H,m), 7.32 (1H,t,J=7.8 Hz), 7.77(1H,dd,J=7.8, 1.5 Hz), 9.63(1H,s), 11.28(1H,d, J=5.4 Hz).

HR-FAB⁺ (m/z): 429.2146 (−3.2 mmu).

COMPOUND OF EXAMPLE 81

¹H-NMR (DMSO-d$_6$, δ): 2.70-2.77(4H,m), 2.82-2.88(4H, m), 3.66(2H,s), 6.72(1H,d,J=5.9 Hz), 6.99(1H,d,J=6.8 Hz), 7.07-7.13(4H,m), 7.18(4H, s), 7.31(1H,t,J=7.8 Hz), 7.77(1H, t,J=6.8 Hz), 9.63(1H,s), 11.26(1H, d,J=5.4 Hz).

Anal. Calcd. for $C_{26}H_{24}N_2O_2 \cdot \frac{1}{5}H_2O$: C, 78.05; H, 6.15; N, 7.00;(%).

Found: C, 78.03; H, 6.16; N, 6.86;(%).

HR-MS (m/z): 396.1801 (−3.7 mmu).

COMPOUND OF EXAMPLE 82

¹H-NMR (DMSO-d$_6$, δ): 2.65-2.69(2H,m), 2.74-2.77(2H, m), 2.80-2.84 (2H,m), 3.19(2H,d,J=2.4 Hz), 6.19(1H,s), 6.72 (1H,d,J=5.9 Hz), 6.99 (1H,d,J=7.8 Hz), 7.18(4H,s), 7.24(1H, t,J=7.8 Hz), 7.29-7.36(3H,m), 7.44(2H,d,J=7.3 Hz), 7.77 (1H,d,J=7.8 Hz), 9.63(1H,s), 11.26(1H,d, J=5.9 Hz).

Anal. Calcd. for $C_{28}H_{26}N_2O_2 \cdot \frac{2}{3}H_2O$: C, 77.40; H, 6.34; N, 6.45;(%).

Found: C, 77.42; H, 6.23; N, 6.54;(%).
HR-MS (m/z): 422.1951 (−4.3 mmu).

COMPOUND OF EXAMPLE 83

$^1$H-NMR (DMSO-d$_6$, δ): 2.20-2.50(8H,m), 2.73(2H,t, J=7.8 Hz), 3.46 (2H,s), 6.71(1H,d,J=5.9 Hz), 6.99(1H,dd, J=7.8,1.0 Hz), 7.13(2H,d, J=7.8 Hz), 7.17(2H,d,J=7.8 Hz), 7.22-7.34(6H,m), 7.77(1H,dd, J=7.8, 1.0 Hz), 9.61(1H,s), 11.25(1H,d,J=5.4 Hz).

Anal. Calcd. for C$_{28}$H$_{29}$N$_3$O$_2$.¼H$_2$O: C, 75.73; H, 6.70; N, 9.46;(%).

Found: C, 75.70; H, 6.74; N, 9.32;(%).
HR-MS (m/z): 439.2274 (+1.5 mmu).

COMPOUND OF EXAMPLE 84

$^1$H-NMR (DMSO-d$_6$, δ): 2.18(6H,s), 2.46(2H,t,J=7.3 Hz), 2.70(2H,t, J=7.3 Hz), 6.72(1H,d,J=5.4 Hz), 7.01(1H,dd, J=7.8,1.0 Hz), 7.07-7.11 (3H,m), 7.19(1H,t,J=7.8 Hz), 7.32 (1H,t,J=7.8 Hz), 7.77(1H,dd,J=7.8, 1.0 Hz), 9.64(1H,brs), 11.26(1H,d,J=4.9 Hz).

Anal. Calcd. for C$_{19}$H$_{20}$N$_2$O$_2$.⅓H$_2$O: C, 72.59; H, 6.63; N, 8.91;(%).

Found: C, 72.70; H, 6.63; N, 8.83;(%).
HR-MS (m/z): 308.1517 (−0.7 mmu).

COMPOUND OF EXAMPLE 85

$^1$H-NMR (DMSO-d$_6$, δ): 0.85(6H,t,J=7.3 Hz), 1.46(4H, brs), 2.67(8H, brs), 6.72(1H,d,J=5.9 Hz), 7.02(1H,d,J=7.8 Hz), 7.11-7.21(4H,m), 7.32(1H,t,J=7.8 Hz), 7.78(1H,d,J=7.8 Hz), 9.60(1H,brs), 11.29(1H, brs).

HR-MS (m/z): 364.2132 (−1.9 mmu).

COMPOUND OF EXAMPLE 86

$^1$H-NMR (DMSO-d$_6$, δ): 1.67-1.75(2H,m), 2.14(6H,s), 2.24(2H,t,J=7.3 Hz), 2.59(2H,t,J=7.8 Hz), 6.71(1H,d,J=5.9 Hz), 6.99(1H,dd,J=7.8,1.0 Hz), 7.11(2H,d,J=8.3 Hz), 7.17 (2H,d,J=7.8 Hz), 7.31(1H,t, J=7.8 Hz), 7.77(1H,dd,J=8.3,1.0 Hz), 9.62(1H,s), 11.25(1H,d, J=4.9 Hz).

Anal. Calcd. for C$_{20}$H$_{22}$N$_2$O$_2$.⅛H$_2$O: C, 73.99; H, 6.91; N, 8.63;(%).

Found: C, 73.94; H, 6.99; N, 8.59;(%).
HR-MS (m/z): 322.1707 (+2.6 mmu).

COMPOUND OF EXAMPLE 87

$^1$H-NMR (DMSO-d$_6$, δ): 0.86(6H,t,J=7.3 Hz), 1.34-1.43 (4H,m), 1.65-1.73(2H,m), 2.33(4H,t,J=7.3 Hz), 2.41(2H,t, J=6.8 Hz), 2.59(2H,t,J=7.3 Hz), 6.71(1H,d,J=5.9 Hz), 7.00 (1H,d,J=7.8 Hz), 7.11(2H,d,J=7.8 Hz), 7.17(2H,d,J=8.3 Hz), 7.31(1H,t,J=7.8 Hz), 7.76-7.78(1H,m),9.61 (1H,s), 11.25 (1H,d,J=5.4 Hz).

Anal. Calcd. for C$_{24}$H$_{30}$N$_2$O$_2$.⅘H$_2$O: C, 73.36; H, 8.11; N, 7.13;(%).

Found: C, 73.10; H, 8.06; N, 7.00;(%).
HR-MS (m/z): 378.2341 (+3.3 mmu).

COMPOUND OF EXAMPLE 88

$^1$H-NMR (DMSO-d$_6$, δ): 1.67-1.75(2H,m), 2.13(6H,s), 2.16(3H,s), 2.29-2.40(6H,m), 2.59(2H,t,J=7.3 Hz), 6.71(1H, d,J=5.4 Hz), 6.99(1H, d,J=7.8 Hz), 7.11(2H,d,J=7.8 Hz), 7.17(2H,d,J=8.3 Hz), 7.31(1H,t,J=7.8 Hz), 7.77(1H,d,J=7.8 Hz), 9.63(1H,brs), 11.25(1H,d,J=5.4 Hz).

Anal. Calcd. for C$_{23}$H$_{29}$N$_3$O$_2$.¼H$_2$O: C, 71.94; H, 7.74; N, 10.94;(%).

Found: C, 71.98; H, 7.81; N, 10.95;(%).
HR-MS (m/z): 379.2263 (+0.3 mmu).

COMPOUND OF EXAMPLE 89

$^1$H-NMR (DMSO-d$_6$, δ): 1.78(2H,brs), 2.13(3H,brs), 2.38 (2H,brs), 2.60(2H,t,J=7.8 Hz), 3.73(3H,s), 6.71(1H,d,J=5.9 Hz),6.89(2H,d,J=8.8 Hz), 7.00(1H,d,J=7.8 Hz), 7.10(2H,d, J=8.3 Hz), 7.16(2H,d, J=7.8 Hz), 7.22(2H,d,J=8.3 Hz), 7.31 (1H,t,J=7.8 Hz), 7.77(1H,d, J=7.8 Hz), 9.62(1H,s), 11.26 (1H,d,J=5.9 Hz).

Anal. Calcd. for C$_{27}$H$_{28}$N$_2$O$_3$.¹¹⁄₁₀H$_2$O: C, 72.33; H, 6.79; N, 6.25;(%).

Found: C, 72.29; H, 6.57; N, 6.33;(%).
HR-MS (m/z): 428.2100 (+0.0 mmu).

COMPOUND OF EXAMPLE 90

$^1$H-NMR (DMSO-d$_6$, δ): 1.74-1.78(2H,m), 2.09(3H,s), 2.34(2H,t,J=7.3 Hz), 2.59(2H,t,J=7.3 Hz), 2.86(6H,s), 6.68 (2H,d,J=8.8 Hz), 6.71(1H,d, J=4.4 Hz), 7.00(1H,d,J=7.8 Hz), 7.08-7.11(4H,m), 7.15(2H,d,J=7.8 Hz), 7.31(1H,t,J=7.8 Hz), 7.77(1H,d,J=8.3 Hz), 9.61 (1H,brs),11.26(1H, brs).

Anal. Calcd. for C$_{28}$H$_{31}$N$_3$O$_2$.H$_2$O: C, 73.18; H, 7.24; N, 9.14;(%).

Found: C, 73.35; H, 7.11; N, 8.88;(%).
HR-MS (m/z): 441.2381 (−3.6 mmu).

COMPOUND OF EXAMPLE 91

$^1$H-NMR (DMSO-d$_6$, δ): 1.75(2H,brs), 2.33(3H,brs), 2.55-2.68(8H, m), 3.71(3H,s), 6.71(1H,d,J=5.4 Hz), 6.85 (2H,d,J=8.8 Hz), 7.00(1H,d,J=7.8 Hz), 7.10(2H,d,J=8.8 Hz), 7.14-7.18(4H,m), 7.31(1H,t,J=7.8 Hz), 7.77(1H,d,J=7.8 Hz), 9.60(1H,s), 11.26(1H,d,J=5.4 Hz).

HR-MS (m/z): 442.2234 (−2.3 mmu).

COMPOUND OF EXAMPLE 92

$^1$H-NMR (DMSO-d$_6$, δ): 1.69-1.76(2H,m), 2.30(2H,t, J=7.8 Hz), 2.38 (8H,brs), 2.59(2H,t,J=7.8 Hz), 3.45(2H,s), 6.71(1H,s),6.99(1H,d,J=7.8 Hz), 7.10(2H,d,J=7.8 Hz), 7.16 (2H,d,J=7.8 Hz), 7.22-7.33(6H,m), 7.77(1H,dd,J=7.8,1.0 Hz), 9.59 (1H,brs), 11.24(1H,brs).

Anal. Calcd. for C$_{29}$H$_{31}$N$_3$O$_2$.⅓H$_2$O: C, 75.79; H, 6.95; N, 9.14;(%).

Found: C, 75.75; H, 7.03; N, 9.09;(%).
HR-MS (m/z): 453.2405 (−1.1 mmu).

EXAMPLE 93

1,2-Dihydro-5-hydroxy-4-[4-[2-[N-(4-hydroxybenzyl)-N-methyl]aminoethyl]phenyl]-1-oxoisoquinoline

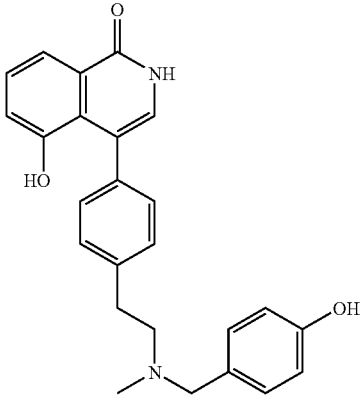

Using the compound of Example 74 (94.6 mg, 228 μmol), through the process similar to Example 58, 61.5 mg of the title compound were afforded as light brown powder. Yield 67%.

$^1$H-NMR(DMSO-$d_6$, δ): 2.94(4H,brs), 6.71(1H,d,J=5.9 Hz), 6.81(2H,brs), 7.01(1H,d,J=6.8 Hz), 7.16-7.21(6H,m), 7.32(1H,t,J=7.8 Hz), 7.77(1H,dd,J=7.8,1.0 Hz), 9.62(1H,s), 11.29(1H,d,J=5.9 Hz).

HR-FAB$^+$ (m/z): 401.1826 (−3.9 mmu).

EXAMPLE 94

1,2-Dihydro-5-hydroxy-4-[4-[2-[N-[2-(4-hydroxyphenyl)ethyl]-N-methyl]aminoethyl]phenyl]-1-oxoisoquinoline

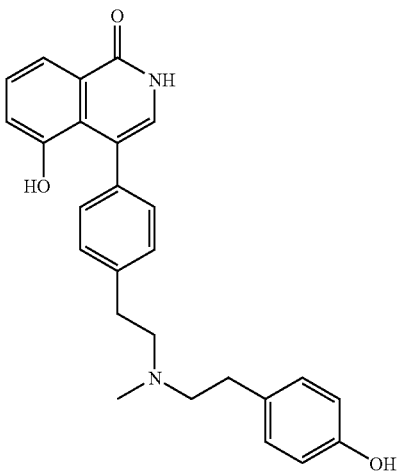

Using the compound of Example 80 (129 mg, 301 μmol), through the process similar to Example 58, 106 mg of the title compound were afforded as light brown powder. Yield 83%.

$^1$H-NMR (DMSO-$d_6$, δ): 2.31(3H,brs), 2.60-2.73(8H,m), 6.66(2H,d, J=8.3 Hz), 6.71(1H,d,J=5.4 Hz), 6.99-7.02(3H,m), 7.13(2H,d,J=8.3 Hz), 7.17(2H,d,J=8.3 Hz), 7.31(1H,t, J=7.8 Hz), 7.77(1H,d,J=7.8 Hz), 9.14 (1H,s), 9.64(1H,brs), 11.26(1H,d,J=5.4 Hz).

Anal. Calcd. for $C_{26}H_{26}N_2O_3 \cdot \frac{1}{2}H_2O$: C, 73.74; H, 6.44; N, 6.61;(%).

Found: C, 73.55; H, 6.27; N, 6.62;(%).

HR-FAB$^+$ (m/z): 415.2044 (+2.3 mmu).

EXAMPLE 95

1,2-Dihydro-5-hydroxy-4-[4-[3-[N-(4-hydroxybenzyl)-N-methyl]aminopropyl]phenyl]-1-oxoisoquinoline

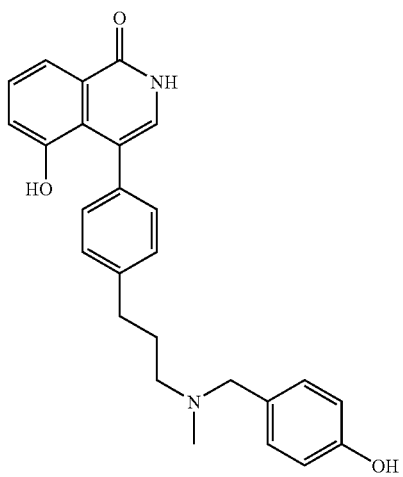

Using the compound of Example 89 (231 mg, 539 μmol), through the process similar to Example 58, 175 mg of the title compound were afforded as colorless powder. Yield 78%.

$^1$H-NMR (DMSO-$d_6$, δ): 1.81(2H,brs), 2.13(3H,brs), 2.60 (2H,t,J=7.8 Hz), 6.70-6.74(3H,m), 7.00(1H,d,J=7.3 Hz), 7.11-7.18(6H,m),7.31 (1H,t,J=7.8 Hz), 7.77(1H,d,J=7.8 Hz), 9.29(1H,brs), 9.60(1H,brs), 11.26(1H,d,J=5.9 Hz).

HR-MS (m/z): 414.1945 (+0.1 mmu).

EXAMPLE 96

1,2-Dihydro-5-hydroxy-4-[4-[3-[N-[2-(4-hydroxyphenyl)ethyl]-N-methyl]aminopropyl]phenyl]-1-oxoisoquinoline

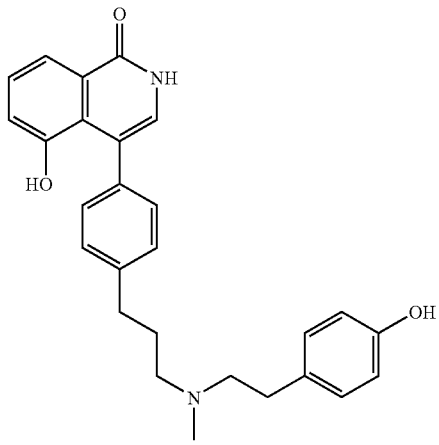

Using the compound of Example 91 (361 mg, 816 μmol), through the process similar to Example 58, 312 mg of the title compound were afforded as pale yellow powder. Yield 89%.

¹H-NMR (DMSO-d₆, δ): 1.65-1.80(2H,m), 2.24(3H,brs), 2.33(2H,brs), 2.54-2.60(6H,m), 6.66(2H,d,J=8.3 Hz), 6.71 (1H,d,J=5.9 Hz),6.99(1H,d, J=7.8 Hz), 7.00(2H,d,J=8.3 Hz), 7.09(2H,d,J=7.8 Hz), 7.16(2H,d,J=8.3 Hz), 7.31(1H,t,J=7.8 Hz), 7.77(1H,dd,J=7.8,1.0 Hz),9.12 (1H,brs), 9.66(1H,brs), 11.25(1H,d,J=5.4 Hz).

HR-FAB⁺ (m/z): 428.2122 (+2.3 mmu).

EXAMPLES 97 THROUGH 103

Using the compound of Referential example 8 or the compound of Referential example 9, through the process similar to Example 45, compounds listed in following Table 16 were afforded.

TABLE 16

| Example | Position | NR³R⁴ |
|---|---|---|
| 97 | 4 | 4-(pyrrolidin-1-yl)piperidin-1-yl |
| 98 | 4 | NH(CH₂)₃OH |
| 99 | 3 | N(Me)CH₂Ph |
| 100 | 3 | N(Me)(CH₂)₂Ph |
| 101 | 3 | N(Me)(CH₂)₃Ph |
| 102 | 3 | N(Me)Pr |
| 103 | 3 | N(Me)CH₂Ph-4-OMe |

COMPOUND OF EXAMPLE 97

¹H-NMR (DMSO-d₆, δ): 1.35-1.43(2H,m), 1.65(4H,brs), 1.80(2H,d,J=11.0 Hz), 1.93-1.99(2H,m), 2.46(4H,brs), 2.80 (2H,d,J=11.0 Hz),3.44 (2H,s), 6.73(1H,d,J=4.9 Hz), 7.01 (1H,d,J=6.7 Hz), 7.20(4H,s),7.31 (1H,t,J=7.9 Hz), 7.77(1H, d,J=7.3 Hz), 9.75(1H,brs),11.27(1H,d,J=5.5 Hz).

HR-MS (m/z): 403.2234 (−2.6 mmu).

COMPOUND OF EXAMPLE 98

¹H-NMR (DMSO-d₆, δ): 1.57-1.63(2H,m), 2.58(2H,t, J=6.7 Hz),3.48(2H, t,J=6.1 Hz), 3.68(2H,s), 6.71(1H,s), 7.00 (1H,d,J=7.9 Hz), 7.18-7.24 (4H,m), 7.31(1H,t,J=7.9 Hz), 7.77(1H,d,J=7.9 Hz), 11.25(1H,brs).

HR-MS (m/z): 324.1457 (−1.7 mmu).

COMPOUND OF EXAMPLE 99

¹H-NMR (DMSO-d₆, δ): 2.11(3H,s), 3.50(2H,s), 3.51(2H, s), 6.73(1H,d, J=5.5 Hz), 7.01(1H,d,J=7.9 Hz), 7.14-7.33 (10H,m), 7.78(1H,d,J=7.9 Hz), 9.61(1H,s), 11.27(1H,brd, J=5.5 Hz).

Anal. Calcd. for C₂₄H₂₂N₂O₂.¹/₁₀H₂O: C, 77.44; H, 6.01; N, 7.53;(%).

Found: C, 77.20; H, 6.13; N, 7.31;(%).

HR-MS (m/z): 370.1674 (−0.7 mmu).

COMPOUND OF EXAMPLE 100

¹H-NMR (DMSO-d₆, δ): 2.20(3H,s), 2.59(2H,t,J=6.7 Hz), 2.77(2H,t, J=7.3 Hz), 3.53(2H,s), 6.70(1H,d,J=5.5 Hz), 7.02 (1H,dd,J=7.9,1.2 Hz), 7.10-7.23(9H,m), 7.32(1H,t,J=7.9 Hz), 7.78(1H,dd,J=7.9,1.2 Hz),9.60 (1H,brs), 11.28(1H,brd, J=5.5 Hz).

Anal. Calcd. for C₂₅H₂₄N₂O₂.¹/₁₀H₂O: C, 77.73; H, 6.31; N, 7.25;(%).

Found: C, 77.64; H, 6.51; N, 7.04;(%).

HR-MS (m/z): 384.1867 (+3.0 mmu).

COMPOUND OF EXAMPLE 101

¹H-NMR (DMSO-d₆, δ): 1.75(2H,quin,J=7.3 Hz), 2.12 (3H,s),2.36(2H,t, J=7.3 Hz), 2.58(2H,t,J=7.3 Hz), 3.45(2H, s),6.71(1H,d,J=5.5 Hz),7.01 (1H,d,J=7.3 Hz), 7.12-7.19(6H, m), 7.22-7.26(3H,m),7.32(1H,t,J=7.9 Hz),7.77(1H,dd,J=7.9, 1.2 Hz), 9.62(1H,brs), 11.27(1H,brd,J=5.5 Hz).

Anal. Calcd. for C₂₆H₂₆N₂O₂: C, 78.36; H, 6.58; N, 7.03; (%).

Found: C, 78.19; H, 6.75; N, 6.96;(%).

HR-MS (m/z): 398.2013 (+1.9 mmu).

COMPOUND OF EXAMPLE 102

¹H-NMR (DMSO-d₆, δ): 0.85(3H,t,J=7.3 Hz),1.47(2H, quin,J=7.3 Hz), 2.12(3H,s), 2.31(2H,br), 3.45(2H,brs), 6.72 (1H,d,J=5.5 Hz), 7.01(1H, dd,J=6.7,1.2 Hz), 7.13-7.26(4H, m), 7.32(1H,t,J=7.9 Hz),7.77(1H,dd, J=6.7,1.2 Hz), 9.61(1H, brs), 11.26(1H,brd,J=5.5 Hz).

Anal. Calcd. for C₂₀H₂₂N₂O₂.³/₁₀H₂O: C, 73.28; H, 6.95; N, 8.55;(%).

Found: C, 73.05; H, 6.97; N, 8.30;(%).

HR-FAB⁺ (m/z): 323.1731 (−2.8 mmu).

COMPOUND OF EXAMPLE 103

¹H-NMR (DMSO-d₆, δ): 2.09(3H,s), 3.44(2H,s), 3.47(2H, s), 3.73(3H,s), 6.73(1H,d,J=5.5 Hz), 6.88(2H,d,J=8.6 Hz), 7.01(1H,dd,J=6.7, 1.2 Hz), 7.14-7.16(1H,m), 7.21-7.28(5H, m), 7.32(1H,t,J=7.9 Hz), 7.78(1H,dd, J=6.7,1.2 Hz), 9.61 (1H,s), 11.27(1H,brd,J=5.5 Hz).

HR-FAB⁺ (m/z): 401.1833 (−3.2 mmu).

EXAMPLE 104

1,2-Dihydro-5-hydroxy-1-oxo-4-[3-[(4-phenyl-1,2,3, 6-tetrahydropyridine-1-yl)methyl]phenyl]isoquinoline

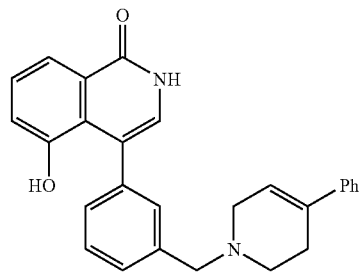

Using the compound of Referential example 9 (200 mg, 716 µmol) and 4-hydroxy-4-phenylpiperidine (762 mg, 4.30 mmol), through the process similar to Example 45, 208 mg of the title compound were afforded as brown powder. Yield 71%.

¹H-NMR (DMSO-d₆, δ): 2.46(2H,brs), 2.66(2H,t,J=5.5 Hz), 3.08(2H, d,J=2.4 Hz), 3.58(2H,s), 6.13(1H,s), 6.73(1H, s), 7.01(1H,dd,J=6.7, 1.2 Hz), 7.15-7.17(1H,m), 7.21-7.33 (8H,m), 7.39-7.41(2H,m),9.64 (1H,brs), 11.26(1H,br).

HR-FAB⁺ (m/z): 409.1915 (−0.1 mmu).

EXAMPLES 105 THROUGH 108

Using the compound of Referential example 21, through the process similar to Example 45, compounds listed in following Table 17 were afforded.

TABLE 17

| Example | NR³R⁴ |
|---|---|
| 105 | NMe₂ |
| 106 | N(Me)Bu |
| 107 | pyrrolidin-1-yl |
| 108 | N(Me)CH₂Ph |

COMPOUND OF EXAMPLE 105

¹H-NMR (DMSO-d₆, δ): 2.19(6H,s), 3.56(2H,s), 6.73(1H, d,J=3.7 Hz), 6.77(1H,d,J=3.7 Hz), 6.89(1H,s), 7.00(1H,d, J=7.3 Hz), 7.30(1H,t, J=7.3 Hz), 7.71(1H,d,J=7.3 Hz).

HR-MS (m/z): 300.0923 (−0.9 mmu).

COMPOUND OF EXAMPLE 106

¹H-NMR (DMSO-d₆, δ): 0.87(3H,t,J=7.3 Hz), 1.23-1.34 (2H,m), 1.40-1.47(2H,m), 2.17(3H,s), 2.36(2H,t,J=7.3 Hz), 3.63(2H,s), 6.73(1H,d, J=3.7 Hz), 6.77(1H,d,J=3.1 Hz), 6.90 (1H,s), 7.03(1H,d, J=7.3 Hz), 7.32(1H,t,J=7.9 Hz), 7.75(1H, d,J=7.9 Hz), 9.74(1H,s), 11.34 (1H,s).

HR-MS (m/z): 342.1385 (−1.7 mmu).

COMPOUND OF EXAMPLE 107

¹H-NMR (DMSO-d₆, δ): 1.71(4H,s), 3.74(2H,s),6.72(1H, d,J=3.1 Hz), 6.78(1H,d,J=3.1 Hz), 6.91(1H,s), 7.03(1H,d, J=7.9 Hz),7.32(1H,t, J=7.9 Hz), 7.74(1H,d,J=7.9 Hz), 9.75 (1H,s), 11.34(1H,s).

HR-MS (m/z): 326.1107 (+1.8 mmu).

COMPOUND OF EXAMPLE 108

¹H-NMR (DMSO-d₆, δ): 2.17(3H,s), 3.55(2H,s), 3.70(2H, s),6.75(1H,d, J=3.0 Hz), 6.82(1H,d,J=3.0 Hz), 6.92(1H, 7.03(1H,d,J=7.9 Hz), 7.25-7.35(7H,m), 7.75(1H,d,J=7.9 Hz), 9.75(1H,brs), 11.35(1H,brs).

HR-MS (m/z): 376.1257 (+1.1 mmu).

EXAMPLE 109

1,2-Dihydro-5-hydroxy-4-[4-[(N-methyl-N-propyl) aminomethyl]-1-naphthyl]-1-oxoisoquinoline

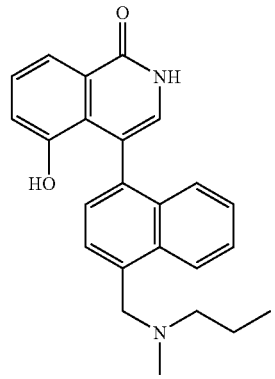

Using the compound of Referential example 23 (100 mg, 304 μmol) and N-methylpropylamine (187 μL, 1.82 mmol), through the process similar to Example 45, 25.5 mg of the title compound were afforded as grayish white powder. Yield 26%.

¹H-NMR (DMSO-d₆, δ): 0.88(3H,t,J=7.3 Hz), 1.55(2H, quin,J=7.3 Hz), 2.15(3H,s), 2.43(2H,t,J=7.3 Hz), 3.86(2H,s), 6.81-6.84(2H,m),7.27-7.35(3H,m), 7.38-7.50(3H,m), 7.81 (1H,dd,J=6.7,1.2 Hz), 8.29(1H,d, J=7.9 Hz), 9.31(1H,s), 11.34(1H,brd,J=5.5 Hz).

HR-FAB⁺ (m/z): 373.1930 (+1.4 mmu).

EXAMPLE 110

4-[4-[(N-Benzyl-N-methyl)aminomethyl]-1-naphthyl]-1,2-dihydro-5-hydroxy-1-oxoisoquinoline

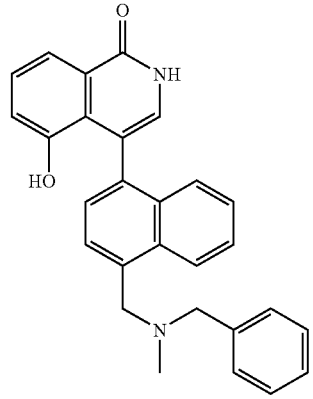

Using the compound of Referential example 23 (100 mg, 304 μmol) and N-methylbenzylamine (235 μL, 1.82 mmol), through the process similar to Example 45, 44.4 mg of the title compound were afforded as colorless powder. Yield 35%.

¹H-NMR (DMSO-d₆, δ): 2.12(3H,s), 3.63(2H,s), 3.91-3.99(2H,m), 6.81-6.83(2H,m), 7.21-7.36(8H,m), 7.44-7.53

(3H,m), 7.80(1H,d, J=7.9 Hz), 8.27(1H,d,J=8.6 Hz), 9.28 (1H,s), 11.34(1H,brd,J=5.5 Hz).

HR-MS (m/z): 421.1895 (−2.1 mmu).

EXAMPLE 111

1,2-Dihydro-5-hydroxy-1-oxo-4-[4-[(4-phenyl-1,2,3,6-tetrahydropyridine-1-yl)methyl]-1-naphthyl]isoquinoline

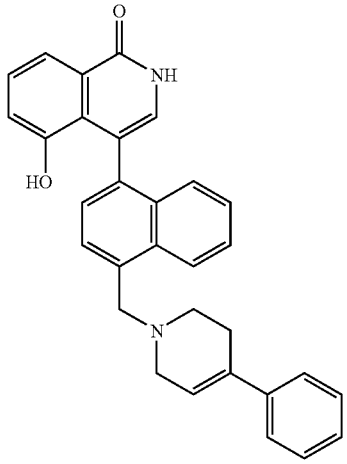

Using the compound of Referential example 23 (100 mg, 304 μmol) and 4-hydroxy-4-phenylpiperidine (323 mg, 1.82 mmol), through the process similar to Example 45, 76.4 mg of the title compound were afforded as colorless powder. Yield 55%.

$^1$H-NMR (DMSO-d$_6$, δ): 2.74-2.84(3H,m), 3.19(3H,br), 4.03(2H,s), 6.18(1H,brs), 6.83-6.84(2H,m), 7.22-7.52(11H, m), 7.15-7.17(1H,m), 7.81(1H,d,J=7.9 Hz), 8.31(1H,d,J=8.6 Hz), 9.34(1H,s), 11.35(1H,brd, J=4.9 Hz).

HR-FAB$^+$ (m/z): 459.2072 (−0.1 mmu).

EXAMPLES 112 THROUGH 116

Using the compound of Referential example 25, through the process similar to Example 45, compounds listed in following Table 18 were afforded.

TABLE 18

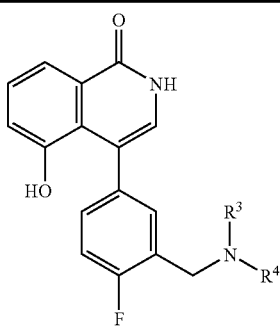

| Example | NR$^3$R$^4$ |
|---------|-------------|
| 112 | NMe$_2$ |
| 113 | N(Me)pentyl |

TABLE 18-continued

| Example | NR$^3$R$^4$ |
|---------|-------------|
| 114 | N(Me)CH$_2$Ph |
| 115 | pyrrolidin-1-yl |
| 116 | NH(CH$_2$)$_3$OMe |

COMPOUND OF 112

$^1$H-NMR (DMSO-d$_6$, δ): 2.32(6H,s), 3.63-3.65(2H,m), 6.76(1H,d,J=6.1 Hz), 7.03-7.05(1H,m), 7.11(1H,t,J=8.6 Hz), 7.23-7.26(1H,m),7.29-7.34(2H,m), 7.78(1H,dd,J=7.9,1.2 Hz), 9.70(1H,s),11.32(1H,d,J=4.9 Hz).

Anal. Calcd. for C$_{18}$H$_{17}$FN$_2$O$_2$.¾H$_2$O: C, 66.35; H, 5.72; N, 8.60;(%).

Found: C, 66.34; H, 5.54; N, 8.43;(%).

HR-MS (m/z): 312.1261 (−1.3 mmu).

COMPOUND OF EXAMPLE 113

$^1$H-NMR (DMSO-d$_6$, δ): 0.81(3H,t,J=6.7 Hz), 1.21-1.25 (4H,m), 1.42-1.45(2H,m), 2.13(3H,s), 2.33(2H,t,J=7.3 Hz), 3.49(2H,s), 6.72(1H,d, J=5.5 Hz), 7.00-7.08(2H,m), 7.15-7.19(1H,m), 7.24(1H,dd,J=7.3,2.4 Hz), 7.32(1H,t,J=7.9 Hz), 7.77(1H,d,J=7.9 Hz), 9.64(1H,s),11.28(1H, d,J=5.5 Hz).

HR-MS (m/z): 368.1884 (−1.6 mmu).

COMPOUND OF EXAMPLE 114

$^1$H-NMR (DMSO-d$_6$, δ): 2.11(3H,s), 3.54(2H,s), 3.56(2H, s), 6.75 (1H,d,J=5.5 Hz), 7.02(1H,d,J=7.3 Hz), 7.08(1H,dd, J=9.8,8.6 Hz), 7.17-7.25(2H,m), 7.28-7.34(6H,m), 7.78(1H, dd,J=7.9,1.2 Hz), 9.66 (1H,s), 11.29(1H,d,J=5.5 Hz).

Anal. Calcd. for C$_{24}$H$_{21}$FN$_2$O$_2$: C, 74.21; H, 5.45; N, 7.21; (%).

Found: C, 74.09; H, 5.46; N, 7.23;(%).

HR-MS (m/z): 388.1583 (−0.4 mmu).

COMPOUND OF EXAMPLE 115

$^1$H-NMR (DMSO-d$_6$, δ): 1.68(4H,brs), 3.63(2H,brs), 6.74 (1H,d,J=5.5 Hz), 7.01-7.08(2H,m), 7.16-7.19(1H,m), 7.26 (1H,d,J=7.3 Hz), 7.32(1H,t,J=7.9 Hz), 7.77(1H,dd,J=7.9,1.2 Hz), 9.67(1H,s), 11.28 (1H,dd,J=4.3,1.2 Hz).

Anal. Calcd. for C$_{20}$H$_{19}$FN$_2$O$_2$.⅕H$_2$O: C, 70.24; H, 5.72; N, 8.19;(%).

Found: C, 70.21; H, 5.54; N, 8.18;(%).

HR-MS (m/z): 338.1429 (−0.1 mmu).

COMPOUND OF EXAMPLE 116

¹H-NMR (DMSO-d₆, δ): 1.63(2H,t,J=6.7 Hz), 2.55(2H,t, J=6.7 Hz),3.16 (3H,s), 3.71(2H,s), 6.74(1H,s), 7.00-7.06(2H, m), 7.12-7.16 (1H,m), 7.30-7.34(2H,m), 7.77(1H,d,J=7.9 Hz), 9.50-9.90 (1H,br),11.29(1H, d,J=1.8 Hz).

HR-MS (m/z): 356.1568 (+3.2 mmu).

EXAMPLE 117

4-[4-(3-Dimethylaminopropene-1-yl)phenyl]-1,2-dihydro-5-hydroxy-1-oxoisoquinoline

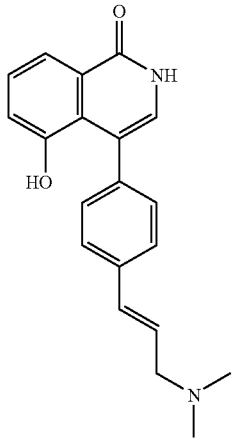

Process 1: To a solution of the compound of Referential example 27 (26.1 mg, 84.9 μmol) in dichloromethane (3 mL) was added thionyl chloride (7.44 μL, 102 μmol), and the mixture was stirred for 1 hour, while gradually returning the temperature to room temperature. Water was added to the reaction mixture, which was extracted with ethyl acetate, washed with brine, then dried over anhydrous sodium sulfate, and solvent was distilled off. After this was dissolved in tetrahydrofuran (3 mL), 2 mol/L dimethylamine-tetrahydrofuran solution (255 μL, 510 μmol) was added, and the mixture was stirred for 6 hours at 100° C. in a sealed tube. After cooling, the reaction mixture was concentrated under reduced pressure and purified by chromatolex NH column chromatography [ethyl acetate-methanol=10:1], thereby affording 17.1 mg of 4-[4-(3-dimethylaminopropene-1-yl)phenyl]-5-hydroxy-1-methoxyisoquinoline as colorless powder. Yield 60%.

¹H-NMR (CDCl₃, δ): 2.31(6H,s), 3.13(2H,d,J=6.7 Hz), 4.15(3H,s), 6.35(1H,dt,J=15.9,6.7 Hz), 6.59(1H,d,J=16.5 Hz), 7.08(1H,dd,J=7.3, 1.2 Hz), 7.43-7.53(5H,m), 7.72(1H, s), 7.93(1H,dd,J=7.9, 1.2 Hz).

Process 2: Using 4-[4-(3-dimethylaminopropene-1-yl) phenyl]-5-hydroxy-1-methoxyisoquinoline (15.0 mg, 44.9 μmol), through the process similar to Process 2 in Example 1, 12.7 mg of the title compound were afforded as light brown powder. Yield 88%.

¹H-NMR (DMSO-d₆, δ): 2.18(6H,s), 3.03(2H,d,J=6.7 Hz), 6.27(1H,dt, J=16.5,6.7 Hz), 6.54(1H,d,J=15.9 Hz), 6.74 (1H,d,J=6.1 Hz), 7.02(1H,d, J=7.3 Hz), 7.21(2H,J=8.6 Hz), 7.30-7.36(3H,m), 7.77(1H,d, J=7.3 Hz), 9.67(1H,s), 11.29 (1H,d,J=5.5 Hz).

HR-MS (m/z): 320.1501 (−2.4 mmu).

EXAMPLE 118

4-[4-[3-(Pyrrolidine-1-yl)propene-1-yl]phenyl]-1,2-dihydro-5-hydroxy-1-oxoisoquinoline

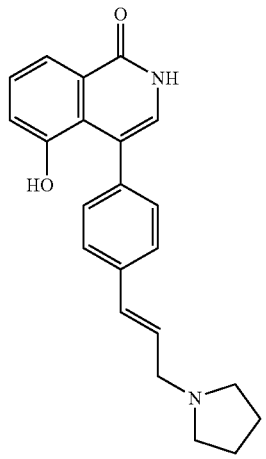

Using the compound of Referential example 27 (50.0 mg, 163 μmol) and pyrrolidine (81.6 μL, 978 μmol), through the process similar to Example 117, 17.1 mg of the title compound were afforded as colorless powder. Yield 30%.

¹H-NMR (DMSO-d₆, δ): 1.70(4H,brs), 2.47(4H,brs), 3.20 (2H,d,J=6.7 Hz), 6.32(1H,dt,J=15.9,6.7 Hz), 6.55(1H,d, J=15.9 Hz), 6.74(1H,s),7.02(1H,d,J=7.3 Hz), 7.21(2H,J=7.9 Hz), 7.30-7.36(3H,m), 7.77(1H,d,J=7.9 Hz), 9.64(1H,brs), 11.29(1H,brs).

HR-MS (m/z): 346.1670 (−1.1 mmu).

EXAMPLE 119

4-[4-[3-[(N-Benzyl-N-methyl)amino]propene-1-yl] phenyl]-1,2-dihydro-5-hydroxy-1-oxoisoquinoline

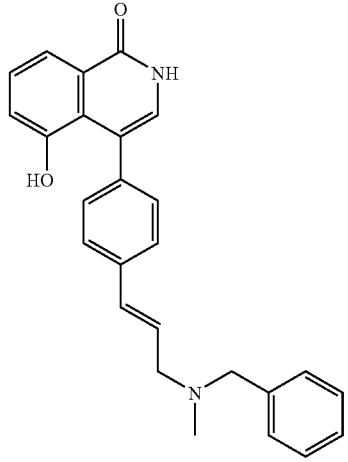

Using the compound of Referential example 27 (50.0 mg, 163 μmol) and N-methylbenzylamine (126 μL, 978 μmol), through the process similar to Example 117, 3.1 mg of the title compound were afforded as colorless powder. Yield 5%.

¹H-NMR (DMSO-d₆, δ): 2.15(3H,s), 3.17(2H,d,J=6.7 Hz), 3.53(2H,s), 6.34(1H,dt,J=15.9,6.7 Hz), 6.55-6.60(1H, m), 6.74(1H,s), 7.01(1H,d, J=7.9 Hz), 7.21(2H,d,J=7.9 Hz), 7.24-7.34(6H,m), 7.37(2H,d,J=7.9 Hz), 7.77(1H,d,J=7.9 Hz), 9.68(1H,s), 11.29(1H,s).

HR-MS (m/z): 396.1853 (+1.5 mmu).

EXAMPLE 120

4-[4-[3-(4-Phenyl-1,2,3,6-tetrahydropyridine-1-yl)propene-1-yl]phenyl]-1,2-dihydro-5-hydroxy-1-oxoisoquinoline

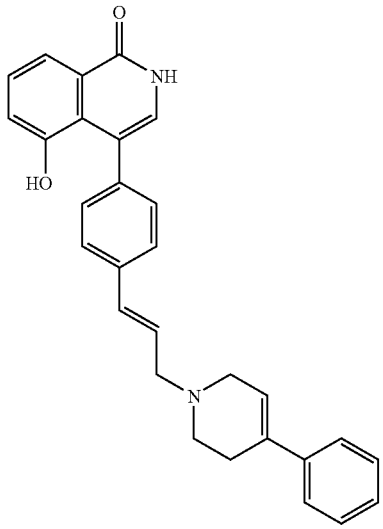

Using the compound of Referential example 27 (50.0 mg, 163 μmol) and 4-hydroxy-4-phenylpiperidine (173 mg, 978 μmol), through the process similar to Example 117, 28.5 mg of the title compound were afforded as colorless powder. Yield 40%.

$^1$H-NMR (DMSO-d$_6$, δ): 2.68-2.71(2H,m), 3.14(2H,s), 3.24(2H,d,J=6.1 Hz), 6.18(1H,s), 6.35(1H,dt,J=15.9,6.7 Hz), 6.51(1H,d,J=15.9 Hz), 6.75(1H,d,J=4.3 Hz), 7.02(1H,d, J=7.9 Hz), 7.21-7.35 (3H,m),7.38(2H, d,J=7.9 Hz), 7.44(2H, d,J=7.9 Hz), 7.78(1H,d,J=7.9 Hz), 9.68(1H,s), 11.30(1H,d, J=4.9 Hz).

HR-MS (m/z): 434.1966 (−2.8 mmu).

EXAMPLE 121

1,2-Dihydro-4-[4-(dimethylaminomethyl)phenyl]-5-hydroxy-1-oxoisoquinoline methanesulfonate

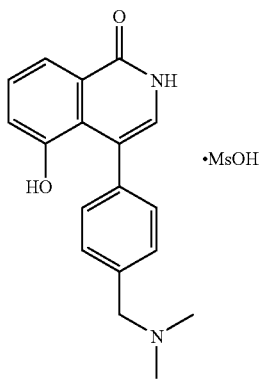

To a suspension of the compound of Example 1 (414 mg, 1.41 mmol) in methanol (15 mL) was added methanesulfonic acid (101 μL, 1.55 mmol), and the mixture was stirred for 30 minutes at room temperature. Acetone was added to the residue obtained by concentrating the reaction mixture under reduced pressure. The precipitated crystals were collected by filtration, washed with acetone, and then dried, thereby affording 492 mg of the title compound as light brown powder. Yield 88%.

$^1$H-NMR (DMSO-d$_6$, δ): 2.32(3H,s), 2.77(6H,d,J=4.9 Hz), 4.32(2H,d, J=4.9 Hz), 6.77(1H,d,J=6.1 Hz), 7.05(1H,dd, J=7.9,1.2 Hz), 7.32-7.43 (5H,m), 7.79(1H,dd,J=7.9,1.2 Hz), 9.58(1H,brs),9.70(1H,s),11.36 (1H,d,J=6.1 Hz).

Anal. Calcd. for C$_{18}$H$_{18}$N$_2$O$_2$.CH$_4$O$_3$S.⅓H$_2$O: C, 57.56; H, 5.76; N,7.07;(%).

Found: C, 57.49; H, 5.56; N, 6.85;(%).

EXAMPLE 122

1,2-Dihydro-4-[4-(dimethylaminomethyl)phenyl]-5-hydroxy-1-oxoisoquinoline hydrochloride

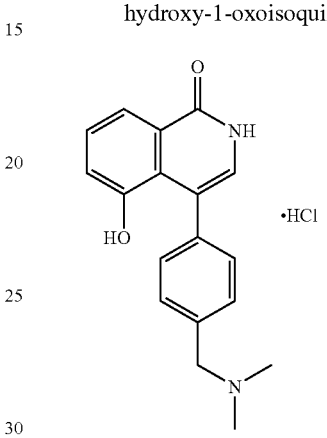

To a suspension of the compound of Example 1 (200 mg, 679 μmol) in methanol (10 mL) was used 1 mol/L hydrochloric acid (679 μL,679 μmol), and, through the process similar to Example 121, 237 mg of the title compound were afforded as light brown powder. Yield quantitative.

$^1$H-NMR (DMSO-d$_6$,δ): 2.71(6H,d,J=4.9 Hz), 4.29(2H,d, J=5.5 Hz),6.77 (1H,d,J=5.5 Hz), 7.08(1H,dd,J=7.9,1.2 Hz), 7.34(1H,t,J=7.9 Hz),7.36 (2H,d,J=7.9 Hz), 7.48(2H,d,J=7.9 Hz), 7.78(1H,dd,J=7.9,1.2 Hz),9.79 (1H,s), 10.63(1H,brs), 11.37(1H,d,J=5.5 Hz).

Anal. Calcd. for C$_{18}$H$_{18}$N$_2$O$_2$.HCl.H$_2$O: C, 61.98; H, 6.07; N, 8.03;(%).

Found: C, 61.94; H, 5.75; N, 7.77;(%).

EXAMPLE 123

1,2-Dihydro-4-[4-(dimethylaminomethyl)phenyl]-5-hydroxy-1-oxoisoquinoline hydrobromide

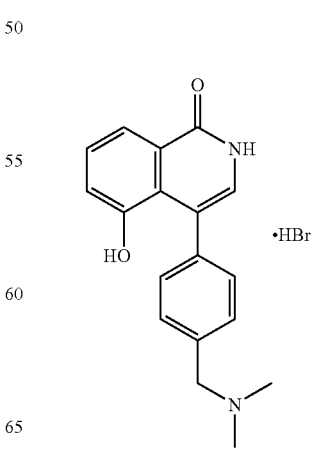

To a suspension of the compound of Example 1 (200 mg, 679 μmol) in methanol (10 mL) was used 1 mol/L hydrobromic acid (679 μL, 679 μmol), and, through the process similar to Example 121, 250 mg of the title compound were afforded as light brown powder. Yield 97%.

$^1$H-NMR (DMSO-$d_6$, δ): 2.69(6H,s), 4.21(2H,s), 6.77(1H, d,J=5.5 Hz), 7.04-7.06(1H,m), 7.32-7.41(5H,m), 7.79(1H,d, J=6.7 Hz),9.69(1H, s), 9.40-10.00(1H,br), 11.35(1H,d,J=5.5 Hz).

Anal. Calcd. for $C_{18}H_{18}N_2O_2$·HBr·⅓$H_2O$: C, 57.07; H, 5.16; N, 7.39;(%).

Found: C, 57.07; H, 5.32; N, 7.05;(%).

TEST EXAMPLE

Inhibitory Experiment Against PARP Activity

PARP (Trevigen 4667-050-01) was diluted 35 times with a buffer consisting of 50 mmol/L Tris-HCl (pH 7.8), 100 mmol/L KCl and 1 mmol/L dithiothreitol to use for the experiment. In a plastic test tube were placed 76.5 μL of buffer consisting of 117.6 mmol/L Tris-HCl (pH 8.0), 11.8 mmol/L $MgCl_2$, 5.9 mM dithiothreitol and 0.4 mmol/L NAD, 2.5 μL of [$^{14}$C]NAD (NEN Life Science Products, Inc. NEC743, 370 kBq/mL), 1 μL of activated DNA (Trevigen 4667-50-06), testing compound or 10 μL of solvent for testing compound and 10 μL of the 35 times diluted PARP solution. After mixing well, the contents were warmed to 25° C. in a water bath. After 10 minutes, the reaction was stopped by adding 1 mL of ice-cold 20% trichloroacetic acid and the test tube was left on ice. The precipitates were collected on a glass fiber filter by suction filtration and washed 5 times with 5% trichloroacetic acid. The radioactivity on the filter was measured with liquid scintillation counter. The enzyme activity in the absence of testing compound was made to be 100%, and the concentration to decrease this to 50% ($IC_{50}$ value) was calculated.

TABLE 19

| Example | $NR^3R^4$ | $IC_{50}$ (nmol/L) |
|---|---|---|
| 1 | $NMe_2$ | 30 |
| 12 | $N(Me)CH_2Ph$ | 54 |
| 19 | $N(Me)(CH_2)_2Ph$ | 41 |
| 21 | $N(Me)(CH_2)_3Ph$ | 47 |
| 23 | $N(Me)CH_2$-cyclohexyl | 126 |
| 32 | pyrrolidin-1-yl | 33 |
| 61 | 4-Ph-1,2,3,6-tetrahydropyridin-1-yl | 20 |

Results of this test are shown in Table 19. From these results, it was confirmed that the novel 4-substituted aryl-5-hydroxyisoquinolinone derivatives and their salts of the invention have excellent PARP inhibitory activity.

INDUSTRIAL APPLICABILITY

Based on the fact as above, the inventive compounds are novel 4-substituted aryl-5-hydroxyisoquinolinone derivatives and their salts, which have excellent PARP inhibitory activity. The inventive compounds with PARP inhibitory activity are useful as a preventive and/or therapeutic drugs for the diseases originating from excessive activation of PARP, for example, various ischemic diseases (cerebral infarction, cardiac infarction, acute renal failure, etc.), inflammatory diseases (inflammatory enteric disease, multiple cerebrosclerosis, arthritis, chronic rheumatism, etc.), nerve-degenerative diseases (Alzheimer's disease, Huntington's chorea, Parkinson disease, etc.), diabetes, septic shock, cephalic injury and the like.

The invention claimed is:

1. A 4-substituted aryl-5-hydroxyisoquinolinone compound represented by a formula (1)

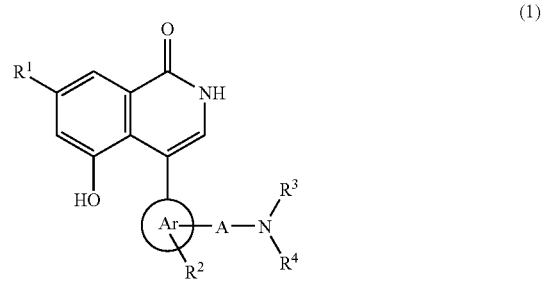

wherein ring Ar denotes a phenyl group, naphthyl group, 5- or 6-membered aromatic heterocycle or its condensed ring, R1 denotes a hydrogen atom or halogen atom, R2 denotes a hydrogen atom, halogen atom, hydroxy group, lower alkyl group which may be substituted with halogen atom, cycloalkyl group which may be substituted with halogen atom, lower alkoxy group which may be substituted with halogen atom, aralkyloxy group which may have substituents, nitro group, amino group which may have substituents, aralkyl group which may have substituents, phenyl group which may have substituents, naphthyl group which may have substituents, or 5-or 6-membered heterocycle which may have substituents and its condensed ring, A denotes a C1~C4 alkylene or C2~C4 alkenylene, R3 denotes a hydrogen atom, lower alkyl group which may be substituted with halogen atom, or formula (2)

$$-Q^1-R^5 \qquad (2)$$

wherein Q1 denotes a C1~C4 alkylene, and R5 denotes a hydroxy group, lower alkoxy group which may be substituted with halogen atom, amino group which may have substituents, lower alkoxycarbonyl group or carboxy group, R4 denotes a lower alkyl group which may be substituted with halogen atom, cycloalkyl group which may have substituents, phenyl group which may have substituents, naphthyl group which may have substituents, or 5- or 6-membered heterocycle which may have substituents and its condensed ring, formula (3)

$$-Q^2R^6 \qquad (3)$$

wherein Q2 denotes a C1~C4 alkylene, and R6 denotes a hydroxy group, lower alkoxy group which may be substituted with halogen atom, lower alkoxycarbonyl group, carboxy group, cycloalkyl group which may have substituents, cycloalkenyl group which may have substituents, phenyl group which may have substituents, naphthyl group which may have substituents, or 5- or 6-membered heterocycle which may have substituents and its condensed ring, or formula (4)

(4)

wherein R7 and R8 denote identically or differently hydrogen atoms, lower alkyl groups which may be substituted with halogenatom, aralkyl groups which may have substituents, or R7 and R8 are bound together to form a 5- or 6-membered heterocycle which may have substituents and its condensed ring, or R3 with R4 are bound together to form a 5- or 6-membered heterocycle which may have substituents and its condensed ring, or a pharmacologically acceptable addition salt thereof.

2. The 4-substituted aryl-5-hydroxyisoquinolinone compound of claim 1, represented by a formula (1a)

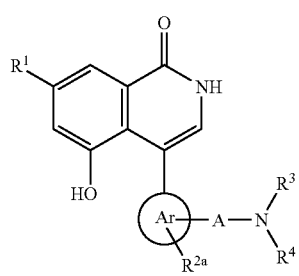

(1a)

wherein ring Ar denotes a phenyl group, naphthyl group, 5- or 6-membered aromatic heterocycle or its condensed ring, R1 denotes a hydrogen atom or halogen atom, R2a denotes a hydrogen atom, halogen atom, hydroxy group, lower alkyl group which may be substituted with halogen atom, lower alkoxy group which may be substituted with halogen atom, nitro group, or amino group which may have substituents, A denotes a C1~C4 alkylene or C2~C4 alkenylene, R3 denotes a hydrogen atom, lower alkyl group which may be substituted with halogen atom, or formula (2)

-Q$^1$-R$^5$ (2)

wherein Q1 denotes a C1~4 alkylene, and R5 denotes a hydroxy group, lower alkoxy group which may be substituted with halogen atom, amino group which may have substituents, lower alkoxycarbonyl group or carboxy group, R4 denotes a lower alkyl group which may be substituted with halogen atom, cycloalkyl group which may have substituents, phenyl group which may have substituents, naphthyl group which may have substituents, or 5- or 6-membered heterocycle which may have substituents and its condensed ring, formula (3)

-Q$^2$-R$^6$ (3)

wherein Q2 denotes a C1~C4 alkylene, and R6 denotes a hydroxy group, lower alkoxy group which may be substituted with halogen atom, lower alkoxycarbonyl group, carboxy group, cycloalkyl group which may have substituents, cycloalkenyl group which may have substituents, phenyl group which may have substituents, naphthyl group which may have substituents, or 5- or 6-membered heterocycle which may have substituents and its condensed ring, or formula (4)

(4)

wherein R7 and R8 denote identically or differently hydrogen atoms, lower alkyl groups which may be substituted with halogenatom, aralkyl groups which may have substituents, or R7 and R8 are bound together to form a 5- or 6- membered heterocycle which may have substituents and its condensed ring, or R3 and R4 are bound together to form a 5- or 6-membered heterocycle which may have substituents and its condensed ring, or a pharmacologically acceptable addition salt thereof.

3. The 4-substituted aryl-5-hydroxyisoquinolinone compound of claim 1, represented by a formula (1b)

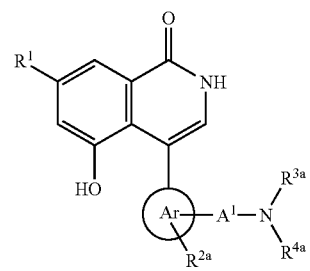

(1b)

wherein ring Ar denotes a phenyl group, naphthyl group, 5- or 6-membered aromatic heterocycle or its condensed ring, R1 denotes a hydrogen atom or halogen atom, R2a denotes a hydrogen atom, halogen atom, hydroxy group, lower alkyl group which may be substituted with halogen atom, lower alkoxy group which may be substituted with halogen atom, nitro group, or amino group which may have substituents, A1 denotes a C1~C4 alkylene, R3a denotes a hydrogen atom or lower alkyl group which may be substituted with halogen atom, R4a denotes a lower alkyl group which may be substituted with halogen atom, cycloalkyl group which may have substituents, formula (3)

-Q$^2$R$^6$ (3)

wherein Q2 denotes a C1~C4 alkylene, and R6 denotes a hydroxy group, lower alkoxy group which may be substituted with halogen atom, lower alkoxycarbonyl group, carboxy group, cycloalkyl group which may have substituents, cycloalkenyl group which may have substituents, phenyl group which may have substituents, naphthyl group which may have substituents, or 5- or 6-membered heterocycle which may have substituents and its condensed ring, or formula (4)

(4)

wherein R7 and R8 denote identically or differently hydrogen atoms, lower alkyl groups which may be substituted with halogenatom, aralkyl groups which may have substituents, or R7 and R8 are bound together to form a 5- or 6- membered heterocycle which may have substituents and its condensed ring, or R3a and R4a are bound together to form a 5- or 6-membered heterocycle which may have substituents and its condensed ring, or a pharmacologically acceptable addition salt thereof.

4. The 4-substituted aryl-5-hydroxyisoquinolinone compound of claim 1, represented by a formula (1c)

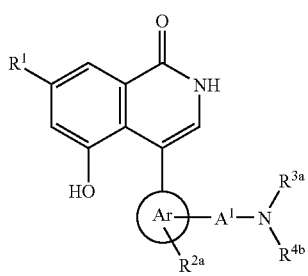

(1c)

wherein ring Ar denotes a phenyl group, naphthyl group, 5- or 6-membered aromatic heterocycle or its condensed ring, R1 denotes a hydrogen atom or halogen atom, R2a denotes a hydrogen atom, halogen atom, hydroxy group, lower alkyl group which may be substituted with halogen atom, lower alkoxy group which may be substituted with halogen atom, nitro group, or amino group which may have substituents, A1 denotes a C1~C4 alkylene, R3a denotes a hydrogen atom or lower alkyl group which may be substituted with halogen atom, R4b denotes a lower alkyl group which may be substituted with halogen atom, or formula (3a)

-$Q^2R^{6a}$ (3a)

wherein Q2 denotes a C1~C4 alkylene, and R6a denotes a cycloalkyl group which may have substituents, cycloalkenyl group which may have substituents, phenyl group which may have substituents, naphthyl group which may have substituents, or 5- or 6-membered heterocycle which may have substituents and its condensed ring, or R3a and R4b are bound together to form a 5- or 6-membered heterocycle which may have substituents and its condensed ring, or a pharmacologically acceptable addition salt thereof.

5. The 4-substituted aryl-5-hydroxyisoquinolinone compound of claim 1, represented by a formula (1d)

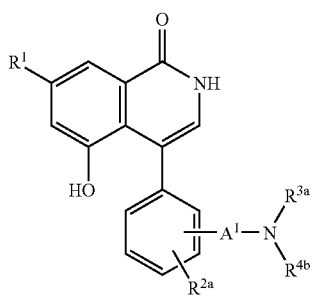

(1d)

wherein R1 denotes a hydrogen atom or halogen atom, R2a denotes a hydrogen atom, halogen atom, hydroxy group, lower alkyl group which may be substituted with halogen atom, lower alkoxy group which may be substituted with halogen atom, nitro group, or amino group which may have substituents, A1 denotes a C1~C4 alkylene, R3a denotes a hydrogen atom or lower alkyl group which may be substituted with halogen atom, R4b denotes a lower alkyl group which may be substituted with halogen atom, or formula (3a)

-$Q^2R^{6a}$ (3a)

wherein Q2 denotes a C1~C4 alkylene, and R6a denotes a cycloalkyl group which may have substituents, cycloalkenyl group which may have substituents, phenyl group which may have substituents, naphthyl group which may have substituents, or 5- or 6-membered heterocycle which may have substituents and its condensed ring, or R3a and R4b are bound together to form a 5- or 6-membered heterocycle which may have substituents and its condensed ring, or a pharmacologically acceptable addition salt thereof.

6. The 4-substituted aryl-5-hydroxyisoquinolinone compound of claim 1, represented by a formula (1e)

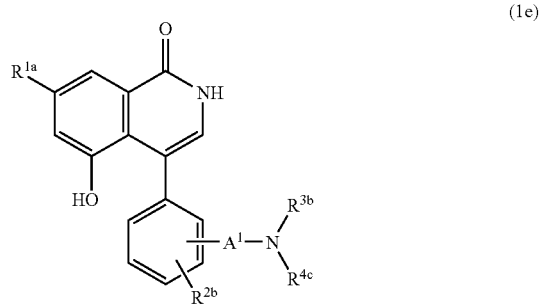

(1e)

wherein R1a denotes a hydrogen atom, R2b denotes a hydrogen atom, A1 denotes a C1~-C4 alkylene, and R3b and R4c are bound together to form a 5- or 6-membered heterocycle which may have substituents and its condensed ring, or a pharmacologically acceptable addition salt thereof.

7. The 4-substituted aryl-5-hydroxyisoquinolinone compound of claim 1, represented by a formula (1f)

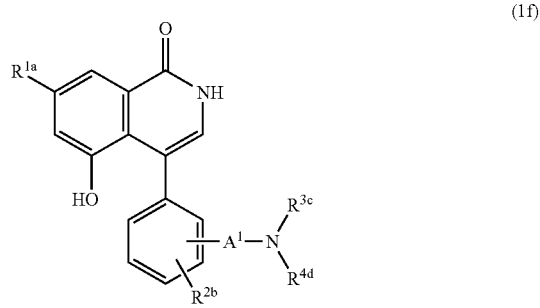

(1f)

wherein R1a denotes a hydrogen atom, R2b denotes a hydrogen atom, A1 denotes a C1~4 alkylene, R3c denotes a lower alkyl group which may be substituted with halogen atom, and R4d denotes a lower alkyl group which may be substituted with halogen atom, or a pharmacologically acceptable addition salt thereof.

8. The 4-substituted aryl-5-hydroxyisoquinolinone compound of claim 1, represented by a formula (1g)

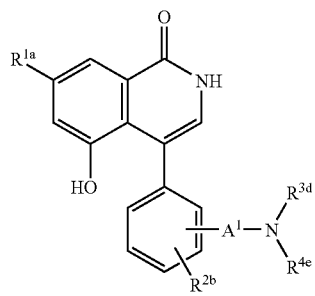

(1g)

wherein R1a denotes a hydrogen atom, R2b denotes a hydrogen atom, A1 denotes a C1~C4 alkylene, R3d denotes a hydrogen atom or lower alkyl group which may be substituted with halogen atom, R4e denotes formula (3a)

-Q²-R⁶ᵃ (3a)

wherein Q2 denotes a C1~C4 alkylene, and R6a denotes a cycloalkyl group which may have substituents, cycloalkenyl group which may have substituents, phenyl group which may have substituents, naphthyl group which may have substituents, or 5- or 6-membered heterocycle which may have substituents and its condensed ring, or a pharmacologically acceptable addition salt thereof.

9. The compound of claim 1, wherein the compound represented by said formula (1) is selected from the group consisting of 1,2-dihydiro-4-[4-(dimethylaminomethyl) phenyl]-5-hydroxy-1-oxoisoquiinoline, 1,2-dihydro-5-hydroxy-4-[4-[(N-methylbenzylamino)methyl]phenyl]-1-oxoisoquinoline, 1,2-dihydro-5-hydroxy-4-[4-[(N-methyl-2-phenylethylamino)methyl]phenyl]-1-oxoisoquinoline, 1,2-dihydro-5-hydroxy-4-[4-[(N-methyl-3-phenylpropylamino)methyl]phenyl]-1- oxoisoquinoline, 1,2-dihydro-5-hydroxy-4-[4-[(N-methylcyclohexylmethylamino) methyl] phenyl]-1-oxoisoquinoline, 1,2-dihydro-5-hydroxy-1-oxo-4-[4-[(pyrrolidin-1-yl)methyl]phenyl]isoquinoline and 1,2-dihydro-5-hydroxy-1-oxo-4-[4-[(4-phenyl-1,2,3,6-tetrahydropyridin-1-yl)methyl]phenyl]isoquinoline.

10. An inhibitor of poly (ADP-ribose)synthetase comprising at least one compound according to claim 1.

11. A pharmaceutical composition comprising a therapeutically effective amount of at least one compound according to claim 1 and at least one of a pharmacologically acceptable excipient or diluent.

12. A method for inhibiting poly (ADP-ribose) synthetase, comprising administering a therapeutically effective amount of the compound of claim 1 to a human being or an animal.

* * * * *